United States Patent
Lesmes

(10) Patent No.: US 11,484,194 B2
(45) Date of Patent: Nov. 1, 2022

(54) SYSTEMS AND METHODS FOR TESTING AND ANALYSIS OF VISUAL ACUITY AND ITS CHANGES

(71) Applicant: ADAPTIVE SENSORY TECHNOLOGY, INC., San Diego, CA (US)

(72) Inventor: Luis Andres Lesmes, San Diego, CA (US)

(73) Assignee: ADAPTIVE SENSORY TECHNOLOGY, INC., San Diego, CA (US)

(*) Notice: Subject to any disclaimer, the term of this patent is extended or adjusted under 35 U.S.C. 154(b) by 416 days.

(21) Appl. No.: 16/626,235

(22) PCT Filed: Jun. 22, 2018

(86) PCT No.: PCT/US2018/039137
§ 371 (c)(1),
(2) Date: Dec. 23, 2019

(87) PCT Pub. No.: WO2018/237347
PCT Pub. Date: Dec. 27, 2018

(65) Prior Publication Data
US 2020/0113432 A1 Apr. 16, 2020

Related U.S. Application Data

(60) Provisional application No. 62/524,414, filed on Jun. 23, 2017.

(51) Int. Cl.
*A61B 3/032* (2006.01)
*A61B 3/00* (2006.01)

(52) U.S. Cl.
CPC .............. *A61B 3/032* (2013.01); *A61B 3/00* (2013.01); *A61B 3/0041* (2013.01)

(58) Field of Classification Search
CPC ..... A61B 3/032; A61B 3/0025; A61B 3/0041; A61B 3/022; A61B 3/00; A61B 5/378;
(Continued)

(56) References Cited

U.S. PATENT DOCUMENTS 9,066,667 B1   6/2015  Berme et al.
10,631,722 B2  4/2020  Asaoka et al.
(Continued)

FOREIGN PATENT DOCUMENTS

WO   WO-2016190200 A1   12/2016
WO   WO-2016207684 A1   12/2016
WO   WO-2018237347      12/2018

OTHER PUBLICATIONS

Bailey et al.: Visual acuity testing. From the laboratory to the clinic. Vision Research 90:2-9 (2013).
(Continued)

*Primary Examiner* — Brandi N Thomas
(74) *Attorney, Agent, or Firm* — Wilson Sonsini Goodrich & Rosati

(57) ABSTRACT

Disclosed herein are system and method for testing and analysis of visual acuity and changes using an acuity model, the acuity model generated based on one or more acuity chart design parameters and candidate acuity parameters calculated using the acuity test data of the subject, the acuity model comprising a chart-specific psychometric function determined using a family of multiple-optotype psychometric functions, and wherein the acuity model is configurable to estimate possibility of obtaining the acuity test data of the subject.

15 Claims, 30 Drawing Sheets

(58) Field of Classification Search
CPC ......... A61B 3/024; A61B 3/103; A61B 3/113; A61B 5/165; A61B 3/0091; A61B 3/028; A61B 3/10; A61B 3/1015; A61B 5/024; A61B 5/11; A61B 5/369; A61B 5/38; A61B 3/0033; A61B 3/005; A61B 3/08; A61B 5/4023; A61B 5/7275; A61B 2562/0219; A61B 2562/0223; A61B 3/0058; A61B 3/09; A61B 3/14; A61B 5/1114; A61B 5/16; A61B 5/163; A61B 5/398; A61B 5/4088; A61B 5/6814; A61B 5/6831; A61B 8/10; G02C 7/02; G02C 7/027; G02C 7/063; G02C 7/00; G02C 7/024

See application file for complete search history.

(56) References Cited

U.S. PATENT DOCUMENTS

| | | | |
|---|---|---|---|
| 2010/0007851 A1 | 1/2010 | Lu et al. | |
| 2015/0150444 A1 | 6/2015 | Bex et al. | |
| 2017/0290504 A1* | 10/2017 | Khaderi | A63F 13/25 |
| 2021/0045629 A1 | 2/2021 | Lesmes | |

OTHER PUBLICATIONS

Dixon et al.: A method for obtaining and analyzing sensitive data. Journal of the American Statistical Association 43:109-126 (1948).
Fine et al.: Comparing perceptual learning across tasks: A review. Journal of vision 2(2):5-5 (2002).
Gutstein et al.: Interactive thresholding of central acuity under contrast and luminance conditions mimicking real world environments: 1, evaluation against LogMAR charts. J Comput Sci Syst Biol 8:225-232 (2015).
Hacker et al.: A revised table of d' for M-alternative forced choice. Perception & Psychophysics 26(2):168-170 (1979).
Kaiser. Prospective evaluation of visual acuity assessment: a comparison of snellen versus ETDRS charts in clinical practice (an AOS Thesis). Transactions of the American Ophthalmological Society 107: 311-324 (2009).
Lesmes et al.: Developing Bayesian adaptive methods for estimating sensitivity thresholds (d') in Yes-No and forced-choice tasks. Frontiers in Psychology 6:1070 (2015).
Mittelviefhaus et al.: [The Freiburg Vision Test. A computer-assisted procedure with sequential strategy], Der Ophthalmologe : Zeitschrift Der Deutschen Ophthalmologischen Gesellschaft 90(2):132-135 (1993).
PCT/US2018/039137 International Search Report and Written Opinion dated Sep. 17, 2018.
Rice et al.: Comparison of the amblyopia treatment study HOTV and electronic-early treatment of diabetic retinopathy study visual acuity protocols in children aged 5 to 12 years. American Journal of Ophthalmology 137(2):278-282 (2004).
Watson et al.: QUEST: A Bayesian adaptive psychometric method. Perception & Psychophysics 33(2):113-120 (1983).
EP18821004.1 European Search Report Opinion dated Feb. 8, 2021.
Japanese Patent Application No. 2020-520423 First Office Action dated May 30, 2022.

* cited by examiner

Fig. 2A

| | |
|---|---|
| HKDCN | 20/200 |
| SHZOR | 20/160 |
| ZVSRO | 20/125 |
| NKHDC | 20/100 |
| HSROZ | 20/80 |
| VNKCD | 20/63 |
| ROZSV | 20/50 |
| DCVZN | 20/40 |
| SHOKR | 20/32 |
| CNDHK | 20/25 |
| KDCVS | 20/20 |
| OZNRH | 20/16 |
| SVODK | 20/12.5 |
| ZORHN | 20/10.0 |

Fig. 2B

| | |
|---|---|
| D | 20/200 |
| HK | 20/100 |
| SHZ | 20/70 |
| NKHD | 20/50 |
| SHOKR | 20/40 |
| CNDHKO | 20/30 |
| DKZORHN | 20/25 |
| VZNROZSV | 20/20 |
| VSRONKHD | 20/15 |
| HKDCNSHZ | 20/13 |
| KOVNSROHO | 20/10 |

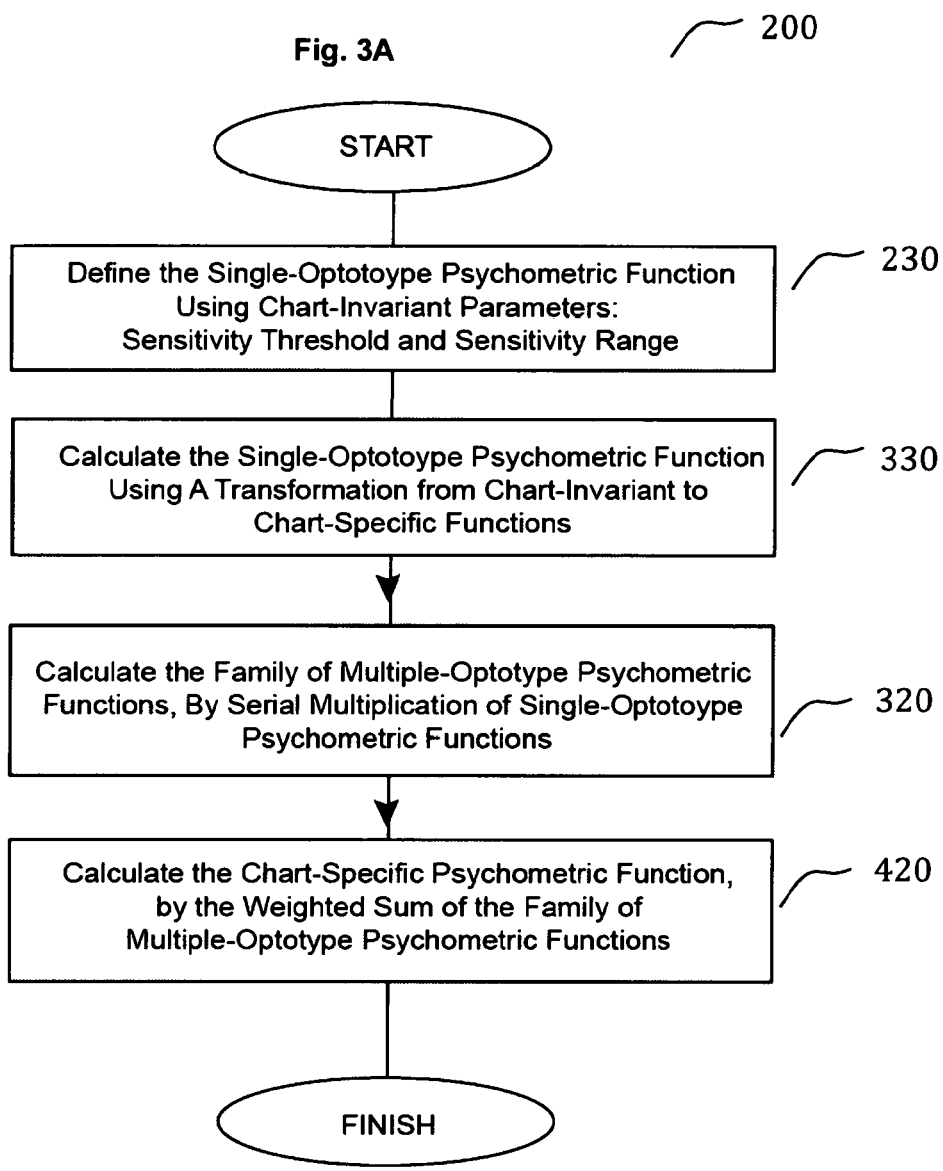

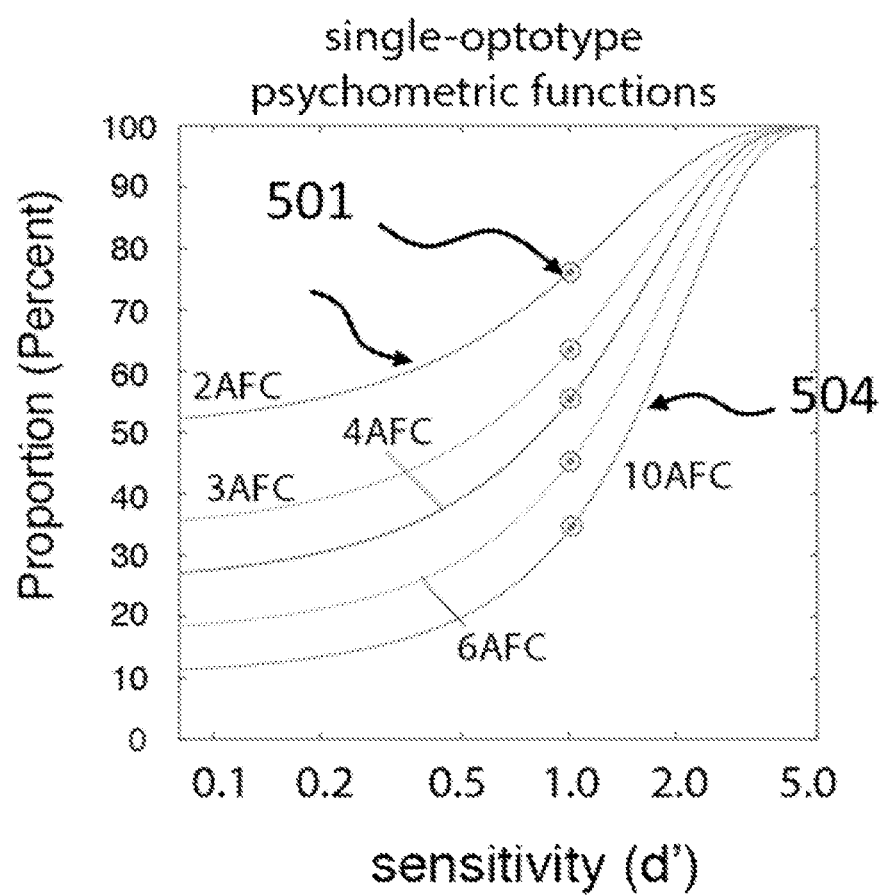

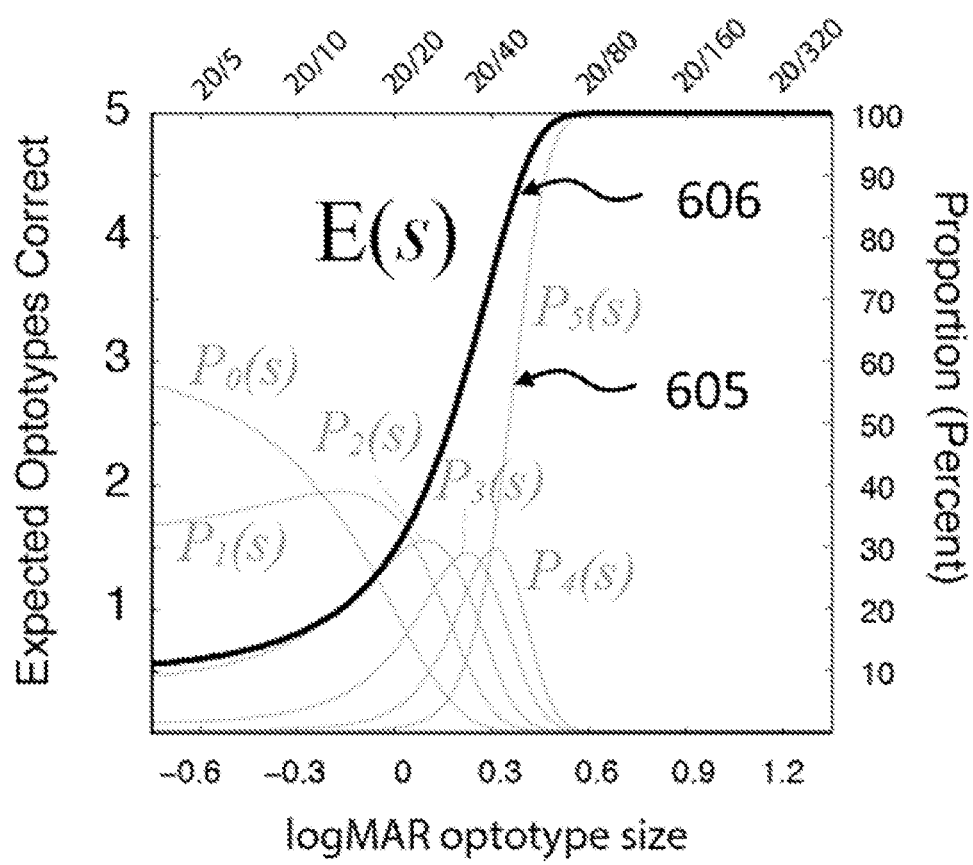

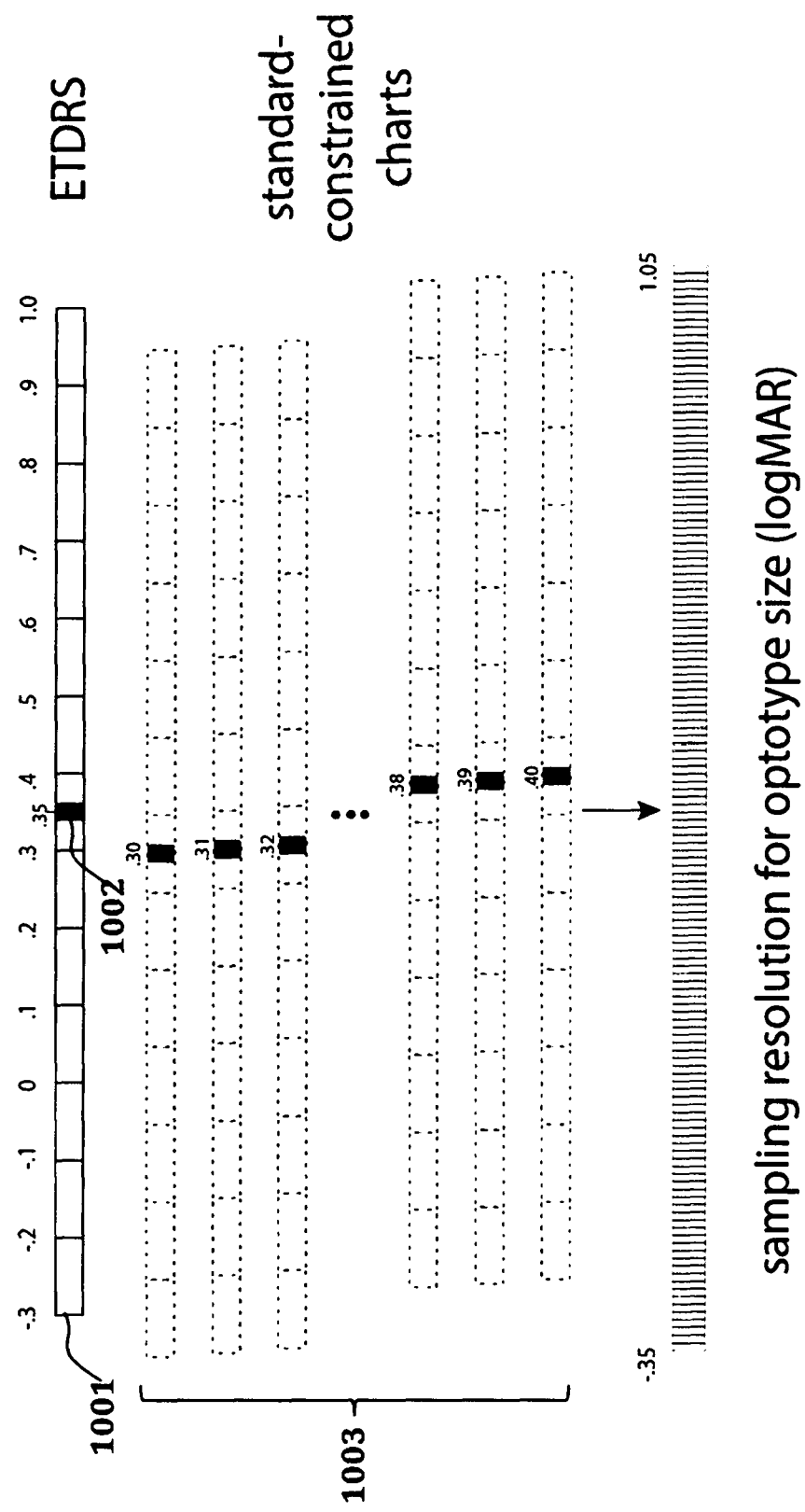

HKDCN
SHZOR
ZVSRO
NKHDC
HSROZ
VNKCD
ROZSV
DCVZN
SHOKR
CNDHK
KDCVS
OZNRH
SVCOK
ZORHN

Fig. 22B

HKDCN
SHZOR
ZVSRO
NKHDC
HSROZ
VNKCD
ROZSV
DCVZN
SHOKR
CNDHK
KDCVS
OZNRH
SVCOK
ZORHN

Fig. 22C

HKDCN
SHZOR
ZVSRO
NKHDC
HSROZ
VNKCD
ROZSV
DCVZN
SHOKR
CNDHK
KDCVS
OZNRH
SVCOK
ZORHN

Fig. 22D

HKDCN
SHZOR
ZVSRO
NKHDC
time 1   HSROZ
time 2   VNKCD
ROZSV
DCVZN
SHOKR
CNDHK
KDCVS
OZNRH
SVCOK
ZORHN Fig. 23.
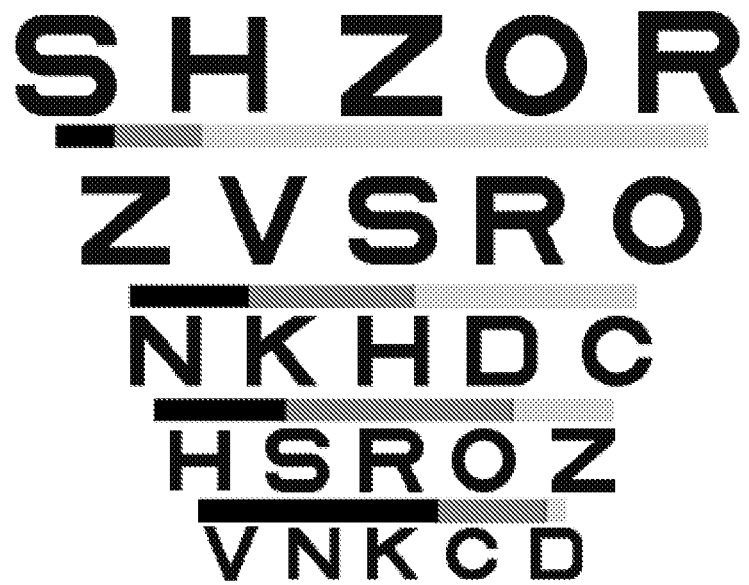

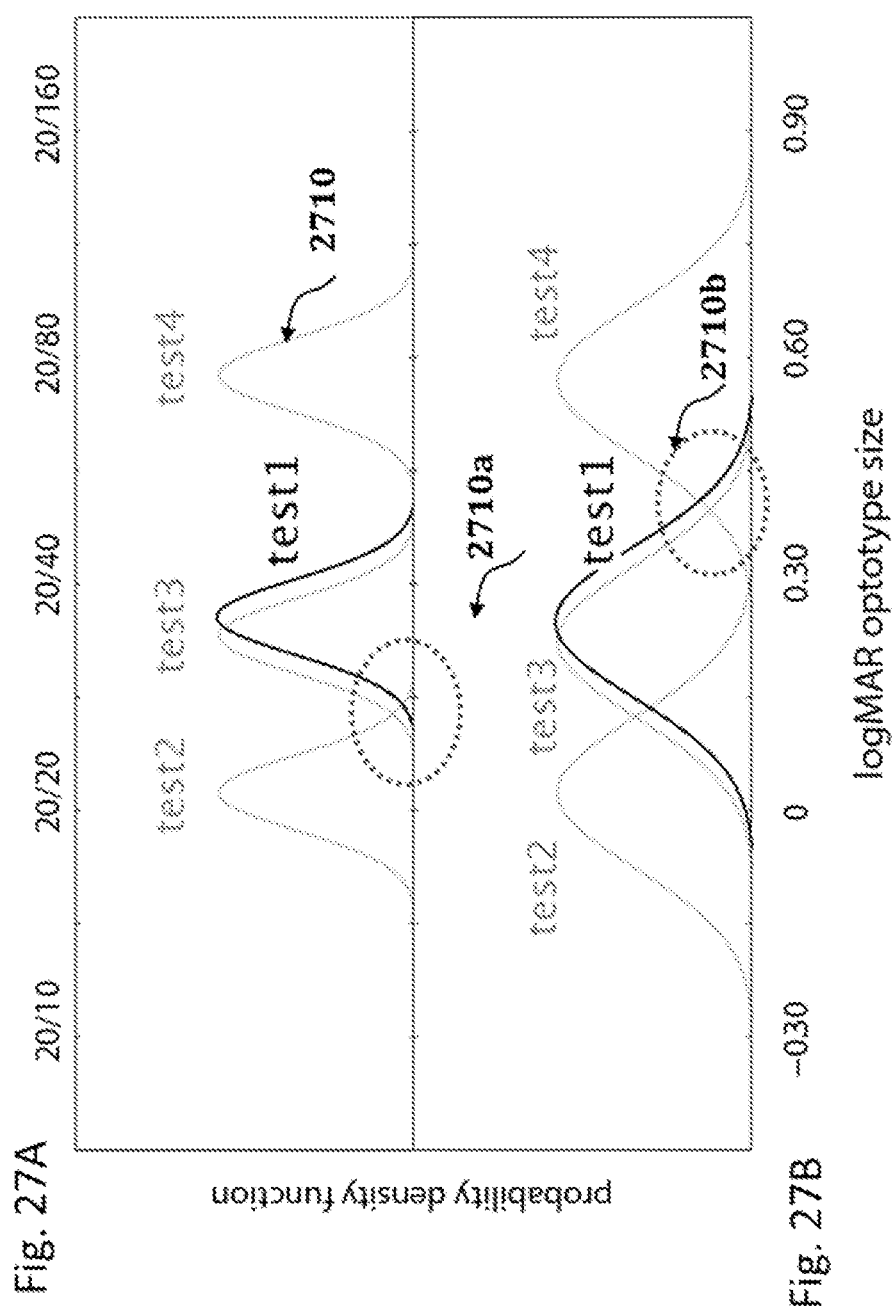

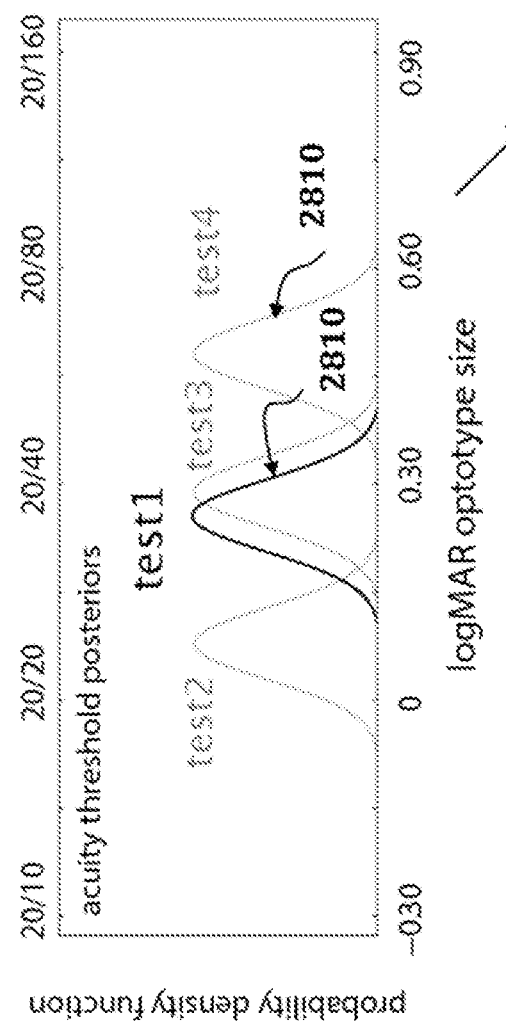
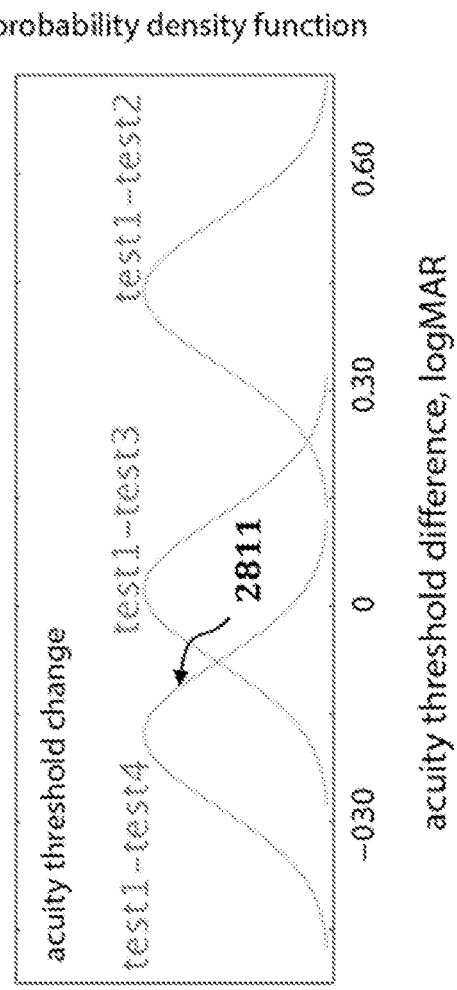

SYSTEMS AND METHODS FOR TESTING AND ANALYSIS OF VISUAL ACUITY AND ITS CHANGES

CROSS-REFERENCE

The present application claims the benefit of U.S. Provisional Application No. 62/524,414, filed Jun. 23, 2017, which is entirely incorporated herein by reference.

BACKGROUND

Visual acuity charts are commonly used to measure visual acuity because they are standardized and easy to use, and can be widely distributed. Testing of visual acuity typically involves asking a patient to identify optotypes—visual patterns of letters or objects—presented on a test slide (or series of slides). Each slide includes one or more optotypes, arranged in one or more lines at one time. The patient's ability to identify optotypes as a function of their size is registered and scored to yield an estimate of visual acuity. The estimate of visual acuity obtained, e.g., the smallest optotype size that the patient can reliably see, can depend fundamentally on the design of testing and scoring, which is based on pre-determined rules and heuristics specific to each chart.

SUMMARY OF THE INVENTION

Two approaches to visual acuity testing have come to dominate the current art: chart tests in which patients identify multiple lines of optotypes presented at one time, or computerized testing in which optotypes are presented one at a time. The computerized test has gained recent favor, because it provides the potential advantage of increased test resolution, via the flexible and precise sampling of optotype size on digital displays, and the application of adaptive and personalized test strategies that focus testing to the specific vision of the patient.

One important shortcoming in existing acuity testing is the difference in chart design between charts used for clinical trials and clinical practice. Therefore, acuity testing results collected in clinical practice are only imprecisely related to those collected on the "gold standard" chart used in clinical trials. Due to long testing times needed for clinical trials, this chart design and testing standard remains unfeasible for clinical testing by eye care specialists or general practitioners. Even allowing for the longer times allowable in clinical research, the acuity testing results obtained with pediatric charts (e.g., HOTV, Lea designs) exhibit systemic biases when compared to those obtained from charts designed for adults.

The testing of visual acuity with precision presents a challenge. For many charts currently used in the clinical setting, acuity testing provides only qualitative rather than quantitative results (e.g., 20/20 or 20/40). Furthermore, the variety of chart designs in circulation across clinical testing sites can make it difficult to compare and coordinate acuity testing obtained with different charts. Without precision and concordance between the charts used for clinical vision testing, it remains difficult to track how vision changes with disease or treatment.

The systems and methods disclosed herein for testing and analysis of visual acuity address existing problems in acuity testing. Advantages of the systems and methods disclosed herein include development of personalized acuity charts based on subject-specific (interchangeable as chart-invariant) information related to his/her visual acuity. In some embodiments, another advantage of the systems and methods disclosed herein includes the capability of analyzing visual acuity data collected with a wide spectrum of acuity charts including but not limited to legacy charts. In some embodiments, yet another advantage of the systems and methods disclosed herein includes generation of precise acuity parameters that are independent of the acuity chart design(s) used to collect the data.

In some embodiments, disclosed herein is a scoring algorithm (interchangeable as algorithm S herein) that enables the analysis of visual acuity data collected optionally on different acuity chart designs. In some cases, disclosed herein is an adaptive algorithm (interchangeable as algorithm A) that improves the quality of visual acuity data by generating or selecting personalized chart designs that focus precisely on the acuity of the test subject. In some cases, disclosed herein is a combination algorithm, which combines algorithms A and S in a re-iterative fashion: the evaluation of previously collected acuity data (from the subject or from a population) is used to personalize chart designs for the collection of acuity chart data using algorithm A. In turn, that data can be scored using algorithm S, which provides an updated estimate of the patient's visual acuity. This re-iterative process can provide estimates of visual acuity with high precision and reduced testing times. In some embodiments, disclosed herein is an acuity model for analyzing visual acuity, which predicts visual performance during testing with different acuity chart designs. In some cases, such acuity models provide the foundation for algorithms S and A. In some embodiments, the acuity models disclosed herein provide a powerful description of acuity chart performance, which generalizes to predict visual performance across different acuity charts, using model parameters specific to the subject, and/or model parameters specific to each chart design. These model parameters specific to the subject (interchangeably herein as chart-invariant parameters) can provide the valuable acuity parameters that can be used to track visual health over time.

For instances, in the acuity models disclosed herein, the distinction of chart-specific and chart-invariant metrics (interchangeable as parameters) provides flexibility and versatility to the estimates of visual acuity. Such two sets of acuity metrics can be important and complementary. The set of chart-specific metrics may describe visual acuity within the context of the specific acuity chart used during testing. An alternative set of chart-invariant metrics can describe visual acuity independently of the design features of acuity charts. These comprehensive parameters therefore may have the flexibility to deliver acuity metrics that are specific to, or independent of, the acuity chart used for testing. The chart-specific metrics can be important for research and development applications that use the same chart over time. The chart-invariant metric approach is important to evaluate and compare data across different clinical practices and populations. As shown in FIG. 3A, a flow chart of an exemplary embodiment of generating the chart-invariant acuity model may include an operation 230 using chart-invariant acuity parameters, which then may be transformed into chart-specific acuity parameters 330, depending on the design factors of the acuity chart.

The acuity models disclosed herein can also provide a foundation for novel presentations of visual acuity data. The visualization tools may help patients and clinicians to understand the changes in acuity that are being measured.

Since the same chart can often be used to measure vision in different eyes, at different distances, or in situations that require repeated measure of visual acuity (e.g., tracking the progression of an eye disease or treatment effects), it is difficult to prevent contamination between conditions. The recommendations of the National Academy of Sciences-National Research Council (NAS-NRC) committee and ANSI (American National Standards Institute) standards dictate that acuity charts should comprise multiple lines of optotypes that are logarithmically-decreasing in size. In addition to other design recommendations (5-10 optotypes per line, sampled randomly without replacement), the standards recommend against the single letter presentation used by computerized adaptive acuity methods.

Unlike traditional adaptive acuity testing methods that optimize optotype selection for only one letter at one size, the system and method disclose herein can advantageously enable composite optimization of acuity charts that concurrently estimate chart-specific and chart-invariant acuity metrics. Additional advantages associated with the methods and systems disclosed herein includes but are not limited to: a precise personalized focus on each individual subject while adhering to chart design standards, rapid testing times, comparable precision to time-consuming single-letter acuity tests, and visual acuity metrics that described the subject's vision independently of optotype sizes, test charts, or testing procedures. Both sets of acuity parameters, whether chart-specific or chart-invariant are interchangeable and inter-translatable, given knowledge of acuity chart design.

In some embodiments, the systems and methods disclosed herein includes a chart-based adaptive acuity test, which provides the advantages of standardization provided by chart-based testing, with the advantages of flexibility and precision provided by single-letter testing. The systems and methods disclosed herein can apply Bayesian adaptive algorithms to personalize and precisely focus acuity charts to optimally test the vision of each subject, while adhering to design constraints or recommendations from ruling committees, or more generally, while maintaining any desired design constraints at all. In some embodiments, the development of design-constrained optimization methods for visual acuity testing optionally using Bayesian adaptive algorithms and a signal detection framework provides one or more of: the adherence to chart design standards; precise personalization by adaptive testing that focuses on the individual; the short testing time of charts; the precision of longer single-letter acuity tests; correction for guessing behavior with different optotype sets; and visual acuity estimates that are invariant with respect to practical issues of acuity testing, e.g., the design of the visual test or the optotypes used.

In one aspect, disclosed herein is a computer-implemented method for generating an acuity model for scoring visual acuity of a subject, the method comprising: a) obtaining one or more acuity chart design parameters; b) collecting acuity test data of the subject; c) selecting a first set of chart-specific acuity parameters from one or more sets of candidate acuity parameters; d) generating an acuity model comprising: i) generating a single-optotype psychometric function, the single-optotype psychometric function comprising the first set of chart-specific acuity parameters; ii) calculating a family of multiple-optotype psychometric functions using the single-optotype psychometric function; and iii) generating a chart-specific psychometric function using the family of multiple-optotype psychometric functions, the chart-specific psychometric function comprising a second set of chart-specific acuity parameters, wherein the acuity model is configurable to estimate possibility of obtaining the acuity test data of the subject based on the one or more acuity chart design parameters. In some embodiments, the method further comprising, subsequent to (c) and prior to (i), generating a sensitivity-based psychometric function comprising a first set of chart-invariant sensitivity parameters, and wherein the first set of chart-invariant sensitivity parameters comprises a sensitivity threshold and a sensitivity range, and wherein the first set of chart-invariant sensitivity parameters are generated based on the first set of chart-specific acuity parameters. In some embodiments, the sensitivity-based psychometric function is independent of the one or more acuity chart design parameters. In some embodiments, the sensitivity-based psychometric function is generated based on the one or more acuity chart design parameters and/or one or more additional parameters of the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the method further comprising translating the sensitivity-based psychometric function to the single-optotype psychometric function, prior to (i). In some embodiments, the first set of chart-specific acuity parameters comprises an acuity threshold and an acuity range. In some embodiments, the single-optotype psychometric function is chart-specific. In some embodiments, the second set of chart-specific acuity parameters comprises an acuity threshold and an acuity range. In some embodiments, the first set or the second set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the first set or the second set of chart-specific acuity parameters comprises one or more numerical values. In some embodiments, the first set or the second set of chart-specific acuity parameters comprises at least one posterior probability density function for a parameter thereof. In some embodiments, the acuity test data of the subject comprises data from at least two different test conditions. In some embodiments, the first set or the second set of chart-specific acuity parameters comprises posterior probability density functions for an acuity threshold from the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, (iii) further comprising using a weighted sum of the family of multiple-optotype psychometric functions. In some embodiments, the weighting of the family of psychometric functions is based on the acuity chart data of the subject. In some embodiments, the weighting is determined manually by a user or automatically by a computer program. In some embodiments, (b) further comprising displaying one or more acuity charts generated based on the one or more acuity chart design parameters to the subject. In some embodiments, each of the one or more acuity charts comprises at least one optotype, wherein the at least one optotype selected from a library of optotypes. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the one or more sets of candidate acuity parameters are generated based on the one or more acuity chart design parameters, the acuity test data of the subject, or both.

In another aspect, disclosed herein is a computer-implemented method for scoring visual acuity of a subject, the method comprising: a) obtaining one or more acuity chart design parameters; b) collecting acuity test data of the subject; c) generating one or more sets of candidate acuity parameters based on the one or more acuity chart design parameters, the acuity test data of the subject, or both; d) generating an acuity model comprising generating one or more chart-specific psychometric functions, each chart-specific psychometric function comprising a set of chart-specific acuity parameters of the one or more sets of chart-specific acuity parameters; e) generating the probabilities of observing the acuity test data using the acuity model and the one or more sets of candidate acuity parameters; f) ranking the one or more sets of candidate acuity parameters for the subject based on the probabilities; and g) selecting one set from the one or more sets of candidate acuity parameters for the subject based on the rankings. In some embodiments, each set of the candidate acuity parameters comprises: an acuity threshold and an acuity range. In some embodiments, each set of the candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the candidate acuity parameters comprises a posterior probability density function for the one or more acuity parameters. In some embodiments, each set of the candidate acuity parameters comprises a posterior probability density function for each of the one or more acuity parameters. In some embodiments, (b) comprises summarizing acuity test data from the subject. In some embodiments, the method further comprises, subsequent to (g), displaying visual acuity test result to the subject or the user, the test result comprising the selected set of candidate acuity parameters. In some embodiments, the acuity test data of the subject comprises data from only a first test condition. In some embodiments, the acuity test data of the subject comprises data from a first and second test conditions. In some embodiments, the selected set of the candidate acuity parameters comprises a first posterior probability density function of an acuity threshold or an acuity range. In some embodiments, b) comprises selecting data with the first test condition. In some embodiments, the method further comprises, subsequent to g), selecting data with the second test condition from the acuity test data of the subject; and repeating c) to g). In some embodiments, the selected set of the candidate acuity parameters comprises a second posterior probability density function for the acuity threshold or the acuity range. In some embodiments, the method further comprises obtaining a difference distribution using the first and second posterior probability density functions. In some embodiments, the method comprises calculating a change in acuity threshold or acuity range between the first and the second test conditions based on the difference distribution. In some embodiments, the visual acuity test result is chart-invariant or chart-specific. In some embodiments, (e) is based on Bayes' theorem or maximum likelihood estimation. In some embodiments, the posterior probability density function is a Bayesian posterior probability density function. In some embodiments, the first or the second posterior probability density function is a Bayesian posterior probability density function. In some embodiments, (d) comprises: generating a single-optotype psychometric function, the single-optotype psychometric function comprising the first set of chart-specific acuity parameters; calculating a family of multiple-optotype psychometric functions using the single-optotype psychometric function; and generating a chart-specific psychometric function using the family of multiple-optotype psychometric functions, the chart-specific psychometric function comprising a second set of chart-specific acuity parameters. In some embodiments, the method further comprises, prior to generating the single-optotype psychometric function, generating a sensitivity-based psychometric function comprising a first set of chart-invariant sensitivity parameters. In some embodiments, the sensitivity-based psychometric function is independent of the one or more acuity chart design parameters. In some embodiments, the first set of chart-invariant sensitivity parameters comprises a sensitivity threshold and a sensitivity range, and wherein the first set of chart-invariant sensitivity parameters are generated based on the one or more sets of candidate acuity parameters. In some embodiments, the sensitivity-based psychometric function is generated based on the one or more acuity chart design parameters and/or one or more additional parameters of the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the method further comprises translating the sensitivity-based psychometric function to the single-optotype psychometric function. In some embodiments, the set of chart-specific acuity parameters comprises an acuity threshold and an acuity range. In some embodiments, the single-optotype psychometric function is chart-specific. In some embodiments, the set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the set of chart-specific acuity parameters comprises one or more numerical values. In some embodiments, the set of chart-specific acuity parameters comprises at least one posterior probability density function for a parameter thereof. In some embodiments, the acuity test data of the subject comprises data from at least two different test conditions. In some embodiments, the set of chart-specific acuity parameters comprises posterior probability density functions for an acuity threshold of the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, generating a chart-specific psychometric function further comprising using a weighted sum of the family of multiple-optotype psychometric functions. In some embodiments, the weighting of the family of psychometric functions is based on the acuity chart data of the subject. In some embodiments, the weighting is determined manually by a user or automatically by a computer program. In some embodiments, (b) further comprises displaying one or more acuity charts generated based on the one or more acuity chart design parameters to the subject. In some embodiments, each of the one or more acuity charts comprises at least one optotype, wherein the at least one optotype selected from a library of optotypes. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the method further comprises: h) generating a plurality of candidate acuity charts based on the one or more chart design parameters; and i) selecting one or more of the plurality of candidate acuity charts for acuity testing of the subject based on the ranking of the plurality of candidate acuity charts, wherein the ranking is based on the selected set of candidate acuity parameters for the subjects. In some embodiments, the method further comprising, subsequent to (b); collecting data from the subject using the selected one or more candidate acuity charts; if a stopping criterion has not been met, repeating steps c) to g) and steps h) to i) in until the stopping criteria has been met.

In yet another aspect, disclosed herein is a computer-implemented method for adaptively evaluating visual acuity of a subject, the method comprising: a) obtaining one or more acuity chart design parameters; b) collecting acuity test data of the subject; c) generating one or more sets of candidate acuity parameters based on one or more acuity chart design parameters and the acuity test data of the subject, each of the one or more sets of candidate acuity parameters comprises a rank obtained by analyzing the acuity test data of the subject; d) generating a plurality of candidate acuity charts based on the one or more acuity chart design parameters; e) ranking the plurality of candidate acuity charts based on the rank of each of the one or more sets of candidate acuity parameters; and f) selecting one or more acuity charts from the plurality of candidate acuity charts based on ranks thereof to be presented to the subject for acuity testing. In some embodiments, the method further comprises, subsequent to f), presenting the one or more selected acuity charts to the subject. In some embodiments, the method further comprises, subsequent to f) updating the acuity test data with new data collected from the subject using the one or more selected acuity charts. In some embodiments, the method further comprises repeating: presenting the one or more selected acuity charts to the subject; updating the acuity test data with new data collected from the subject using the one or more selected acuity charts; and steps b) to f); until a stopping criterion has been met. In some embodiments, each set of the one or more sets of candidate acuity parameters comprises: an acuity threshold and an acuity range. In some embodiments, each set of the one or more sets of candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the one or more sets of candidate acuity parameters comprises a posterior probability density function for the one or more acuity parameters. In some embodiments, each set of the one or more sets of candidate acuity parameters comprises a posterior probability density function for each of the one or more acuity parameters. In some embodiments, (b) comprises summarizing acuity test data from the subject. In some embodiments, the acuity test data of the subject comprises data from only a first test condition. In some embodiments, the acuity test data of the subject comprises data from a first and second test conditions. In some embodiments, each set of the one or more sets of candidate acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the acuity test data of the subject comprises data from at least two different test conditions. In some embodiments, each set of the one or more sets of candidate acuity parameters comprises posterior probability density function for an acuity threshold or an acuity range. In some embodiments, the one or more acuity chart design parameters comprises: a total number of optotypes, a number of optotypes per line, a method of optotype sampling, an optotype size, a number of lines, and a response of the subject, or a combination thereof. In some embodiments, each of the candidate acuity charts comprises at least one optotype, wherein the at least one optotype selected from a library of optotypes. In some embodiments, one or more of candidate acuity charts are of a contrast that is about 25%, 2.5%, or 1.5% of a normal contrast in standard ETDRS charts or Sloane charts. The method of claim 90, wherein the at least one optotypes is a letter, a number, or a symbol.

In yet another aspect, disclosed herein is a computer-implemented system for generating an acuity model for scoring visual acuity of a subject, the system comprising: a digital processing device comprising an operating system configured to perform executable instructions and a memory; and a computer program including instructions executable by the digital processing device to create a scoring application comprising a software module configured to: a) obtain one or more acuity chart design parameters; b) collect acuity test data of the subject; c) select a first set of chart-specific acuity parameter from one or more sets of candidate acuity parameters; d) generate an acuity model comprising: i. generate a single-optotype psychometric function, the single-optotype psychometric function comprising the first set of chart-specific acuity parameters; ii. calculate a family of multiple-optotype psychometric functions using the single-optotype psychometric function; and iii. generate a chart-specific psychometric function using the family of multiple-optotype psychometric functions, the chart-specific psychometric function comprising a second set of chart-specific acuity parameters, wherein the acuity model is configurable to estimate possibility of obtaining the acuity test data of the subject based on the one or more acuity chart design parameters. In some embodiments, the system further comprises, subsequent to (c) and prior to (i), generate a sensitivity-based psychometric function comprising a first set of chart-invariant sensitivity parameters, and wherein the first set of chart-invariant sensitivity parameters comprises a sensitivity threshold and a sensitivity range, and wherein the first set of chart-invariant sensitivity parameters are generated based on the first set of chart-specific acuity parameters. In some embodiments, the sensitivity-based psychometric function is independent of the one or more acuity chart design parameters. In some embodiments, the sensitivity-based psychometric function is generated based on the one or more acuity chart design parameters and/or one or more additional parameters of the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the system further comprises translate the sensitivity-based psychometric function to the single-optotype psychometric function, prior to (i). In some embodiments, the first set of chart-specific acuity parameters comprises an acuity threshold and an acuity range. In some embodiments, the single-optotype psychometric function is chart-specific. In some embodiments, the second set of chart-specific acuity parameters comprises an acuity threshold and an acuity range. In some embodiments, the first set or the second set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the first set or the second set of chart-specific acuity parameters comprises one or more numerical values. In some embodiments, the first set or the second set of chart-specific acuity parameters comprises at least one posterior probability density function for a parameter thereof. In some embodiments, the acuity test data of the subject comprises data from at least two different test conditions. In some embodiments, the first set or the second set of chart-specific acuity parameters comprises posterior probability density functions for an acuity threshold from the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, (iii) further comprises using a weighted sum of the family of multiple-optotype psychometric functions. In some embodiments, the weighting of the family of psychometric functions is based on the acuity chart data of the subject. In some embodiments, the weighting is determined manually by a user or automatically by a computer program. In some embodiments, (b) further comprising use one or more acuity charts generated based on the one or more acuity chart design parameters. In some embodiments, each of the one or more acuity charts comprises at least one optotype, wherein the at least one optotype selected from a library of optotypes. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the one or more sets of candidate acuity parameters are generated based on the one or more acuity chart design parameters, the acuity test data of the subject, or both.

In yet another aspect, disclosed herein is a computer system for generating an acuity model for scoring visual acuity of a subject, the system comprising: a digital processing device comprising an operating system configured to perform executable instructions and a memory; and a computer program including instructions executable by the digital processing device to create a scoring application comprising a software module configured to: a) obtain one or more acuity chart design parameters; b) collect acuity test data of the subject; c) generate one or more sets of candidate acuity parameters based on the one or more acuity chart design parameters, the acuity test data of the subject, or both; d) generate an acuity model comprising generating one or more chart-specific psychometric functions, each chart-specific psychometric function comprising a set of chart-specific acuity parameters of the one or more sets of chart-specific acuity parameters, e) generate the probabilities of observing the acuity test data using the acuity model and the one or more sets of candidate acuity parameters; f) rank the one or more sets of candidate acuity parameters for the subject based on the probabilities; and g) select one set from the one or more sets of candidate acuity parameters for the subject based on the rankings. In some embodiments, each set of the candidate acuity parameters comprises: an acuity threshold and an acuity range. In some embodiments, each set of the candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the candidate acuity parameters comprises a posterior probability density function for the one or more acuity parameters. In some embodiments, each set of the candidate acuity parameters comprises a posterior probability density function for each of the one or more acuity parameters. In some embodiments, (b) comprises summarize acuity test data from the subject. In some embodiments, the system further comprises, subsequent to (g), display visual acuity test result to the subject or the user, the result comprising the selected set of candidate acuity parameters. In some embodiments, the acuity test data of the subject comprises data from only a first test condition. In some embodiments, the acuity test data of the subject comprises data from a first and second test conditions. In some embodiments, the selected set of the candidate acuity parameters comprises a first posterior probability density function of an acuity threshold or an acuity range. In some embodiments, b) comprises select data with the first test condition. In some embodiments, the system further comprises, subsequent to g), select data with the second test condition from the acuity test data of the subject; and repeat c) to g). In some embodiments, the selected set of the candidate acuity parameters comprises a second posterior probability density function for the acuity threshold or the acuity range. In some embodiments, the system further comprises obtain a difference distribution using the first and second posterior probability density functions. In some embodiments, the system further comprises calculate a change in acuity threshold or acuity range between the first and the second test conditions based on the difference distribution. In some embodiments, the visual acuity test result is chart-invariant or chart-specific. In some embodiments, (e) is based on Bayes' theorem or maximum likelihood estimation. In some embodiments, the posterior probability density function is a Bayesian posterior probability density function. In some embodiments, the first or the second posterior probability density function is a Bayesian posterior probability density function. In some embodiments, (d) comprises: generating a single-optotype psychometric function, the single-optotype psychometric function comprising the first set of chart-specific acuity parameters; calculating a family of multiple-optotype psychometric functions using the single-optotype psychometric function; and generating a chart-specific psychometric function using the family of multiple-optotype psychometric functions, the chart-specific psychometric function comprising a second set of chart-specific acuity parameters. In some embodiments, the system further comprises prior to generating the single-optotype psychometric function, generate a sensitivity-based psychometric function comprising a first set of chart-invariant sensitivity parameters. In some embodiments, the sensitivity-based psychometric function is independent of the one or more acuity chart design parameters. In some embodiments, the first set of chart-invariant sensitivity parameters comprises a sensitivity threshold and a sensitivity range. In some embodiments, the sensitivity-based psychometric function is generated based on the one or more acuity chart design parameters and/or one or more additional parameters that are based on the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the system further comprises translate the sensitivity-based psychometric function to the single-optotype psychometric function. In some embodiments, the set of chart-specific acuity parameters comprises an acuity threshold and an acuity range. In some embodiments, the single-optotype psychometric function is chart-specific. In some embodiments, the set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the set of chart-specific acuity parameters comprises one or more numerical values. In some embodiments, the set of chart-specific acuity parameters comprises at least one posterior probability density function for a parameter thereof. In some embodiments, the acuity test data of the subject comprises data from at least two different test conditions. In some embodiments, the set of chart-specific acuity parameters comprises posterior probability density functions for an acuity threshold at the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, generating a chart-specific psychometric function further comprising using a weighted sum of the family of multiple-optotype psychometric functions. In some embodiments, the weighted sum of the family of psychometric functions is based on the acuity chart data of the subject. In some embodiments, the weighting is determined manually by a user or automatically by a computer program. In some embodiments, (b) further comprising displaying one or more acuity charts generated based on the one or more acuity chart design parameters to the subject. In some embodiments, each of the one or more acuity charts comprises at least one optotype, wherein the at least one optotype selected from a library of optotypes. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the system further comprises: h) generate a plurality of candidate acuity charts based on the one or more chart design parameters; and i) select one or more of the plurality of candidate acuity charts for acuity testing of the subject based on the ranking of the plurality of candidate acuity charts, wherein the ranking is based on the selected set of candidate acuity parameters for the subjects. In some embodiments, the system further comprises, subsequent to (b); collecting data from the subject using the selected one or more candidate acuity charts; if a stopping criterion has not been met, repeating steps c) to g) and steps h) to i) until the stopping criteria has been met.

In still yet another aspect, disclosed herein is a computer-implemented system for adaptively evaluating visual acuity of a subject, the system comprising: a digital processing device comprising an operating system configured to perform executable instructions and a memory; and a computer program including instructions executable by the digital processing device to create a scoring application comprising a software module configured for: a) obtaining one or more acuity chart design parameters; b) collecting acuity test data of the subject; c) generating one or more sets of candidate acuity parameters based on one or more acuity chart design parameters and the acuity test data of the subject, each of the one or more sets of candidate acuity parameters comprises a rank obtained by analyzing the acuity test data of the subject; d) generating a plurality of candidate acuity charts based on the one or more acuity chart design parameters; e) ranking the plurality of candidate acuity charts based on the rank of each of the one or more sets of candidate acuity parameters; and f) selecting one or more acuity charts from the plurality of candidate acuity charts based on ranks thereof to be presented to the subject for acuity testing. In some embodiments, the system further comprises, subsequent to f), present the one or more selected acuity charts to the subject. In some embodiments, the system further comprising, subsequent to f), update the acuity test data with new data collected from the subject using the one or more selected acuity charts. In some embodiments, the system further comprises repeat: present the one or more selected acuity charts to the subject; update the acuity test data with new data collected from the subject using the one or more selected acuity charts, and steps b) to f); until a stopping criterion has been met. In some embodiments, each set of the one or more sets of candidate acuity parameters comprises: an acuity threshold and an acuity range. In some embodiments, each set of the one or more sets of candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the one or more sets of candidate acuity parameters comprises a posterior probability density function for the one or more acuity parameters. In some embodiments, each set of the one or more sets of candidate acuity parameters comprises a posterior probability density function for each of the one or more acuity parameters. In some embodiments, (b) comprises summarize acuity test data from the subject. In some embodiments, the acuity test data of the subject comprises data from only a first test condition. In some embodiments, the acuity test data of the subject comprises data from a first and second test conditions. In some embodiments, each set of the one or more sets of candidate acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the acuity test data of the subject comprises data from at least two different test conditions. In some embodiments, each set of the one or more sets of candidate acuity parameters comprises posterior probability density function for an acuity threshold or an acuity range. In some embodiments, the one or more acuity chart design parameters comprises: a total number of optotypes, a number of optotypes per line, a method of optotype sampling, an optotype size, a number of lines, and a response of the subject, or a combination thereof. In some embodiments, each of the candidate acuity charts comprises at least one optotype, wherein the at least one optotype selected from a library of optotypes. In some embodiments, one or more of candidate acuity charts are of a contrast that is about 25%, 2.5%, or 1.5% of a normal contrast in standard ETDRS charts or Sloane charts. In some embodiments, the at least one optotypes is a letter, a number, or a symbol.

Consistent with other disclosed embodiments, non-transitory computer-readable storage media can store program instructions, which are executed by a processor to perform any of the methods described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 2A-2B show a non-limiting example of generating a library of visual acuity chart and sub-charts with different chart designs; in this case, an ETDRS chart (early treatment diabetic retinopathy study, FIG. 2A) and a Snellen chart (FIG. 2B);

FIG. 3A shows a non-limiting example of a flow chart of generating a chart-invariant acuity model;

FIG. 5 shows a non-limiting example of a set of chart-specific psychometric functions, which reflect the transformation of a chart-invariant single optotype psychometric function (in d' units) to a chart-specific single-optotype psychometric function, based on chart design factors that can include the number of response alternatives that dictate the guessing rate (from two alternative (2AFC) to ten alternative forced-choice (10AFC));

FIG. 6C shows a non-limiting example of a chart-specific psychometric function generated from a weighted sum of a family of multiple-optotype psychometric functions in FIG. 6B;

FIG. 10 shows a non-limiting example of producing an expansive library of candidate visual acuity charts, by determining varying the sampling pattern of optotype size, based on chart design principles;

FIGS. 11A-11F show non-limiting examples of candidate visual acuity charts using different anchor points based on a full standard-constraint acuity chart;

FIGS. 12A-12C show non-limiting examples of displaying a specific region or a subchart of a full standard-constrained visual acuity chart;

FIGS. 13A-13C show non-limiting examples of collecting a response from a subject with three different modes, in this case, the subject reads down the first column (FIG. 13A), reads line-by-line down the chart, starting from the top (FIG. 13B), or reads a single letter that is presented at the center of the screen (FIG. 13C);

FIG. 22 shows a non-limiting example of displaying the result of a visual acuity test.

FIG. 23 shows another non-limiting example of displaying the result of a visual acuity test to the subject.

FIG. 27A-27B show a non-limiting example of estimating visual acuity changes between different test conditions using Bayesian posterior probability density functions (pdfs); and FIG. 28A-28B show a non-limiting example of difference distributions of Bayesian posterior probability density functions of different test conditions, the difference distributions providing an index of acuity threshold change.

DETAILED DESCRIPTION OF THE INVENTION

Figure 1:
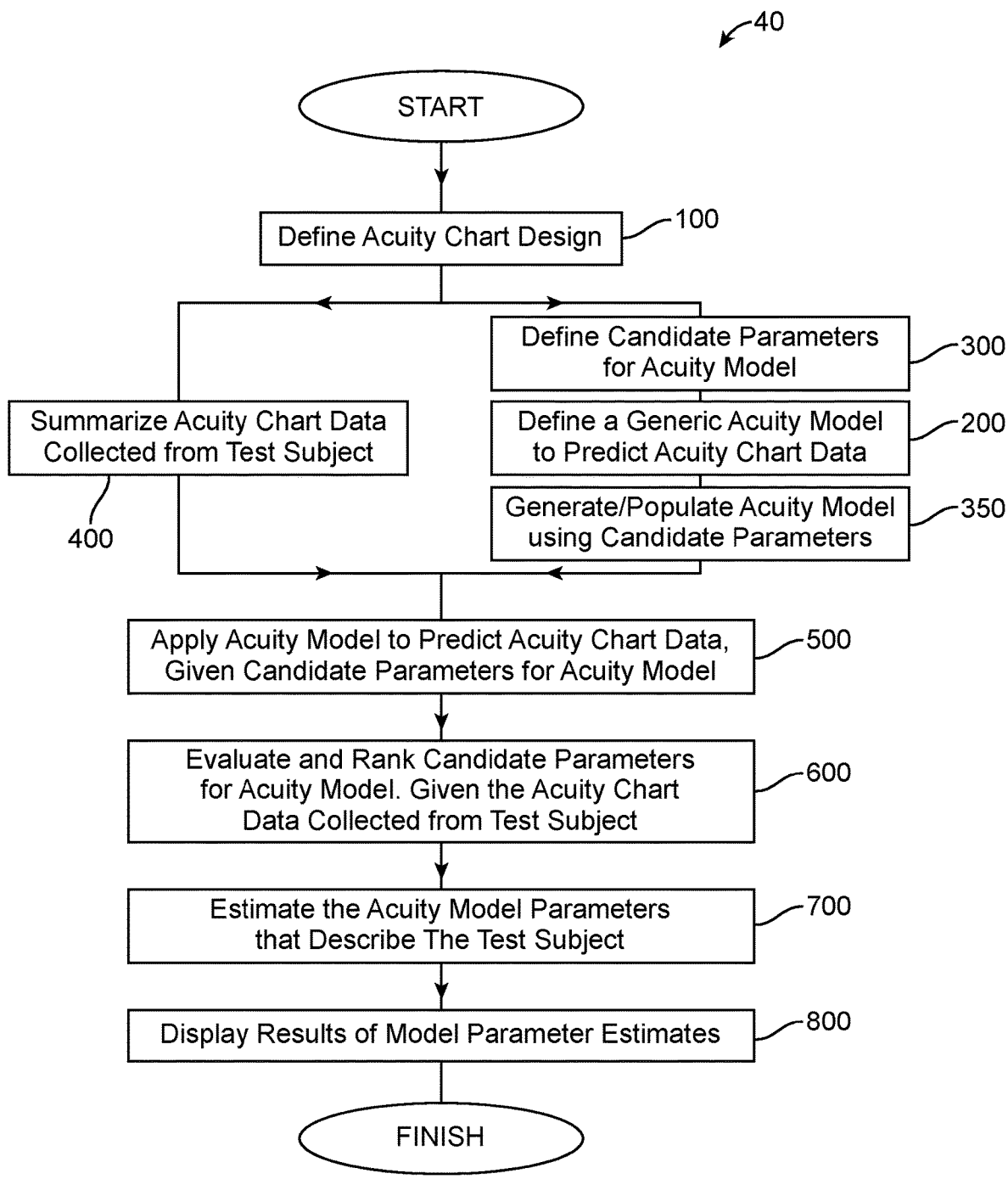
FIG. 1 shows a non-limiting example of a flow chart of a scoring algorithm S.

The methods, systems, and devices disclosed herein relates to visual acuity assessment using visual acuity tests.

The systems and methods disclosed herein can include a wide spectrum of advantages over existing acuity testing and analysis methods or systems. Unlike existing adaptive acuity testing methods that optimize optotype selection for only one letter at one size, the current systems and methods can enable optimization for the optotype ensemble presented on each test slide. The systems and methods disclosed herein may enable concurrent estimates of chart-specific and chart-invariant acuity parameters or metrics. Additional advantages associated with the methods and systems disclosed herein can include: a precise focus on each individual subject while adhering to chart design standards, fast testing time, comparable precision to time-consuming single-letter acuity tests, and visual acuity results independent of optotype sizes, test charts, or testing procedures. Both sets of acuity parameters, chart-specific and chart-invariant, herein are interchangeable and inter-translatable.

Disclosed herein, in some embodiments, is a computer-implemented method for generating an acuity model for scoring visual acuity of a subject, the method comprising: a) obtaining one or more acuity chart design parameters; b) collecting acuity test data of the subject; c) selecting a first set of chart-specific acuity parameters from one or more sets of candidate acuity parameters; d) generating an acuity model comprising: i) generating a single-optotype psychometric function, the single-optotype psychometric function comprising the first set of chart-specific acuity parameters; ii) calculating a family of multiple-optotype psychometric functions using the single-optotype psychometric function; and iii) generating a chart-specific psychometric function using the family of multiple-optotype psychometric functions, the chart-specific psychometric function comprising a second set of chart-specific acuity parameters, wherein the acuity model is configurable to estimate possibility of obtaining the acuity test data of the subject based on the one or more acuity chart design parameters. In some embodiments, the method further comprising, subsequent to (c) and prior to (i), generating a sensitivity-based psychometric function comprising a first set of chart-invariant sensitivity parameters, and wherein the first set of chart-invariant sensitivity parameters comprises a sensitivity threshold and a sensitivity range, and wherein the first set of chart-invariant sensitivity parameters are generated based on the first set of chart-specific acuity parameters. In some embodiments, the sensitivity-based psychometric function is independent of the one or more acuity chart design parameters. In some embodiments, the sensitivity-based psychometric function is generated based on the one or more acuity chart design parameters and/or one or more additional parameters of the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the method further comprises translating the sensitivity-based psychometric function to the single-optotype psychometric function, prior to (i). In some embodiments, the first set of chart-specific acuity parameters comprises an acuity threshold and an acuity range. In some embodiments, the single-optotype psychometric function is chart-specific. In some embodiments, the second set of chart-specific acuity parameters comprises an acuity threshold and an acuity range. In some embodiments, the first set or the second set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the first set or the second set of chart-specific acuity parameters comprises one or more numerical values. In some embodiments, the first set or the second set of chart-specific acuity parameters comprises at least one posterior probability density function for a parameter thereof. In some embodiments, the acuity test data of the subject comprises data from at least two different test conditions. In some embodiments, the first set or the second set of chart-specific acuity parameters comprises posterior probability density functions for an acuity threshold from the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, (iii) further comprising using a weighted sum of the family of multiple-optotype psychometric functions. In some embodiments, the weighting of the family of psychometric functions is based on the acuity chart data of the subject. In some embodiments, the weighting is determined manually by a user or automatically by a computer program. In some embodiments, (b) further comprising displaying one or more acuity charts generated based on the one or more acuity chart design parameters to the subject. In some embodiments, each of the one or more acuity charts comprises at least one optotype. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the one or more sets of candidate acuity parameters are generated based on the one or more acuity chart design parameters, the acuity test data of the subject, or both.

Disclosed herein, in some embodiments, is a computer-implemented method for scoring visual acuity of a subject, the method comprising: a) obtaining one or more acuity chart design parameters; b) collecting acuity test data of the subject; c) generating one or more sets of candidate acuity parameters based on the one or more acuity chart design parameters, the acuity test data of the subject, or both; d) generating an acuity model comprising generating one or more chart-specific psychometric functions, each chart-specific psychometric function comprising a set of chart-specific acuity parameters of the one or more sets of chart-specific acuity parameters; e) generating the probabilities of observing the acuity test data using the acuity model and the one or more sets of candidate acuity parameters; f) ranking the one or more sets of candidate acuity parameters for the subject based on the probabilities; and g) selecting one set from the one or more sets of candidate acuity parameters for the subject based on the rankings. In some embodiments, each set of the candidate acuity parameters comprises: an acuity threshold and an acuity range. In some embodiments, each set of the candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the candidate acuity parameters comprises a posterior probability density function for the one or more acuity parameters. In some embodiments, each set of the candidate acuity parameters comprises a posterior probability density function for each of the one or more acuity parameters. In some embodiments, (b) comprises summarizing acuity test data from the subject. In some embodiments, the method further comprises, subsequent to (g), displaying visual acuity test result to the subject or the user, the test result comprising the selected set of candidate acuity parameters. In some embodiments, the acuity test data of the subject comprises data from only a first test condition. In some embodiments, the acuity test data of the subject comprises data from a first and second test conditions. In some embodiments, the selected set of the candidate acuity parameters comprises a first posterior probability density function of an acuity threshold or an acuity range. In some embodiments, b) comprises selecting data with the first test condition. In some embodiments, the method further comprises, subsequent to g), selecting data with the second test condition from the acuity test data of the subject; and repeating c) to g). In some embodiments, the selected set of the candidate acuity parameters comprises a second posterior probability density function for the acuity threshold or the acuity range. In some embodiments, the method further comprises obtaining a difference distribution using the first and second posterior probability density functions. In some embodiments, the method comprises calculating a change in acuity threshold or acuity range between the first and the second test conditions based on the difference distribution. In some embodiments, the visual acuity test result is chart-invariant or chart-specific. In some embodiments, (e) is based on Bayes' theorem or maximum likelihood estimation. In some embodiments, the posterior probability density function is a Bayesian posterior probability density function. In some embodiments, the first or the second posterior probability density function is a Bayesian posterior probability density function. In some embodiments, (d) comprises: generating a single-optotype psychometric function, the single-optotype psychometric function comprising the first set of chart-specific acuity parameters; calculating a family of multiple-optotype psychometric functions using the single-optotype psychometric function; and generating a chart-specific psychometric function using the family of multiple-optotype psychometric functions, the chart-specific psychometric function comprising a second set of chart-specific acuity parameters. In some embodiments, the method further comprises, prior to generating the single-optotype psychometric function, generating a sensitivity-based psychometric function comprising a first set of chart-invariant sensitivity parameters. In some embodiments, the sensitivity-based psychometric function is independent of the one or more acuity chart design parameters. In some embodiments, the first set of chart-invariant sensitivity parameters comprises a sensitivity threshold and a sensitivity range, and wherein the first set of chart-invariant sensitivity parameters are generated based on the one or more sets of candidate acuity parameters. In some embodiments, the sensitivity-based psychometric function is generated based on the one or more acuity chart design parameters and/or one or more additional parameters of the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the method further comprises translating the sensitivity-based psychometric function to the single-optotype psychometric function. In some embodiments, the set of chart-specific acuity parameters comprises an acuity threshold and an acuity range. In some embodiments, the single-optotype psychometric function is chart-specific. In some embodiments, the set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the set of chart-specific acuity parameters comprises one or more numerical values. In some embodiments, the set of chart-specific acuity parameters comprises at least one posterior probability density function for a parameter thereof. In some embodiments, the acuity test data of the subject comprises data from at least two different test conditions. In some embodiments, the set of chart-specific acuity parameters comprises posterior probability density functions for an acuity threshold of the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, generating a chart-specific psychometric function further comprising using a weighted sum of the family of multiple-optotype psychometric functions. In some embodiments, the weighting of the family of psychometric functions is based on the acuity chart data of the subject. In some embodiments, the weighting is determined manually by a user or automatically by a computer program. In some embodiments, (b) further comprises displaying one or more acuity charts generated based on the one or more acuity chart design parameters to the subject. The method of claim 71, wherein each of the one or more acuity charts comprises at least one optotype. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the method further comprises: h) generating a plurality of candidate acuity charts based on the one or more chart design parameters; and i) selecting one or more of the plurality of candidate acuity charts for acuity testing of the subject based on the ranking of the plurality of candidate acuity charts, wherein the ranking is based on the selected set of candidate acuity parameters for the subjects. In some embodiments, the method further comprising, subsequent to (b); collecting data from the subject using the selected one or more candidate acuity charts; if a stopping criterion has not been met, repeating steps c) to g) and steps h) to i) in until the stopping criteria has been met.

Disclosed herein, in some embodiments, is a computer-implemented method for adaptively evaluating visual acuity of a subject, the method comprising: a) obtaining one or more acuity chart design parameters; b) collecting acuity test data of the subject; c) generating one or more sets of candidate acuity parameters based on one or more acuity chart design parameters and the acuity test data of the subject, each of the one or more sets of candidate acuity parameters comprises a rank obtained by analyzing the acuity test data of the subject; d) generating a plurality of candidate acuity charts based on the one or more acuity chart design parameters; e) ranking the plurality of candidate acuity charts based on the rank of each of the one or more sets of candidate acuity parameters; and f) selecting one or more acuity charts from the plurality of candidate acuity charts based on ranks thereof to be presented to the subject for acuity testing. In some embodiments, the method further comprises, subsequent to f), presenting the one or more selected acuity charts to the subject. In some embodiments, the method further comprises, subsequent to f) updating the acuity test data with new data collected from the subject using the one or more selected acuity charts. In some embodiments, the method further comprises repeating: presenting the one or more selected acuity charts to the subject; updating the acuity test data with new data collected from the subject using the one or more selected acuity charts; and steps b) to f); until a stopping criterion has been met. In some embodiments, each set of the one or more sets of candidate acuity parameters comprises: an acuity threshold and an acuity range. In some embodiments, each set of the one or more sets of candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the one or more sets of candidate acuity parameters comprises a posterior probability density function for the one or more acuity parameters. In some embodiments, each set of the one or more sets of candidate acuity parameters comprises a posterior probability density function for each of the one or more acuity parameters. In some embodiments, (b) comprises summarizing acuity test data from the subject. In some embodiments, the acuity test data of the subject comprises data from only a first test condition. In some embodiments, the acuity test data of the subject comprises data from a first and second test conditions. In some embodiments, each set of the one or more sets of candidate acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the acuity test data of the subject comprises data from at least two different test conditions. In some embodiments, each set of the one or more sets of candidate acuity parameters comprises posterior probability density function for an acuity threshold or an acuity range. In some embodiments, the one or more acuity chart design parameters comprises: a total number of optotypes, a number of optotypes per line, a method of optotype sampling, an optotype size, a number of lines, and a response of the subject, or a combination thereof. In some embodiments, each of the candidate acuity charts comprises at least one optotype. In some embodiments, one or more of candidate acuity charts are of a contrast that is about 25%, 2.5%, or 1.5% of a normal contrast in standard ETDRS charts or Sloane charts. The method of claim 90, wherein the at least one optotypes is a letter, a number, or a symbol.

Disclosed herein, in some embodiments, is a computer-implemented system for generating an acuity model for scoring visual acuity of a subject, the system comprising: a digital processing device comprising an operating system configured to perform executable instructions and a memory; and a computer program including instructions executable by the digital processing device to create a scoring application comprising a software module configured to: a) obtain one or more acuity chart design parameters; b) collect acuity test data of the subject; c) select a first set of chart-specific acuity parameter from one or more sets of candidate acuity parameters; d) generate an acuity model comprising: i. generate a single-optotype psychometric function, the single-optotype psychometric function comprising the first set of chart-specific acuity parameters; ii. calculate a family of multiple-optotype psychometric functions using the single-optotype psychometric function; and iii. generate a chart-specific psychometric function using the family of multiple-optotype psychometric functions, the chart-specific psychometric function comprising a second set of chart-specific acuity parameters, wherein the acuity model is configurable to estimate possibility of obtaining the acuity test data of the subject based on the one or more acuity chart design parameters. In some embodiments, the system further comprises, subsequent to (c) and prior to (i), generate a sensitivity-based psychometric function comprising a first set of chart-invariant sensitivity parameters, and wherein the first set of chart-invariant sensitivity parameters comprises a sensitivity threshold and a sensitivity range, and wherein the first set of chart-invariant sensitivity parameters are generated based on the first set of chart-specific acuity parameters. In some embodiments, the sensitivity-based psychometric function is independent of the one or more acuity chart design parameters. In some embodiments, the sensitivity-based psychometric function is generated based on the one or more acuity chart design parameters and/or one or more additional parameters of the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the system further comprises translate the sensitivity-based psychometric function to the single-optotype psychometric function, prior to (i). In some embodiments, the first set of chart-specific acuity parameters comprises an acuity threshold and an acuity range. In some embodiments, the single-optotype psychometric function is chart-specific. In some embodiments, the second set of chart-specific acuity parameters comprises an acuity threshold and an acuity range. In some embodiments, the first set or the second set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the first set or the second set of chart-specific acuity parameters comprises one or more numerical values. In some embodiments, the first set or the second set of chart-specific acuity parameters comprises at least one posterior probability density function for a parameter thereof. In some embodiments, the acuity test data of the subject comprises data from at least two different test conditions. In some embodiments, the first set or the second set of chart-specific acuity parameters comprises posterior probability density functions for an acuity threshold from the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, (iii) further comprises using a weighted sum of the family of multiple-optotype psychometric functions. In some embodiments, the weighting of the family of psychometric functions is based on the acuity chart data of the subject. In some embodiments, the weighting is determined manually by a user or automatically by a computer program. In some embodiments, (b) further comprising use one or more acuity charts generated based on the one or more acuity chart design parameters. In some embodiments, each of the one or more acuity charts comprises at least one optotype. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the one or more sets of candidate acuity parameters are generated based on the one or more acuity chart design parameters, the acuity test data of the subject, or both.

Disclosed herein, in some embodiments, is a computer system for generating an acuity model for scoring visual acuity of a subject, the system comprising: a digital processing device comprising an operating system configured to perform executable instructions and a memory; and a computer program including instructions executable by the digital processing device to create a scoring application comprising a software module configured to: a) obtain one or more acuity chart design parameters; b) collect acuity test data of the subject; c) generate one or more sets of candidate acuity parameters based on the one or more acuity chart design parameters, the acuity test data of the subject, or both; d) generate an acuity model comprising generating one or more chart-specific psychometric functions, each chart-specific psychometric function comprising a set of chart-specific acuity parameters of the one or more sets of chart-specific acuity parameters, e) generate the probabilities of observing the acuity test data using the acuity model and the one or more sets of candidate acuity parameters; f) rank the one or more sets of candidate acuity parameters for the subject based on the probabilities; and g) select one set from the one or more sets of candidate acuity parameters for the subject based on the rankings. In some embodiments, each set of the candidate acuity parameters comprises: an acuity threshold and an acuity range. In some embodiments, each set of the candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the candidate acuity parameters comprises a posterior probability density function for the one or more acuity parameters. In some embodiments, each set of the candidate acuity parameters comprises a posterior probability density function for each of the one or more acuity parameters. In some embodiments, (b) comprises summarize acuity test data from the subject. In some embodiments, the system further comprises, subsequent to (g), display visual acuity test result to the subject or the user, the result comprising the selected set of candidate acuity parameters. In some embodiments, the acuity test data of the subject comprises data from only a first test condition. In some embodiments, the acuity test data of the subject comprises data from a first and second test conditions. In some embodiments, the selected set of the candidate acuity parameters comprises a first posterior probability density function of an acuity threshold or an acuity range. In some embodiments, b) comprises select data with the first test condition. In some embodiments, the system further comprises, subsequent to g), select data with the second test condition from the acuity test data of the subject; and repeat c) to g). In some embodiments, the selected set of the candidate acuity parameters comprises a second posterior probability density function for the acuity threshold or the acuity range. In some embodiments, the system further comprises obtain a difference distribution using the first and second posterior probability density functions. In some embodiments, the system further comprises calculate a change in acuity threshold or acuity range between the first and the second test conditions based on the difference distribution. In some embodiments, the visual acuity test result is chart-invariant or chart-specific. In some embodiments, (e) is based on Bayes' theorem or maximum likelihood estimation. In some embodiments, the posterior probability density function is a Bayesian posterior probability density function. In some embodiments, the first or the second posterior probability density function is a Bayesian posterior probability density function. In some embodiments, (d) comprises: generating a single-optotype psychometric function, the single-optotype psychometric function comprising the first set of chart-specific acuity parameters; calculating a family of multiple-optotype psychometric functions using the single-optotype psychometric function; and generating a chart-specific psychometric function using the family of multiple-optotype psychometric functions, the chart-specific psychometric function comprising a second set of chart-specific acuity parameters. In some embodiments, the system further comprises prior to generating the single-optotype psychometric function, generate a sensitivity-based psychometric function comprising a first set of chart-invariant sensitivity parameters. In some embodiments, the sensitivity-based psychometric function is independent of the one or more acuity chart design parameters. In some embodiments, the first set of chart-invariant sensitivity parameters comprises a sensitivity threshold and a sensitivity range. In some embodiments, the sensitivity-based psychometric function is generated based on the one or more acuity chart design parameters and/or one or more additional parameters that are based on the subject, the one or more additional parameters being chart-invariant. In some embodiments, the sensitivity-based psychometric function is generated based on signal detection theory. In some embodiments, the sensitivity-based psychometric function is configured to describe visual acuity performance of the subject as a d' function of one or more optotype sizes and independent of the one or more chart design parameters. In some embodiments, the system further comprises translate the sensitivity-based psychometric function to the single-optotype psychometric function. In some embodiments, the set of chart-specific acuity parameters comprises an acuity threshold and an acuity range. In some embodiments, the single-optotype psychometric function is chart-specific. In some embodiments, the set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the set of chart-specific acuity parameters comprises one or more numerical values. In some embodiments, the set of chart-specific acuity parameters comprises at least one posterior probability density function for a parameter thereof. In some embodiments, the acuity test data of the subject comprises data from at least two different test conditions. In some embodiments, the set of chart-specific acuity parameters comprises posterior probability density functions for an acuity threshold at the at least two different test conditions. In some embodiments, the one or more acuity chart design parameters comprises: a total number of optotypes, a number of optotypes per line, a method of optotype sampling, an optotype size, a number of lines, and a response of the subject, or a combination thereof. In some embodiments, the single-optotype psychometric function is based on at least one optotype size. In some embodiments, each function of the family of multiple-optotype psychometric functions is based on two or more different optotype sizes. In some embodiments, the single-optotype psychometric function comprises an acuity threshold and an acuity range of the subject. In some embodiments, one or more functions in the family of multiple-optotype psychometric functions are based on a number of optotypes per line in an acuity chart or subchart. In some embodiments, generating a chart-specific psychometric function further comprising using a weighted sum of the family of multiple-optotype psychometric functions. In some embodiments, the weighted sum of the family of psychometric functions is based on the acuity chart data of the subject. In some embodiments, the weighting is determined manually by a user or automatically by a computer program. In some embodiments, (b) further comprising displaying one or more acuity charts generated based on the one or more acuity chart design parameters. In some embodiments, each of the one or more acuity charts comprises at least one optotype. In some embodiments, the one or more acuity charts are of a contrast that is about 25%, 2.5%, or 1.5% of a normal contrast in standard ETDRS charts or Sloane charts. In some embodiments, the at least one optotypes is a letter, a number, or a symbol. In some embodiments, the system further comprises: h) generate a plurality of candidate acuity charts based on the one or more chart design parameters; and i) select one or more of the plurality of candidate acuity charts for acuity testing of the subject based on the ranking of the plurality of candidate acuity charts, wherein the ranking is based on the selected set of candidate acuity parameters for the subjects. In some embodiments, the system further comprises, subsequent to (b); collecting data from the subject using the selected one or more candidate acuity charts; if a stopping criterion has not been met, repeating steps c) to g) and steps h) to i) until the stopping criteria has been met.

Disclosed herein, in some embodiments, is a computer-implemented system for adaptively evaluating visual acuity of a subject, the system comprising: a digital processing device comprising an operating system configured to perform executable instructions and a memory; and a computer program including instructions executable by the digital processing device to create a scoring application comprising a software module configured for: a) obtaining one or more acuity chart design parameters; b) collecting acuity test data of the subject; c) generating one or more sets of candidate acuity parameters based on one or more acuity chart design parameters and the acuity test data of the subject, each of the one or more sets of candidate acuity parameters comprises a rank obtained by analyzing the acuity test data of the subject; d) generating a plurality of candidate acuity charts based on the one or more acuity chart design parameters; e) ranking the plurality of candidate acuity charts based on the rank of each of the one or more sets of candidate acuity parameters; and f) selecting one or more acuity charts from the plurality of candidate acuity charts based on ranks thereof to be presented to the subject for acuity testing. In some embodiments, the system further comprises, subsequent to f), present the one or more selected acuity charts to the subject. In some embodiments, the system further comprising, subsequent to f), update the acuity test data with new data collected from the subject using the one or more selected acuity charts. In some embodiments, the system further comprises repeat: present the one or more selected acuity charts to the subject; update the acuity test data with new data collected from the subject using the one or more selected acuity charts, and steps b) to f); until a stopping criterion has been met. In some embodiments, each set of the one or more sets of candidate acuity parameters comprises: an acuity threshold and an acuity range. In some embodiments, each set of the one or more sets of candidate acuity parameters comprises: an acuity threshold, an acuity range, an acuity slope, a change in the acuity threshold between two test conditions, the change in the acuity range between two test conditions, the change in the acuity slope between two test conditions, or a combination thereof. In some embodiments, each set of the one or more sets of candidate acuity parameters comprises a posterior probability density function for the one or more acuity parameters. In some embodiments, each set of the one or more sets of candidate acuity parameters comprises a posterior probability density function for each of the one or more acuity parameters. In some embodiments, (b) comprises summarize acuity test data from the subject. In some embodiments, the acuity test data of the subject comprises data from only a first test condition. In some embodiments, the acuity test data of the subject comprises data from a first and second test conditions. In some embodiments, each set of the one or more sets of candidate acuity parameters comprises an acuity threshold, an acuity range, an acuity slope, a change in the acuity threshold between two test conditions, the change in the acuity range between two test conditions, the change in the acuity slope between two test conditions, or a combination thereof. In some embodiments, the acuity test data of the subject comprises data from at least two different test conditions. In some embodiments, each set of the one or more sets of candidate acuity parameters comprises posterior probability density function for an acuity threshold or an acuity range. In some embodiments, the one or more acuity chart design parameters comprises: a total number of optotypes, a number of optotypes per line, a method of optotype sampling, an optotype size, a number of lines, and a response of the subject, or a combination thereof. In some embodiments, each of the candidate acuity charts comprises at least one optotype. In some embodiments, one or more of candidate acuity charts are of a contrast that is about 25%, 2.5%, or 1.5% of a normal contrast in standard ETDRS charts or Sloane charts. In some embodiments, the at least one optotypes is a letter, a number, or a symbol.

Optotypes

In some embodiments, an optotype is a standardized symbol for testing vision or visual acuity. In some embodiments, visual acuity chart or vision testing follows standards from one or more selected from the list of: American National Standards Institute, National Academy of Science, National Research Council, American Academy of Ophthalmology, the National Eye Institute, and American Academy of Optometry, and U.S. Food and Drug Administration.

In some embodiments, an optotype is any shaped letter, figure, number, photograph, or geometric symbol. In some embodiments, an optotype is of a pre-determined size. In some embodiments, the smallest size of optotype is to generate a visual acuity of −0.3 log MAR. In some embodiments, the smallest size of optotype is to generate a visual acuity of −0.25, −0.35, −0.4, −0.45, −0.5 log MAR. In some embodiments, the greatest size of optotype is to generate a visual acuity of 1.2, 1.25, 1.3, 1.35, 1.4, 1.45, 1.5, or 1.55 log MAR.

Visual Acuity Charts and Subcharts

In some embodiments, a visual acuity chart, (or interchangeably as "chart," "acuity chart," or "visual chart" herein) is used to measure the spatial resolution of the visual system of a subject. In some embodiments, a visual subchart is a portion or a part of a full visual chart. In some embodiments, a visual chart is an eye chart, a visual test chart, or a vision test chart, or the like. In some embodiments, a visual chart or subchart include one or more optotypes. In some embodiments, visual chart are classified under different types depending on at least one chart parameter or vision testing parameter. These parameters may include one or more selected from: type of optotypes, number of optotypes, number of rows, number of columns, optotype sizes, optotype size differences in adjacent rows or columns, number of test charts in a visual test, optotype sampling methods, or the like. In some embodiments, a visual chart is a ETDRS (Early Treatment Diabetic Retinopathy Study) log MAR (the x-axis and y-axis are the logarithm of the minimum angle of resolution) chart, Snellen chart, tumbling E chart, Landolt C chart, Lea test, or the Jaeger chart.

In some embodiments, a visual chart or subchart include one or more optotypes. In some embodiments, at least one optotype forms a visual test chart or subchart. In some embodiments, at least one row of optotypes, each row including at least one optotype, forms a visual test chart or subchart. In some embodiments, at least one column of optotypes, each column including at least one optotype, forms a visual test chart or subchart. In some embodiments, different optotypes of each row is of identical optotype size. In some embodiments, optotypes size decreases monotonically from the first row to the last row of the visual chart or visual subchart. In some embodiments, the number of optotypes in each row of the visual chart or subchart is identical. In some embodiments, each row has 5 optotypes. In some embodiments, the number of optotypes in each row of the visual chart or subchart is in the range of 1 to 5 optotypes. In some embodiments, a chart or a subchart has 3 rows of optotypes. In some embodiments, a chart or a subchart has 1 to 5 rows of optotypes. In some embodiments, a full visual chart has 14 rows of optotypes.

In some embodiments, the optotype size of each row is designated as the logarithm to the base 10 of decimal visual acuity. As an example, the decimal acuity of 1 is 0.00 in Log MAR acuity and the decimal acuity of 0.1 is 1.0 in Log MAR acuity.

Acuity Chart Design

In some embodiments, the methods, systems, or devices disclosed herein include an acuity chart and a subchart. In some embodiments, the acuity chart or subchart is constraint by one or more specific chart design features and/or design features of the optotypes.

In some embodiments, the design features of the optotypes, in addition to the design features of the acuity chart (or subchart) used to present the optotypes are considered in the systems and methods disclosed herein. In further embodiments, parameters (interchangeable as features) of optotypes and/or the charts in which they are presented, include but is not limited to:
  i. the number of possible optotype sizes (e.g., 11 optotype sizes for a Snellen chart and 14 sizes for ETDRS chart);
  ii. the possible sizes of optotypes (e.g. FIGS. 11A-11F)
  ii. the identity of optotypes:
    1. Letters
    2. Numbers
    3. Patterns
    4. Landolt C
    5. Tumbling E;
  iii. the size of the pool for sampling optotypes
    1. 10 for Sloan, Bailey-Lovie
    2. 4 for Landolt C, Tumbling E, HOTV, Lea, Hands
    3. 9 for traditional Snellen
    4. 12 for British Snellen standards BS 4274-1:2003;
    5. 26 for English alphabet
  iv. the method for sampling the pool of optotypes (e.g., with or without replacement);
  v. the number of lines presented in the chart, sub-chart, or series of sub-charts;
  vi. the number of optotypes presented per line;
  vii. the definition of the acuity metric (e.g., acuity threshold, acuity range, and/or acuity slope);

The existing arts in clinical care have focused on the nominal goal of the acuity test: determining the row of optotypes at which the patient fails to reliably identify optotypes at some pre-specified criterion: for example, the optotype size at which they cannot identify at least 2 of 5 optotypes. Current testing ignores several design factors that contribute to visual performance across different chart designs. For example, a small pool of optotypes makes it easier to guess correctly, even with no visual information. Specifically, when testing acuity with Landolt C optotypes (identifying one of four potential orientations), it is easier to guess correctly (25% chance), relative to acuity charts that have lower guessing rates (e.g., 10% for the Sloan set). Currently, acuity results are not qualified or corrected for the guessing-rates on different charts. There can be a confound of the contribution to performance that comes from chart-specific design factors, and the contribution to performance of patient-specific factors.

In some embodiments, disclosed herein includes a comprehensive consideration of one or more of the acuity chart design features, including chart-specific parameters and subject-specific (equivalent to chart-invariant parameters herein) parameters, which forms the foundation of the acuity model or predictive model herein. By using acuity chart design to finely define the contributions to performance, and accounting for different contributions to performance on each chart, the model may enable a measure of acuity performance of a subject that is independent of the chart used to collect the acuity data.

In some embodiments, visual acuity tests conform to design principles based on committee standards and/or historical and cultural preferences. Referring to FIG. 2A, in a particular embodiment, the design of the visual acuity chart recommended by the ETDRS committee comprises fourteen lines of optotypes, five optotypes per line, with a logarithmic reduction in size with each descending row. The 0.10 decimal log unit progression provides about 25% reduction in size with each successive row of optotypes. Each row comprises five letters that are sampled from the 10-letter Sloan set without replacement. In this embodiment, a visual acuity chart that satisfies the ETDRS standard is shown in FIG. 2A.

In some embodiments, the Snellen chart (FIG. 2B), which presents more letters at smaller optotype sizes and fewer letters at larger optotype sizes, remains the dominant chart used in clinical practice. In some embodiments, ETDRS, Snellen and similar standard-constrained chart designs relate to the static range and resolution for sampling optotype size. Due to a non-adaptive, deterministic testing routine, all subjects are presented with the same range of optotypes. Furthermore, the invariant sampling resolution of the test results in insensitivity to measuring acuity values that correspond to optotype sizes that are intermediate to those presented on the fourteen established optotype sizes.

In some embodiments, visual acuity charts may conform to design principles that are dictated by standards committees and/or historical preferences. For example, the ETDRS chart is the visual acuity chart recommended for clinical trials and clinical research (FIG. 2A). The design of the ETDRS chart comprises fourteen lines of optotypes, with each line presenting five optotypes sampled without replacement from the 10-letter Sloan set, and a constant logarithmic progression of optotype size between lines. The 0.10 decimal log unit progression corresponds to an approximately 25% increase in size from each line to the one above it.

The design of the Snellen acuity chart (FIG. 2B) comprises twelve lines that exhibit different numbers of optotypes per line, and different size progressions between lines. Despite design features considered to be inferior to those of the ETDRS chart, the Snellen chart remains the dominant acuity chart design used in clinical practice for eye care specialists and general practitioners.

In some embodiments, to improve the sampling resolution for optotype size in visual acuity tests, while strictly conforming to visual acuity design standards and principles, a method for producing an expansive library of visual acuity charts is used. Referring to FIG. 10, in a particular embodiment, the topmost pattern 1001 represents the sampling scheme represented by ETDRS standard chart, which presents fourteen standard sizes of optotypes from −0.3 to 1.0 log MAR, with 0.10 log unit sampling resolution between successive sizes. The anchor point 1002 of 0.35 represents the mean optotype size of the ETDRS standard chart. In some embodiments, changing the anchor point 1002 of a standard-constrained chart is used to produce a larger, complementary set of acuity charts that improve the aggregate resolution for sampling optotype size, while preserving the adherence to acuity chart standards. In this particular embodiment, a set of ten acuity charts, produced by changing the anchor point of a standard chart within the range of 0.3-0.4 log MAR, with an anchor point resolution of 0.01 log MAR, is generated 1003. In some embodiments, each test slide uses the same sampling resolution as the ETDRS standard. However, when the set of design-constrained charts is considered in aggregate, these charts provide the fine resolution of optotype size represented by the bottom-most pattern, which is ten times finer than the ETDRS standard resolution. In this embodiment, taken together, the set of 10 charts is developed to evaluate vision over a wide range of 141 different optotype sizes, with 0.01 log unit resolution.

In some embodiments, for a standard ETDRS chart that follows the design principle of log-linear line-by-line progression of optotype size, "anchor point" is the optotype size that corresponds to the mean (or median) log MAR size of the fourteen optotype sizes that comprise the full chart. In the case of the ETDRS chart, the anchor point corresponds to an optotype size between the 20/40 and 20/50 lines (in Snellen notation).

Referring to FIGS. 11A-11F, in some embodiments, exemplary subsets of design-constrained visual acuity charts are shown. In these embodiments, acuity charts are produced using ETDRS design principles (FIGS. 11A-11C) with three different anchor points, i.e., 0.30, 0.35, and 0.40 log MAR, and Snellen design principles (FIGS. 11D-11F) with three different anchor points, i.e., 0.30, 0.35, and 0.40 log MAR. In these embodiments, the acuity chart can optionally have a fixed or a variable number of optotypes per row.

Figures 12A, 12B, 12C:
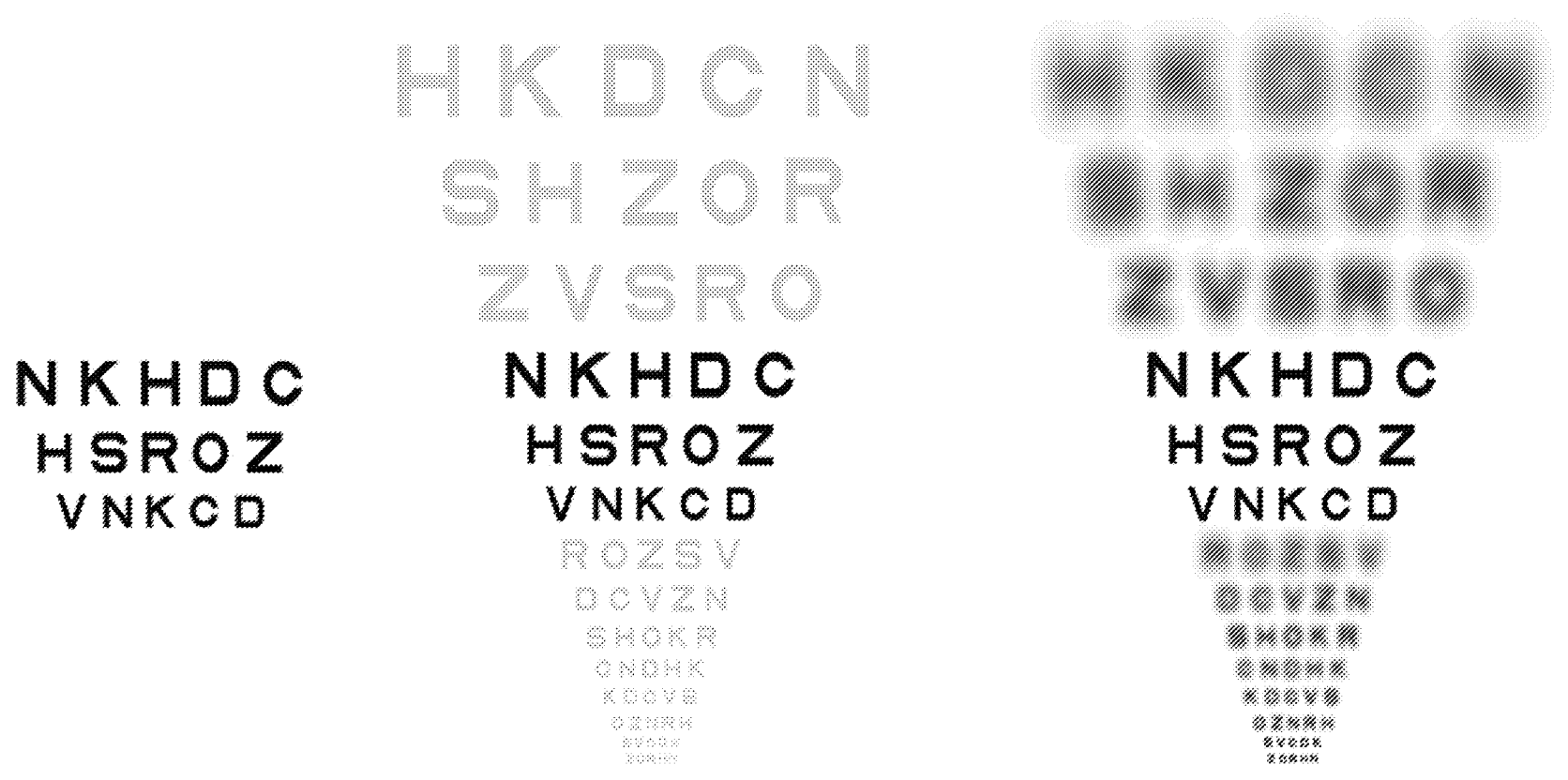

Referring to FIGS. 12A-12C, in some particular embodiments, a test slide is focused to specific regions of a full standard-constrained adaptive testing chart. A full design-constrained acuity chart is sub-sampled by presenting only a restricted set of optotypes from a full acuity chart, which is in turn a subsample of the greater library of design-constrained charts. Rather than present the full 14 rows of the ETDRS chart as in FIG. 2A, presenting a set of subcharts focus vision testing to a spatial subsample of the full chart (e.g., 3 rows of optotypes). The target letters of the focused visual acuity test are distinguished by presenting only the sub-sampled region of the full chart (FIG. 12A), presenting the sub-sampled region at a high contrast (FIG. 12B), relative to the low contrast of the rest of the chart, or presenting only the sub-sampled region without blur (FIG. 12C), and blurring the rest of the chart.

In the current art, the analysis of acuity chart testing is based on heuristics (line-assignment or letter-by-letter) that yield results that are imprecise and difficult to coordinate across different charts.

In some embodiments, the disclosed systems or methods herein provide a common statistical and computational framework for the precise testing of visual acuity, and its changes, measured with the ETDRS, Snellen, or chart of any design.

Figures 13A, 13B, 13C:
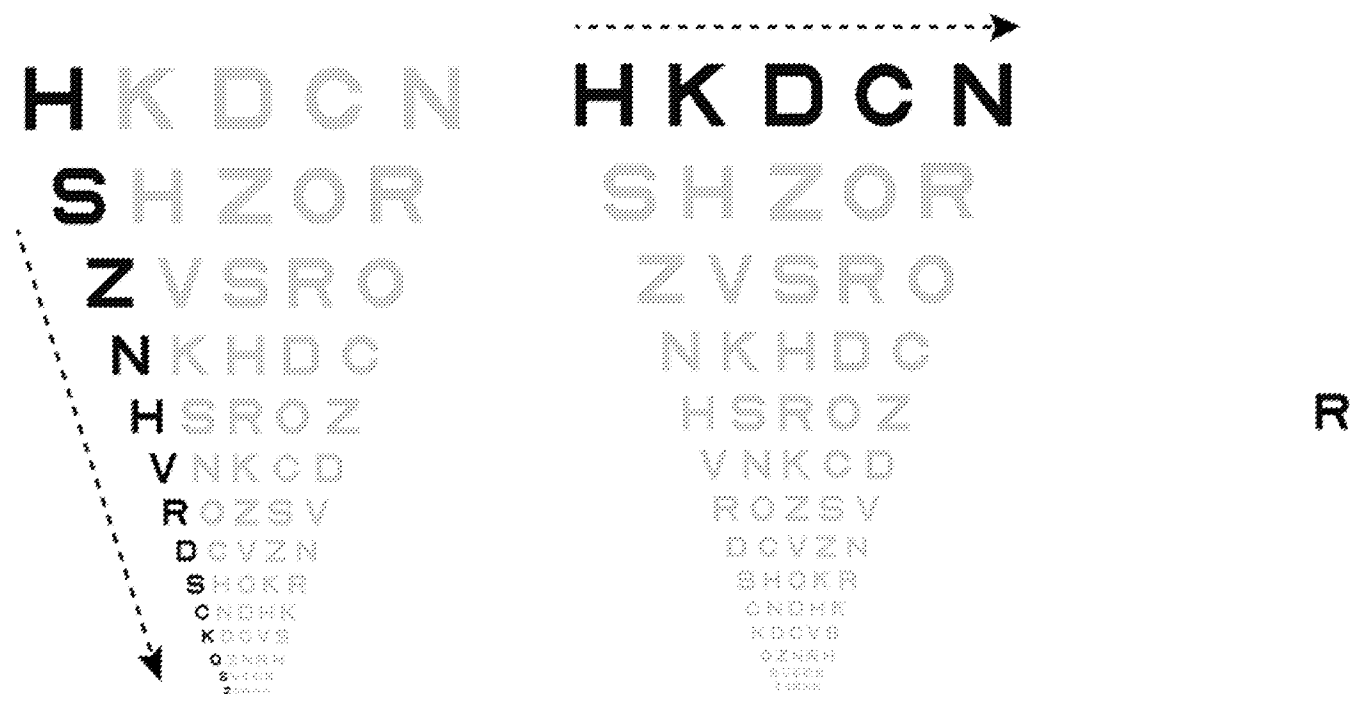

In some embodiments, for visual acuity testing, the presentation of a test slide to a subject is followed by a response from the subject. In some embodiments, the response from the subject may include identification of one or more optotypes and/or identification of one or more features of the optotype(s). Referring to FIGS. 13A-13C, in some embodiments, a subject reads down the first column in a response until instructed to stop (FIG. 13A). In some embodiments, a subject reads at least a line across in a response until instructed to stop (FIG. 13B). In some embodiments, a subject reads a single letter presented (FIG. 13C). In some embodiments, optotypes are either solid black or gray. In some embodiments, gray optotypes indicate lower prioritization than solid black optotypes.

In some embodiments, to improve the precision of visual acuity testing, a library of visual acuity charts is generated that exhibits high precision for sampling optotype size. Individually, these charts have the similar sampling precision for sampling optotype size as the existing acuity charts, and their appearance conforms to the design principles recommended by standards committees for visual acuity charts (e.g., ANSI, ISO, NSC/NAS). Collectively, however, this expansive library can exhibit finer-grain resolution for sampling optotype size than the existing acuity charts (see FIGS. 2A and 15). This library, or similar libraries, may comprise a wide range of design features for optotype slides that includes, but is not limited to: (1) slides with many lines that match the full ETDRS and Snellen charts; (2) slides that subsample the full ETDRS chart, and only present 1-5 lines at one time; and (3) slides with single optotypes. Likewise, the library may also include the high-precision family of charts motivated by the Snellen design.

In some embodiments, the optotypes are sampled randomly from a library of optotypes. In some embodiments, the optotypes are sampled adaptively from a library of optotypes. In some embodiments, the adaptively sampling of optotypes is based on a priori information of the subject's visual acuity. In some embodiments, the adaptive sampling is based on estimated visual sensitivity parameters from a previous test run, i.e., visual acuity threshold and/or acuity range and/or acuity slope. In other embodiments, the adaptive sampling is based on results of a previous test, medical records of the patient, subject's responses in a previous test or a test run. In some embodiments, adaptive sampling is to optimize optotype sizes for fast and accurate acuity parameter estimation. For example, if on the first test chart, subject A identifies all 3 rows with 5 optotypes on each row correctly, and subject B correctly identifies 5, 4, 4 optotypes on each row, respectively, subject A is presented with optotypes whose average size is smaller than the optotypes presented to subject B in the second test chart.

In some embodiments, the visual acuity charts and/or subcharts provides a resolution that is 2, 3, 4, 5, 6, 7, 8, 9, 10, 11, 12, 13, 14, 15, 16, 17, 18, 19, or 20 times higher than the existing standard resolution of acuity charts, e.g., ETDRS standard resolution.

In some embodiments, the Snellen chart remains the dominant acuity test in clinical practice, but the ETDRS chart serves as the standard for ophthalmic space clinical research and clinical trials. The ETDRS chart can present optotypes in fourteen lines (see FIG. 2A): a smallest optotype size of log MAR=−0.3, a largest optotype size of 1.0, and intermediate sizes spaced with a constant log-linear progression of size (e.g., 0.10 log unit). These design principles can be dictated by standards committees. One shortcoming of these existing chart designs is the inflexibility of static, pre-determined, non-adaptive testing. Testing all patients the same way—using the limited number of optotype sizes available on a single chart—can make it difficult to precisely assess the broad range of vision in the population (from healthy to impaired vision). To improve the flexibility and precision of vision testing, and better adapted testing to different levels of healthy and impaired vision, the current art has moved towards computerized acuity testing with digital displays. Currently, adaptive testing algorithms focus on changing the optotype size of a single letter, based on correct and incorrect responses. These existing algorithms use simple heuristics that are limited to single letter outcomes, and not on the more complicated multiple-letter response outcomes.

The design features of different acuity tests can be dictated by external or internal guidelines or design principles. External guidelines can reflect recommendations issued by ANSI or ISO committees, and internal guidelines can reflect corporate or cultural preferences. External guidelines can be seen as mandates and internal guidelines can be seen as preferences. Both types of guidelines constrain the appearance and implementation of acuity tests. Currently, single-letter acuity testing does not conform to the design principles and guidelines recommended by ANSI and ISO committees. As an example, consider the standard ETDRS chart with an anchor point of 0.35 log MAR, and consider the set of acuity charts generated by the ten other anchor points that range from 0.3 to 0.4 log MAR inclusive, with 0.01 log unit resolution. (Finer and finer resolutions for sampling anchor points are possible, but the benefits of finer resolution are eventually limited by the printing resolution of paper charts or pixel resolution of digital displays). Generating these 10 charts (in addition to the ETDRS standard), which each comprise fourteen optotype sizes, provides precise coverage of 141 distinct optotype sizes that span from −0.4 to 1.1 log MAR. Due to the chart design standard of 0.10 log unit progression between lines on the same chart, the full set of optotype sizes represented by these complementary charts can be represented subsets of optotype sizes that are linearly intercalated in log-space.

In some embodiments, developing acuity charts that adhere to the design constraints of ETDRS charts, but with different anchor points, yields a library of novel charts with a much larger set of optotype sizes, relative to the standard ETDRS chart (see FIG. 2A). Defined to meet ETDRS chart design standards, the novel charts may largely appear to be the same as the originals, yet yield improved range and resolution for sampling different optotype sizes. In some embodiments, a different anchor point results in slightly different maximum and minimum sizes (FIGS. 11A-11C), though the standard-constrained size progression between adjacent rows is maintained. Similarly, a library of novel charts with a much larger set of optotype sizes, relative to the standard Snellen chart, can be generated.

Using a set of anchor points (e.g. anchor points that are not limited by existing acuity charts) can generate an alternative set of standard-constrained charts that provide more flexible sampling resolution for optotype size. Considering subcharts of fewer lines can expand the library of full fourteen-line visual acuity charts still further. These libraries of visual acuity charts can be generated via chart subsampling (e.g., only 1-5 rows can be presented at one time). Spatial subsampling of the full chart can focus on a subset of the chart, for example, 1-5 lines of optotypes rather than the full 14 chart lines. In some embodiments, the top and/or bottom of the charts represent relatively uninformative regions that can be avoided during testing. Testing on these lines may result in the correct report of all optotypes, or none. Better sampling of the full chart can involve optotype sizes that have different possible intermediate outcomes, e.g., of 2, 3, or 4 optotypes out of 5 correct. The complementary chart sets may represent a stimulus set that can be sampled once, or repeatedly via deterministically, randomized, and/or optimized sampling. A sampling of a standard ETDRS visual acuity chart is presented in FIGS. 11A-11C. The size progression between lines is constant in log space. The anchor point of these sizes can be selected as the mean in log space. In this embodiment, seven sizes are larger and seven sizes are smaller than the selected anchor point.

In some embodiments, the libraries of charts disclosed herein exhibit design features that provide combinations of optotype sizes that greatly expand on the limited set of fourteen sizes used by the ETDRS standard chart. A different library may be generated specifically for each chart and its design principles (e.g., ETDRS, Snellen, HOTV, Lea Symbols, et cetera).

In the prior art, despite the emerging use of the ETDRS in clinical research and clinical trials, the Snellen chart has remained the dominant acuity test in clinical practice for 150 years. By practical necessity, the method for calculating acuity metrics has relied on mental scoring heuristics that are explicitly connected to the letters and design principles apparent to the test practitioner. The two dominant approaches for estimating acuity are line-by-line assignment or letter-by-letter. For example, in Snellen acuity testing, the line-assignment method calculates the final acuity estimate as the optotype size corresponding to the last line on which the patient correctly reports 3 of 5 optotypes. To compare with line-assignment, the ETDRS chart has used letter-by-letter scoring in which each correctly reported letter is credited with 0.02 log MAR units.

Unlike the prior art, which only considers a single psychometric function that defines the probability of correctly identifying a single optotype as a function of its size (sometimes also known as the "frequency-of-seeing curve), the method and system herein includes analysis of the responses to estimate acuity by considering a family of psychometric functions that defines the probability of observing the full complement of correct response combinations for multiple optotypes, as a function of optotype size (see FIGS. 4-9). In the example of the ETDRS chart that presents five optotypes for each line, there are six complementary psychometric functions that describe the probability of observing the correct report of 0, 1, 2, 3, 4, or 5 optotypes out of the five presented in total (FIGS. 6B, 8B). Using the prior art, measuring six psychometric functions only multiplies the problem of measuring a single psychometric function. The practical limitations on clinical testing time likewise make it impossible to use the prior art to estimate acuity metrics using these six empirically observed psychometric functions that are chart-specific.

Acuity Parameters

Visual acuity can be acuteness or clearness or resolution of vision. In some embodiments, the visual acuity is represented by at least one psychometric function. In some embodiments, the visual acuity is represented by at least one psychometric function, implicit or explicit. In some embodiments, the psychometric function is chart-specific or chart-invariant. In some embodiments, the visual acuity is represented by at least one sensitivity (d') psychometric function. In signal detection theory, sensitivity (d') parameters may represent behavioral performance that is independent of task-based factors that affect response bias or decision criteria. In some embodiments, sensitivity parameters in acuity testing determine visual performance that is independent of the specific design features that are used for visual acuity testing. In some embodiments, a psychometric function is uniquely defined by at least two acuity parameters. In some embodiments, the two acuity parameters form a two-dimensional parameter space. In some embodiments, the visual acuity is represented by at least one single-optotype psychometric function and/or multiple-optotype psychometric functions.

In some embodiments, visual acuity is determined or measured using at least one acuity parameter. Disclosed herein, an acuity parameter is interchangeable with an acuity model parameter, or an acuity metric. In some embodiments, an acuity parameter is an acuity threshold. In some embodiments, an acuity parameter is an acuity range. In some embodiments, an acuity parameter is an acuity slope. In some embodiments, visual acuity is determined or measured using two acuity parameters. In some embodiments, two acuity parameters are the acuity threshold and the acuity range. In some embodiments, two acuity parameters are the acuity threshold and the acuity slope.

In some embodiments, the acuity parameter herein includes a probability density function, a cumulative probability density function, or probability distribution function of an acuity threshold, acuity range, acuity slope, sensitivity threshold, sensitivity range, sensitivity slope, or a combination thereof. In some embodiments, the acuity parameter herein includes a probability density function, a cumulative probability density function, or probability distribution function of a change in acuity threshold, acuity range, acuity slope, sensitivity threshold, sensitivity range, sensitivity slope, or a combination thereof, between two different test conditions. In some embodiments, the probability distribution function and the probability density function are interchangeable herein.

For example, the acuity threshold can include a probability density function (pdf) over different optotype sizes, the pdf comprising the probability of different optotype sizes being just detectable to a subject. In some embodiments, the acuity threshold includes a range of different optotype sizes, the range includes optotype sizes that are just detectable to a subject. In some embodiments, the acuity threshold includes an optotype size value and a size variation, the optotype size is the smallest detectable size to a subject.

In some embodiments, the acuity parameter herein includes a sensitivity (d') threshold, which is configured to provide a performance criterion in vision similarly as the acuity threshold. The acuity threshold determined by the chart-invariant psychometric function may be a sensitivity (d')-based threshold. In some embodiments, the acuity threshold can be defined in the chart-invariant domain represented by chart-invariant psychometric functions, e.g., the sensitivity (d')-based psychometric function. Alternatively, the acuity threshold can be defined by chart-specific psychometric functions, e.g., an empirical psychometric function that depends on the factor(s) of acuity chart design. There may be a direction transformation between acuity thresholds defined by chart-specific psychometric functions and chart-invariant psychometric functions.

Figure 4A:
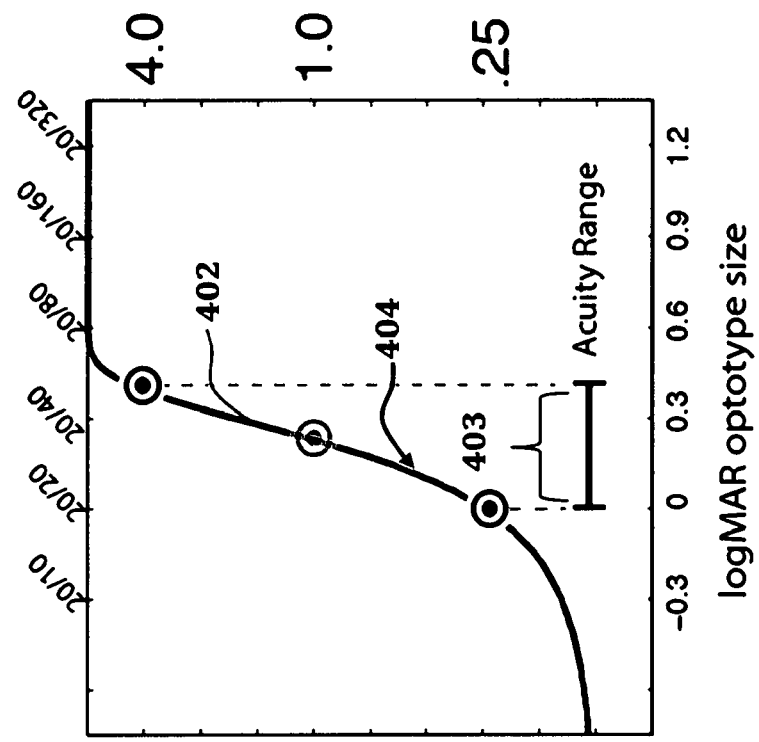
FIG. 4A-4B show a non-limiting example of a sensitivity (d')-based single-optotype psychometric function, which is a psychometric function (in d' units from Signal Detection Theory) that is chart-invariant and describes perceptual sensitivity independently of the decision level factors that are affected by acuity chart design parameters.
Figure 4B:
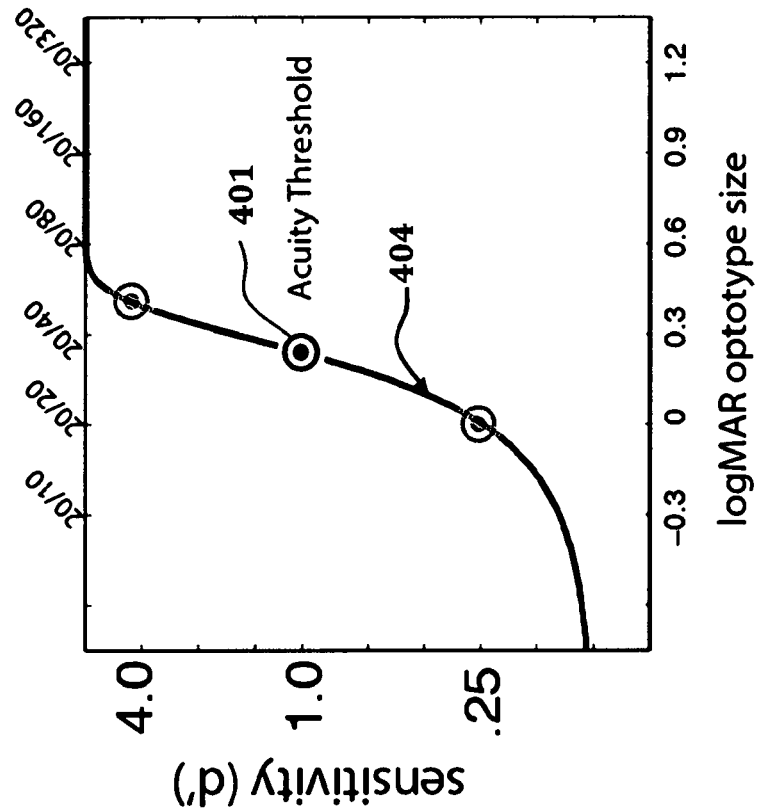
Figure 7B:
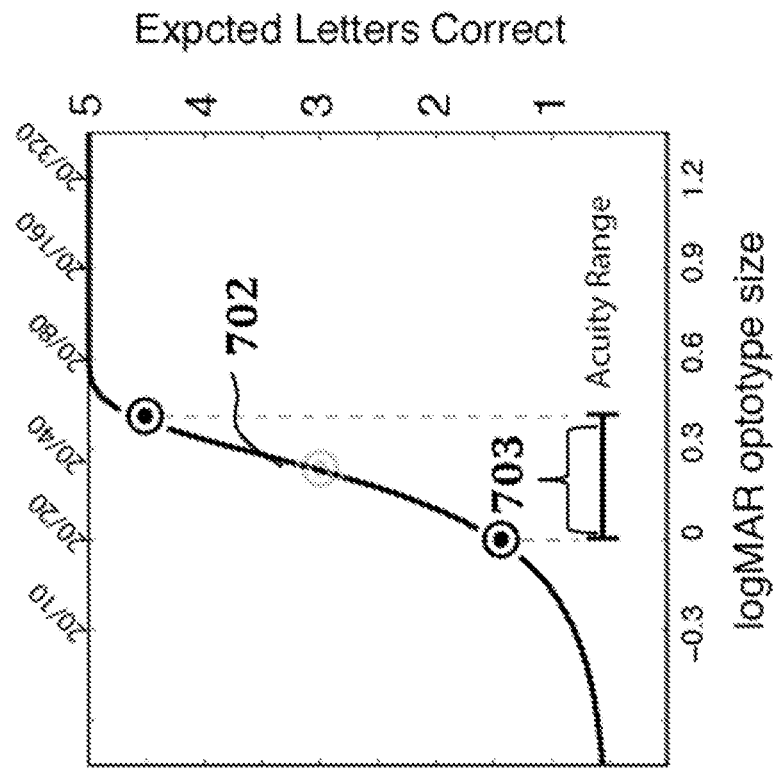
FIG. 7 shows a non-limiting example of a chart-specific psychometric function, defined by chart-specific acuity threshold and chart-specific acuity range, for the recognition of five optotypes presented on a slide, as a function of optotype size.
Figure 7A:
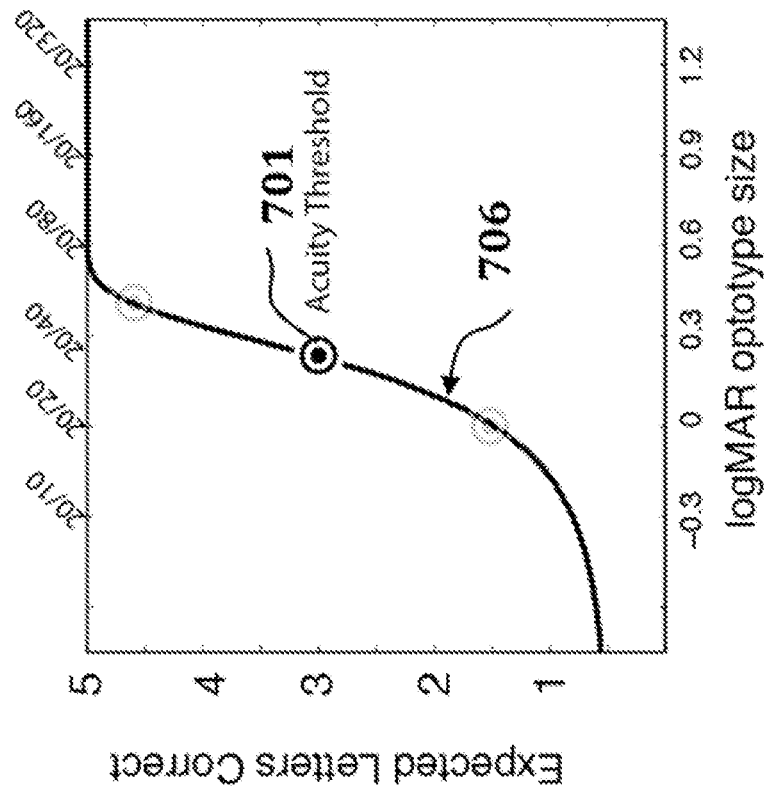

Referring to FIGS. 4A-4B and/or FIGS. 7A-7B, in a particular embodiment, the threshold 401, 701, is shown using different coordinates, sensitivity threshold 401, and acuity threshold 701 can be in different units. As shown in FIG. 7A, in some embodiments, the acuity threshold 701 represents the an optotype size that corresponds to a pre-specified criterion of visual performance: for example, the size corresponding to the probability of correctly identifying an optotype of a certain size, or the size corresponding to reporting three out of five optotypes correct on a line of the ETDRS chart. In the same embodiment, a second critical metric for describing acuity chart performance is the sensitivity slope 402 (FIG. 4B) or acuity slope 702 (FIG. 7B), which describes how rapidly the chart-specific psychometric function changes around the threshold 401, 701. In some embodiments, the slope represents how fast the acuity changes with the size change of optotypes. In some embodiments, the acuity or sensitivity slope 402, 702 is inversely related to the acuity range, which represents the width of the dynamic range of the acuity function. In this case, the acuity or sensitivity range 403, 703 determines the log difference between the two optotypes sizes that correspond to expected performance levels of 1.5 and 4.5 letters correctly recognized. A 0.40 log MAR optotype size difference (the acuity range in FIG. 4B) corresponds to an acuity range equivalent to four lines on the ETDRS chart. In this case, the subject reading an ETDRS chart would transition from their best average performance (5 of 5 correct at a higher line) to their lowest average performance (½ of 5 correct at a lower line) over the range of four lines on the ETDRS chart. Algorithm S (scoring algorithm) may yield acuity threshold and range estimates as the critical assessments of vision. In some embodiments, the acuity threshold may provide the primary metric or parameter, but recognizing changes in acuity range/slope may provide a secondary assessment or parameter that is useful when characterizing vision loss in eye disease. The power of the acuity model may include reducing the rich and complex data collected from visual acuity testing to a simpler prediction of vision with two parameters.

In some embodiments, the acuity parameter herein includes an acuity threshold, acuity range, acuity slope, sensitivity threshold, sensitivity range, sensitivity slope, or a combination thereof at one or more test conditions. In some embodiments, the acuity parameter herein includes a change in acuity threshold, acuity range, acuity slope, sensitivity threshold, sensitivity range, sensitivity slope, or a combination thereof between two test conditions. In some embodiments, the acuity parameter herein is a numerical value in units reflecting the optotype size, e.g., 20/20, 20/40, 3/5 (3 out of 5), 1/5 (1 out of 5), or 0.3 log MAR. In some embodiments, the acuity parameter herein corresponds to a pre-determined level of visual performance, which can be defined in chart-invariant terms (sensitivity) or chart-specific terms, thus generating sensitivity-based acuity parameters (e.g., sensitivity threshold and range) and acuity parameters (e.g., acuity threshold and range), respectively. Referring to FIGS. 4A-4B, in some embodiments, an acuity threshold that is chart-invariant can be an optotype size, e.g., 0.3 log MAR corresponding to a pre-specified sensitivity level, d'=1 or d'=2. In the same embodiments, an acuity range that is chart-invariant can be the difference between two optotype sizes that correspond to a low sensitivity (e.g., −0.3 log MAR at d'=0.5) and a higher sensitivity (e.g., 1 log MAR at d'=4). Referring to FIGS. 7A-7B, which presents a chart-specific psychometric function, an acuity threshold that is chart-specific can be the optotype size, e g. 0.3 log MAR corresponding to a pre-specified number of correctly reported letters expected out of 5, e.g., 3 out of 5 or 3/5, or 2, 4, or 3.5 out of 5. In the same embodiments, the acuity range can be the difference between two optotype sizes corresponding to a lower number of correctly reported letters (e.g. −0.3 log MAR for 1 out of 5) and a higher number of correctly reported letters (e.g., 0.9 log MAR for 4 out of 5).

In some embodiments, acuity change, e.g., between two different test conditions is measured using the systems and methods herein, for example, via analyses of Bayesian posterior probability density functions (pdf). The Bayesian pdf for acuity differences between two test conditions can be generated from the individual pdfs of the test conditions (Hou et al 2016, which is incorporated herein entirely by reference) for the case of contrast sensitivity:

$$p_{difference}(\Delta a) = \int_{a=-\infty}^{\infty} p_1(a)p_2(a-\Delta a)da,$$

where a represents the acuity measured in the first test condition and $\Delta a$ represents the acuity difference between the two conditions; $p_{difference}(\ )$ is the probability function of the acuity difference and $p_1(\bullet)$ and $p_2(\bullet)$ are the Bayesian pdfs defined over the acuity parameters in the two conditions, respectively.

Referring to FIGS. 27A-27B, in a particular embodiment, the Bayesian posterior probability density functions of acuity threshold under different test conditions, 1, 2, 3, and 4 are generated. In this embodiment, the probability of acuity change between two test conditions, can be calculated via the relative overlap of Bayesian posterior probability density functions measured in different test conditions. As shown in FIG. 27A, the low variability in acuity threshold estimation, e.g., width of the probability density functions, of the Bayesian posterior probability density functions provides confidence about visual acuity change between test 1 and test 2 that is reflected in the minimal overlap 2710a of the acuity threshold posteriors collected in different conditions. Referring to FIG. 27B, the mean differences in acuity between test conditions 2810 is the same, in some embodiments, but there is wider variability, e.g., width of the probability density functions in the acuity threshold estimates, represented by the wider variability, increased dispersion, and increased overlap 2710b of the Bayesian posteriors (pdf).

The calculation of acuity change or acuity difference via Bayesian signal detection analysis herein may include generation of a difference distribution, e.g., the Bayesian pdf in test 1—the Bayesian pdf in test 4 as shown in 2811 in FIGS. 28A-28B, between acuity values obtained in different conditions 2810, e.g., before or after a medical intervention. Following the collection of posteriors in individual test conditions, the generation of difference distributions 2811 provides an equivalent index of acuity threshold change as shown in FIG. 28B.

In some embodiments, the generation of a difference distribution between the Bayesian posteriors of two test conditions, e.g., test 1 and test 2, provides an estimate that the change between conditions is greater than a threshold criterion level of acuity change. For example, the threshold criterion level may be greater than 1-line of a given acuity chart, or greater than 2-lines, or greater than 3 lines of a given acuity chart.

In some embodiments, rather than test high-contrast visual acuity with black optotypes on a white background, low-contrast visual acuity can also be tested with gray-level optotypes demonstrating smaller differences in brightness from the gray-level background. For example, using the design of the Sloane low-contrast charts. In some embodiment, the visual acuity charts used for test visual acuity with low contrast appear similarly to ETDRS, but different charts can present optotypes at about 25.0%, 2.5%, and 1.5% contrast, calculated relative to the standard background of visual acuity charts. In some embodiments, low-contrast visual acuity chart has one or more contrasts that are about no greater than 60%, 50%, 40, 30%, 25%, 24%, 20%, or even lower than the contrast of a normal ETDRS and/or Sloane acuity charts. In some embodiments, low-contrast visual acuity chart has one or more contrasts that are about no greater than 25%, 20%, 18%, 15%, 12%, 10%, 8%, 5%, 2.5%, 2%, 1.5%, or even lower than the contrast of a normal ETDRS and/or Sloane acuity charts.

In some embodiments, the difference distribution can be alternatively directly estimated when a more complicated acuity model is used: e.g., with two acuity thresholds and two acuity ranges.

In some embodiments, the Algorithm S and A can be utilized to directly measure acuity model change which reflects acuity change or acuity difference. In some embodiments, a two-dimensional acuity model determined by using two acuity parameters herein as two dimensions can be elaborated into a model with higher dimensions, e.g., three, four, five, size or even more dimensions. For example, a two-dimensional acuity model can be used to expand into a four dimensional model in two ways: (a) to measure the acuity thresholds and acuity ranges in two test conditions; Algorithm A then can select which is the optimal stimulus and which is the optimal condition to test on trial-to-trial basis; (b) to measure the acuity threshold and range in one condition, and the difference between conditions in threshold and range as a second set of parameters, i.e., delta-threshold and delta-range. For example, the acuity model may assume that there is no difference in acuity range expected between two conditions. In other words, the acuity differences between two test conditions can be characterized as lateral shifts in the chart-specific acuity function, without a change in the acuity range parameter.

In some embodiments, the results from an acuity model analysis are evaluated to determine the probability of a change in acuity threshold, acuity slope, and/or or acuity range.

In some embodiments, the acuity model herein is configured to directly estimate the acuity change. Such acuity change may be between two test conditions or among more than two test conditions. In some embodiments, different test conditions can include any difference in the subject. For example, pre or post medical intervention. As another example, test of a diseased eye and a normal eye, or test of a left eye and test of a right eye. In some embodiments, the acuity model herein can estimate acuity threshold, acuity range, and change in acuity threshold, and acuity range. In some embodiments, the acuity parameters includes an acuity threshold and an acuity range from a first test condition and a second condition different from the first, and additional parameters determining the difference (e.g., delta acuity threshold between the first and second test condition) between those parameters. In some embodiments, the first condition is the left eye and the second condition is the right eye. In some embodiments, the first condition is pre-treatment and the second condition is post-treatment. In some embodiments, the first condition is measured at a lower-luminance and the second condition is measured at a higher-luminance. In some embodiments, the first condition is measured at a lower-contrast and the second condition is measured at a higher-contrast.

Summarize Acuity Chart Data

In some embodiments, the systems and methods herein includes acuity chart data obtained by collecting response of the test subject to the presented acuity chart(s) or subchart(s). The acuity chart data is interchangeable herein as acuity test data, and/or response(s). In some embodiments, the response(s) of the test subject is summarized, for example, in a data table. For a single optotype, the response r may be the correctness of the single response for that optotype. For a line of multiple optotypes, the composite response, r, may summarize how many optotypes, m, are correctly recognized, out of the total n optotypes presented per line. Because it's possible to correctly report between 0 and n (out of n) optotypes per line, there can be n+1 potential outcomes for the composite response.

As shown in operations 100 and 400 of FIG. 1, in some cases, acuity chart design features can be determined and chart design parameters can be summarized. In some embodiments, data table herein (e.g., Table 1) co-locates the parameters that define the chart design and the parameters of the subject's response that are important for application of the acuity model.

Table 1 shows exemplary summarized acuity chart data collected from a test subject.

TABLE 1

| | Acuity Chart Design: Optotype Parameters | | | | |
|---|---|---|---|---|---|
| Data Entry | Optotype Number Total | Optotype Number per Line | Optotype Sampling | Optotype Size | Response |
| 1 | $t_1$ | $u_1$ | w/o | $s_1$ | $r_1$ |
| 2 | $t_2$ | $u_2$ | w/o | $s_2$ | $r_2$ |
| 3 | $t_3$ | $u_3$ | w/o | $s_3$ | $r_3$ |
| ... | ... | ... | ... | ... | ... |
| k | $t_k$ | $u_k$ | w/o | $s_k$ | $r_k$ |

In Table 1, each row may define a single acuity chart condition, comprised of the optotype size for the single optotype or single line of optotypes, and the corresponding single or composite response to the presented optotype(s). In this particular case shown in Table 1, acuity chart data collected from a test subject is summarized. To apply Algorithm S to score acuity chart data, this summarization may help identifying design features that contribute to visual performance observed during acuity chart testing. In this summary table, each line entry signifies the reading of a single optotype or single line of optotypes from a visual acuity chart or sub-chart. Each line of optotypes can be considered as a composite stimulus, which in addition to the critical feature of optotype size, is described by: the size of the subset of optotypes sampled on each line, the size of the superset of optotypes that they are sampled from, and whether sampling from the superset is done with or without replacement. For each row of chart design parameters in the summary table, the response summary represents the number of correctly recognized optotypes, whether for a single optotype or a line of optotypes. In some embodiments, optotype parameters as shown in Table 1 may critically affect the chart-specific psychometric function, thus they are needed for the generation for the chart-specific psychometric function.

In some embodiments, the acuity test data may include test data from 1, 2, 3, 4, 5, or even more test conditions.

Candidate Parameters for Acuity Model

In some embodiments, one or more sets of candidate parameters can be generated using the systems and methods herein. A set of candidate acuity model parameters may comprise a combination of two or more acuity parameters, such as acuity threshold and acuity range, etc. Various combinations of the acuity parameters can make multiple sets of candidate parameters. Such sets of candidate parameters are configurable to describe the acuity chart data summarized, as shown in Table 2 below. In operation 300 of FIG. 1, such candidate parameters, e.g., as shown in Table 2, can be determined at least in part by acuity chart data or acuity test data collected from the test object operation 400. Alternatively or in combination, such candidate parameters can be determined at least in part by acuity chart design parameters determined in operation 100. In some embodiments, operation 300 may be independent of the design parameters in operation 100. In some embodiments, Operation 300 occurs prior to operation 200. And each set of candidate parameters in operation 300 are used in operation 200, e.g., FIGS. 3A and/or FIG. 3B in determination of the generic acuity model. In some embodiments, operation 300 may be in parallel or in series to operation 400 and/or operation 100.

Table 2 shows the candidate sets of acuity model parameters. These sets of acuity threshold and acuity range parameters comprise the acuity model parameters that can potentially describe the acuity chart data collected from the test subject. Each entry line reflects a single combination (out of q in total) of q1 candidate acuity threshold parameters and q2 candidate acuity range/slope. In this embodiment, the table has a combination number of q1 times q2.

TABLE 2

| Acuity Model Entry | Candidate Acuity Model Parameters | |
|---|---|---|
| | Acuity Threshold | Acuity Range |
| 1 | $\alpha_1$ | $\beta_1$ |
| 2 | $\alpha_1$ | $\beta_2$ |
| 3 | $\alpha_1$ | $\beta_3$ |
| ... | ... | ... |
| q | $\alpha_{q1}$ | $\beta_{q2}$ |

In some embodiments, the observed acuity chart data are analyzed to infer the acuity model parameters that best predict the acuity from the test subject. In some instances, the set of acuity model candidate parameters is a list of parameter combinations for acuity threshold and acuity range. Statistical inference may describe the probability of each parameter combination describing the observer. This is equivalent to estimating the probability of class membership. In alternative cases, the set of candidate parameters includes a two-dimensional space of acuity parameters—acuity threshold and acuity range—that provide exhaustive combinations of parameters to describe the subject's acuity performance. In this approach, marginal probabilities can be calculated across the two dimensions of the acuity parameters.

The sets of candidate acuity parameters can be implemented in the acuity model for visual acuity analysis. For example, the sets of candidate acuity parameters can be a one-dimensional array of acuity threshold-range pairs. As another example, the sets of candidate acuity parameters can be two-dimensional and can be used to generate acuity model(s) that describes exhaustive combinations of acuity threshold and acuity range. As yet another example, the set of candidate acuity parameters can be four-dimensional: acuity threshold and range in a baseline condition (e.g., left-eye or pre-treatment condition) and changes in acuity threshold and acuity range relative to those conditions.

In some embodiments, each set of acuity parameters can include 1, 2, 3, 4, 5, 6, 7, 8, 9, 10, or any other integer number of acuity parameters.

In some embodiments, there can be 1, 2, 3, 4, 5 . . . 1000 . . . 10000, or any other integer number of sets of candidate acuity parameters.

In some embodiments, each set of candidate acuity parameters includes an equal number of parameters. In some embodiments, each set of candidate acuity parameters includes one or more of: an acuity threshold, acuity range, acuity slope at one or more test conditions, a change in acuity threshold, range, or slope between two test conditions.

In some embodiments, each set of candidate acuity parameters includes one or more of: an sensitivity threshold, sensitivity range, or sensitivity slope at one or more test conditions, a change in sensitivity threshold, range, or slope between two test conditions. In some embodiments, the candidate acuity parameter herein includes an acuity threshold, acuity range, acuity slope, sensitivity threshold, sensitivity range, sensitivity slope, or a combination thereof at one or more test conditions. In some embodiments, the candidate acuity parameter herein includes a change in acuity threshold, acuity range, acuity slope, sensitivity threshold, sensitivity range, sensitivity slope, or a combination thereof between two test conditions. In some embodiments, the candidate acuity parameter herein is a numerical value in units reflecting the optotype size, e.g., 20/20, 20/40, 3/5 (3 out of 5), 1/5 (1 out of 5), or 0.3 log MAR. In some embodiments, the candidate acuity parameter herein corresponds to a pre-determined level of visual performance, which can be defined in chart-invariant terms (sensitivity) or chart-specific terms, thus generating sensitivity-based acuity parameters (e.g., sensitivity threshold and range) and acuity parameters (e.g., acuity threshold and range), respectively. In some embodiments, the candidate acuity parameter defined in chart-invariant terms (sensitivity) or chart-specific terms can be converted to each other. In other words, a set of chart-invariant sensitivity parameters can be converted to a set of chart-specific acuity parameters using the same optotype information, e.g. optotype size related to acuity performance, e.g. 0.3 log MAR, but sensitivity or acuity terms, e.g. at d'=2, or 3 out of 5, respectively. In some embodiments, candidate acuity parameters are interchangeable with candidate acuity model parameters, or candidate parameters.

Acuity Models

In some embodiments, the methods, systems, or devices disclosed herein include one or more acuity models (interchangeably herein as "statistical models", or "predictive models"). Such terms are equivalent and interchangeable herein. In some embodiments, the acuity model is used to predict acuity chart data of the subject (e.g., probability of observing specific response(s) from the subject), the acuity chart data indicating visual acuity performance of a subject. In some embodiments, such prediction using the acuity model is based on design features of the acuity chart used to collect acuity chart data from the test subject. In some embodiments, such prediction by the acuity model is invariant to specific acuity chart design features.

Referring to FIG. 1, in a particular embodiment, an acuity model may be determined using operations 200, 300, and/or 350. In some embodiments, the acuity model herein includes model parameters. Such model parameters can include: (a) acuity chart design parameters that are fixed, at least in part determined by the acuity chart design, which are at least in part determined by operation 100; (b) set(s) of candidate acuity parameters that describe the vision of the patient, which can be determined at least in part in operation 300. In operation 300, sets of the candidate acuity parameters to be used to populate the acuity model are estimated. In operation 200, each set of the estimated sets of parameters in operation 300 are used to generate the chart-specific function in operation 200 and FIG. 3A and/or FIG. 3B, in some cases, in combination with acuity chart design parameters. Afterward, the chart-specific functions are used in operation 350 to populate the acuity model to be used in operation 500. In some embodiments, the function of the acuity model is to output a prediction for acuity chart data or test data (e.g., response probability) using acuity chart design parameters (in operation 100), candidate acuity parameters (in operation 300), and the collected acuity chart data (in operation 400). In some embodiments, operation 350 can use at least a part of the multiple sets of candidate parameters and their corresponding chart-specific psychometric functions for generating the prediction for acuity chart data or test data (e.g., response probabilities). In some embodiments, operation 350 can use all of the multiple sets of candidate parameters and their corresponding chart-specific psychometric functions for generating the prediction for acuity chart data or test data (e.g., response probabilities).

An acuity model may include one or more acuity parameters. Nonlimiting examples of acuity parameters includes: acuity threshold, acuity slope, acuity range, sensitivity threshold, sensitivity range, acuity threshold change between two test conditions, and acuity range change between two test conditions. Given the acuity model, acuity model parameters may be used to predict the visual performance observed during testing with any acuity chart design. These model parameters may provide valuable acuity metrics to characterize the vision of test subjects.

In some embodiments, the acuity model includes a central component—chart-specific psychometric function, which is configured to allow determination of the expected number of optotypes correctly recognized on a line of the acuity chart, as a function of the size of optotypes on that line.

FIGS. 7A-7B show an exemplary embodiment of the chart-specific psychometric function 706, which represents the expected number of optotypes correctly recognized on each line of optotypes, as a function of the number of optotypes presented on that line. Algorithm S may apply the acuity model to acuity chart data to estimate features of the chart-specific psychometric function.

The systems and methods disclosed herein can estimate the chart-specific psychometric function 606, 706, single-optotype psychometric function that is chart-invariant 404 or chart-specific, 604, 804 and/or multiple-optotype psychometric functions 605, 805, and/or its acuity parameters, e.g., chart-specific acuity threshold, 701, acuity range 703, and slope 702, or chart-invariant sensitivity threshold, 401, sensitivity range, 403, sensitivity lope, 402, to assess visual acuity.

For instances the chart-specific psychometric function 604, 804 can depend critically on the specific design features of the acuity chart used to collect the chart acuity data. The chart-specific psychometric function may also predict acuity chart data collected on many different acuity charts, by incorporating features of acuity chart design. These features include but are not limited to:
number of lines presented in the chart or sub-chart;
number of optotypes presented per line;
number of optotypes potentially sampled for each line;
number of optotype sizes potentially sampled for each line;
whether that pool of optotypes is sampled with or without replacement; or their combinations.

As a non-limiting example, for a standard log MAR acuity chart (ETDRS or Bailey-Lovie), which presents five optotypes on each line, the chart-specific psychometric function describes the number of optotypes that are expected to be correctly recognized on each line, as a function of optotype size.

As another example, for the log MAR acuity chart, two critical acuity metrics that summarize the chart-specific psychometric function are: chart-specific acuity threshold— the optotype size (in log MAR) at which the subject correctly recognizes a criterion number of optotypes per line, and chart-specific acuity range—this parameter is correlated with the width of the dynamic range of the psychometric function, and anti-correlated with the function's slope. In some embodiments, the acuity range describes the log MAR difference between two optotype sizes: one above and one below the performance level of the acuity threshold. In some embodiments, the range parameter describes how rapidly the acuity-chart specific psychometric function changes around the acuity threshold. A small range signifies that the observer's vision rapidly transitions from incorrect to correct optotype identification as optotype size grows from small to large. In some embodiments, the acuity range is a valuable metric because one signature of eye disease is increased variability in vision, which corresponds to an increase or a change in acuity range.

For example, for the log MAR acuity charts, the acuity threshold is the optotype size corresponding to the correct identification of 3 out of 5 optotypes per line, with the acuity range corresponding to the distance between chart lines with expected numbers of 1.5 and 4.5 optotypes correctly identified per line.

In some embodiments, other features of the psychometric function are defined by design features of the acuity chart. These features may include Lower Asymptote—defined by guessing rate over the total number of possible optotypes, and Upper Asymptote—defined by the number of optotypes presented on each line.

Figure 3B:
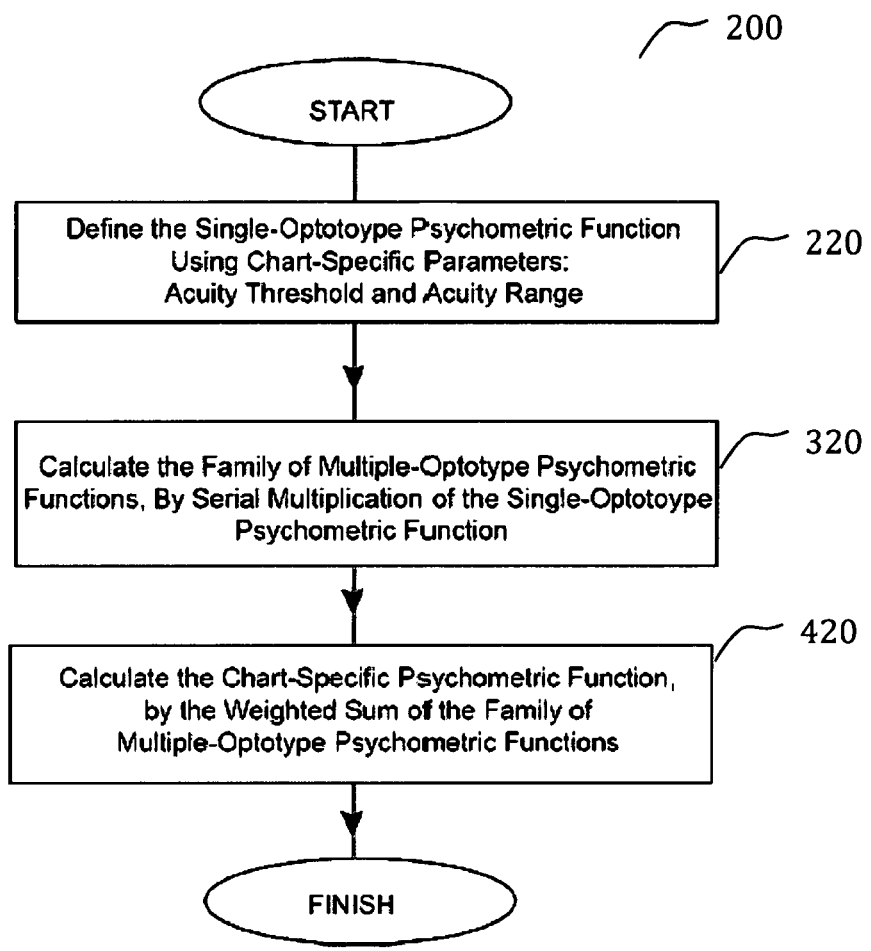
FIG. 3B shows a non-limiting example of a flow chart of generating a chart-specific acuity model.

In some embodiments, to construct the chart-specific psychometric function 706, 606, which describes the expected number of correctly recognized optotypes per line, as a function of optotype size, the chart-specific single-optotype psychometric function is generated by operation 220 in FIG. 3B or operations 230 and 330 in FIG. 3A. the chart-specific single-optotype psychometric function can be generated based on a chart-invariant single-optotype psychometric function 404 that is defined in sensitivity parameters that are independent of the task-based features of the acuity chart (FIGS. 4A-4B), e.g., acuity chart design parameters or features. In some embodiments, the single-optotype psychometric function shows the probability of correctly recognizing a single optotype, as a function of optotype size and is determined by two acuity model parameters—e.g., acuity threshold and acuity range, in some cases, using cumulative distribution function(s), such as Gaussian cumulative probability distribution functions. The sensitivity-based chart-invariant single-optotype psychometric function is then translated into a single-optotype chart-specific psychometric function based on the principles of Signal Detection Theory (Green & Swets, 1961; McMillan & Creelman, 2004; Lesmes et al, 2015, which are incorporated herein entirely by reference), and features of the optotype set (FIG. 5). This transformed single-optotype chart-specific psychometric function, for instances, depends on features of acuity chart design, such as the number of potential optotypes. The same sensitivity threshold (optotype corresponding to d'=1) can represent different levels of correct performance for signal optotypes, based on the number of optotype alternatives. As noted in Signal Detection Theory, it is easier to guess correctly when there are fewer guessing alternatives. Therefore, for the same optotype size corresponding to a given sensitivity threshold (d'=1), the number of guessing alternatives in the optotype set can result in different levels of percent correct performance for identifying single optotypes: ranging from 70-80% for two-alternatives and 30-40% for ten alternatives at the sensitivity threshold of d'=1 (FIG. 5).

In some embodiments, the combination of operations, e.g., 300, 200, and 350 generates an acuity model that can be applied to score the acuity chart data collected and summarized in operation 400. This acuity model can comprise a large number of predictive probabilities, for example, in a table for the observed acuity chart data, which can be the predictive probabilities of different responses recorded for the optotypes presented to the patient for a given set of candidate acuity model parameters that describe the patient's vision.

Figure 6A:
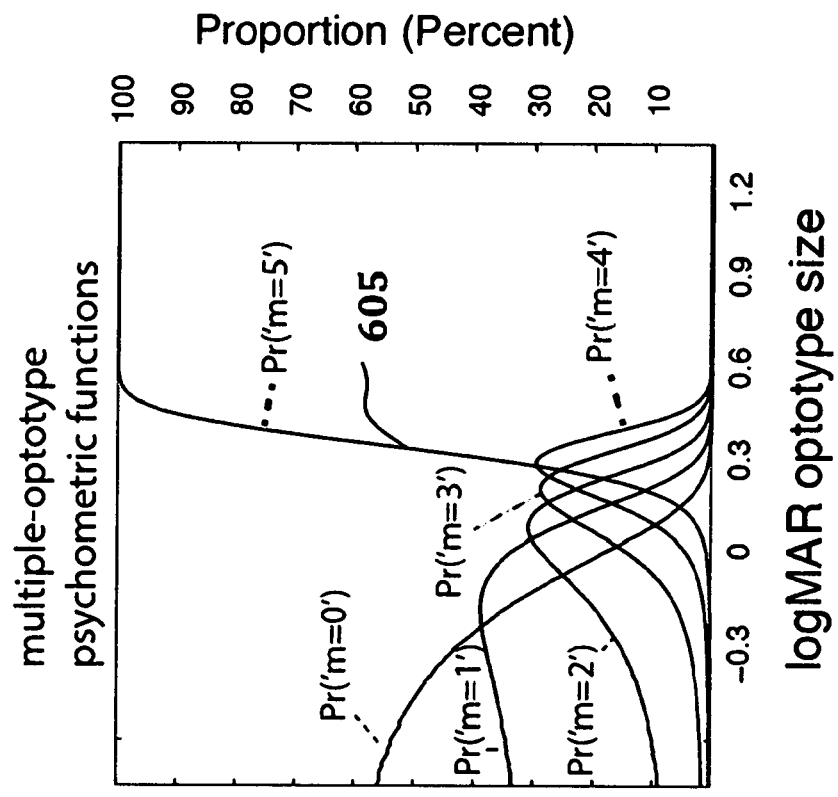
FIGS. 6A-6B show a non-limiting example of a single-optotype psychometric function based on ten guessing alternatives (FIG. 6A) and the different aggregate multiple-optotype psychometric functions (FIG. 6B) generated by the acuity model for the recognition of five optotypes presented on a slide, as a function of optotype size.

In one embodiment, a two-parameter description of visual acuity may use a sigmoidal function to define visual performance as a function of optotype size (see FIGS. 4A and 6A for examples). One parameter, the acuity threshold, can describe the lateral position of the sigmoidal function on the horizontal axis of optotype size. The other parameter, the acuity range, can describe how rapidly the sigmoidal function changes over the horizontal axis of optotype size, in the neighborhood of the threshold. A small range may signify that the acuity function changes rapidly from the inferior visual performance signified by the function's lower asymptote and the superior performance signified by the function's upper asymptote. Both acuity threshold and acuity range parameters can be defined in units of log MAR optotype size.

Referring to FIG. 7A, the acuity threshold and acuity range are defined, in some embodiments, in terms specific to the ETDRS acuity chart design. The ETDRS chart can present 5 letters per line for a range of optotype sizes. In FIGS. 7A and 7B, the acuity function therefore demonstrates an upper asymptote of five letters reported correctly out of five. In FIG. 7A, the acuity threshold 701 is defined as the optotype size at which the patient is expected to correctly report three of five presented optotypes. In FIG. 7B, the acuity range 703 defines the horizontal range over which visual behavior on the ETDRS chart changes from correct report of 1.5 of 5 letters to correct report of 4.5 of 5 letters. In these embodiments, because the acuity threshold and acuity range are defined by three performance levels—1.5, 3.0, and 4.5 letters correctly reported out of 5—that are defined by features of the ETDRS chart, acuity threshold and range can be considered as chart-specific acuity model parameters.

In some embodiments, presented in FIGS. 4A and 4B, acuity threshold 401 and acuity range 403 are defined in sensitivity units (d') that are independent of acuity chart design. The acuity threshold can be defined as the optotype size (in log MAR) corresponding to a visual performance of d'=1. The acuity range can be defined as the difference (in log MAR) between the optotype sizes corresponding to an inferior level of visual performance (d'=0.25), and a superior level of visual performance (d'=4). Due to the definition of these acuity model parameters in units of sensitivity, sensitivity threshold and range can be considered as chart-invariant acuity model parameters.

To understand how operation 350 generates a predictive model for acuity chart data from chart-invariant parameters, it can be instructive to consider one generic pair of acuity model parameters: one acuity threshold and one acuity range (e.g., the pair of parameters comprising the first row of Table 2). From this selected pair of acuity model parameters, the probabilities of observing different responses during acuity chart testing can be obtained, as a function of optotype size. In addition to these acuity model parameters, consider one factor of acuity chart design: the range of optotype sizes likely to be tested in an acuity chart. For example, ETDRS charts use optotype sizes that range from -0.3 to 1.0 log MAR, with a 0.10 log MAR resolution.

FIG. 4A shows an exemplary embodiment of the chart-invariant psychometric function that can result from continuous sampling of optotype sizes that are similar to ETDRS testing. Signal Detection Theory describes how sensitivity parameters that are task-independent can be transformed into measures of task-based behavior (e.g., the probability of correctly identifying an optotype). Using Signal Detection Theory (Green & Swets, 1961; McMillan & Creelman, 2004; Jacobs & Fine, 2002; Lesmes et al, 2015, which are incorporated herein entirely by reference), the probability for correctly identifying a single optotype is derived from d' values based on the Gaussian distributions assumed for internal representations of signal and noise for identification tasks with different numbers of guessing alternatives. For the equation describing this transformation, see Appendix A, Equation 7 from Jacobs & Fine, 2002, or Equation 1 from Hacker & Ratcliff, 1979. Alternatively, McMillan & Creelman (2004) presents Table A5.7 as a look-up table to translate between corresponding levels of sensitivity (d') and Probability Correct, for m-AFC alternative tasks that range from m=2 up to m=1000.

As an example, FIG. 5 demonstrates that for a generic stimulus corresponding to a sensitivity level of d'=1, the probability of correct identification is between 70% and 80%, when there are only two guessing alternatives (2AFC) (on any one trial, one alternative is correct and the other is incorrect, independent of any visual proficiency of the observer). As the number of guessing alternatives increases, there can be more possibilities for incorrect responses. Therefore, the probability of a correct response decreases as the number of guessing alternatives increases (see the relative layering 504 of functions in FIG. 5). To compare with 2AFC, for a stimulus corresponding to a sensitivity level of d'=1, when presented with 10 guessing alternatives, the probability of correctly reporting that stimulus is about 30%.

Based on this transformation 330 from sensitivity (d') to Probability Correct (FIG. 5), a pair of acuity model parameters that generate the sigmoidal function in FIG. 4A can generate a monotonically increasing function that describes the probability of correctly reporting an optotype, as a function of optotype size. The transformation to use from FIG. 5 can depend on the number of the other optotypes (guessing alternatives) in the optotype sampling pool. In the case of ETDRS, which uses the Sloan set of 10 optotypes, the 10AFC function may be used to generate a psychometric function 604 for single optotype presentation (FIG. 6A).

Just as the number of optotypes in the sampling pool can be an acuity chart design factor that is used to transform the chart-invariant psychometric function to a single-optotype psychometric function (operation 330), another acuity chart design factor, i.e., the number of optotypes that are presented on each line, can be used to generate the family of multiple-optotype psychometric functions through serial multiplication. The weighted sum of this family of psychometric functions in turn provides a chart-specific psychometric function, FIG. 6C.

In some embodiments, given a single pair of acuity model parameters, e.g., acuity threshold and acuity range, six psychometric functions that describe, as a function of optotype size, the probabilities of correctly identifying 0, 1, 2, 3, 4, or 5 optotypes out of 5, can be generated. In operation 500, these probabilities can be used to evaluate which acuity model parameters best describe the test patient, given the acuity chart data collected during testing.

In some embodiments, operation 300 may include multiple sets of candidate parameters which are likely to be used in the acuity model. The purpose of the Scoring Algorithm S can be to evaluate these sets of candidate acuity model parameters, and evaluate which candidate parameters best describe the acuity chart data summarized in operation 400.

In some embodiments, in operation 300, the sets of candidate parameters can be defined in one or more following ways: a one-dimensional array/list of acuity model pairs, e.g., acuity threshold and acuity range; a one-dimensional array of acuity model pairs, comprising different values of acuity threshold and a fixed value of acuity range; a two-dimensional space defined by exhaustive combination of values of two parameters, e.g., acuity threshold parameters and acuity range parameters; a high-dimensional space (higher than 2 dimensions) of acuity threshold and acuity range parameters that describe acuity model parameters and their changes across different conditions.

For each of these sets of candidate acuity model parameters, the generation of acuity model probabilities from acuity threshold and range can be applied. In operation 500, these probabilities obtained using each set of these candidate acuity parameters can used to find the acuity model parameters that describe the acuity chart data.

For example, the number of potential optotypes may be different for various chart designs:
- 10 optotypes for Sloan, Bailey-Lovie;
- 4 for Landolt C, Tumbling E, HOTV, Lea, Hands;
- 9 for traditional Snellen;
- 12 for British Snellen standards BS 4274-1:2003;
- 26 for English Alphabet;

Afterwards, in some embodiments, the single-optotype psychometric function, P(s), is used to calculate a family of multiple-optotype psychometric functions, $P_m(s)$ that is specific to the design of the acuity chart (e.g., the number of optotypes presented on each line determines the number of psychometric functions). Such a family of multiple-optotype psychometric functions, $P_m(s)$, m=1, 2, 3, . . . shows systematic patterns of performance for correctly recognizing the multiple optotypes presented on multiple lines of a visual acuity chart, thereby determining the combined probabilities of correctly recognizing multiple optotypes presented on a line in an acuity chart as a function of optotype size. In some embodiments, a family of n+1 psychometric functions includes one function defined for each of n+1 composite response outcomes possible for correctly recognizing m out of n optotypes per line, as a function of optotypes size (with m ranging from 0 to n). In some embodiments, the number of psychometric functions in a family of multiple-optotype psychometric functions depends on the number of optotypes presented on each line. For example, 6 multiple-optotype psychometric functions for an ETDRS chart design with 5 optotypes per line. As another example, 4 multiple-optotype psychometric functions comprise the family for chart design with three optotypes presented on each line and 2 multiple-optotype psychometric functions comprise the family for e-ETDRS testing and other computerized chart designs with single-optotype presentation.

Figure 6B:
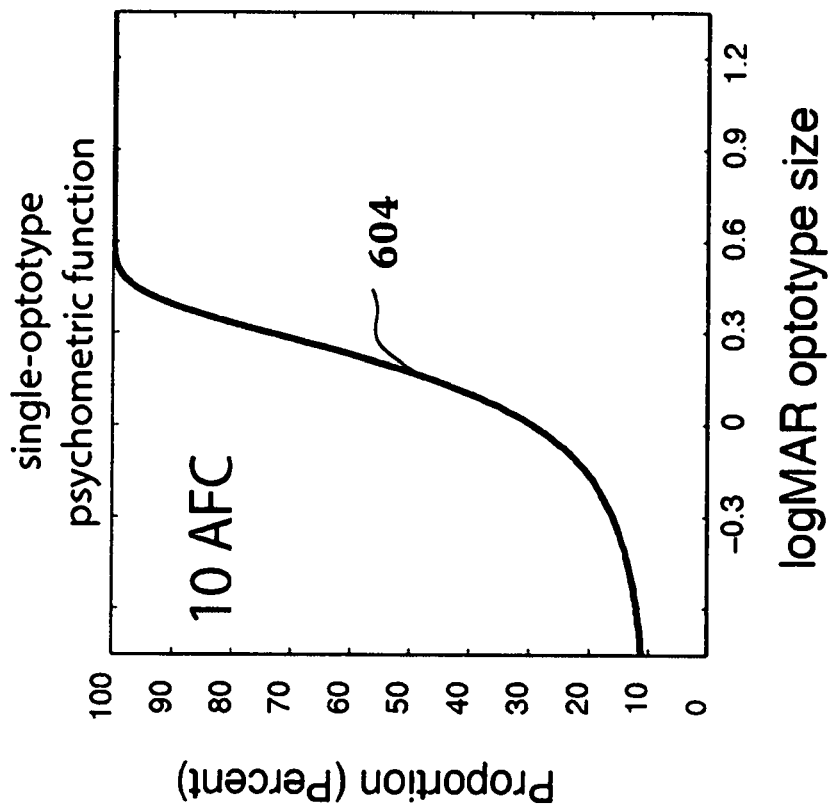

In some embodiments, the family of multiple-optotype psychometric functions determines probabilities for the composite responses to multiple optotypes, as a function of optotype size. Such probabilities can be calculated for the full sequence of optotypes by multiplying in series the probabilities for correctly recognizing single optotypes, P(s), and incorrectly recognizing single optotypes, 1−P(s), as a function of optotype size, s. Specifically, in a particular embodiment, for a line of n optotypes, the probability of correctly recognizing m out of n optotypes, is calculated as a function of optotype size, s, by:

$$P_m(s)=P(s)^m \times (1-P(s))^{n-m},$$

where m ranges between 0 and n, and P(s) is the single optotype psychometric function, which describes the probability of correctly recognizing a single optotype as a function of optotype size. In some embodiments, the family of multiple-optotype psychometric functions includes n psychometric functions, i.e., $P_m(s)$, with m in the range from 0 to n, when there are a line of n optotypes. FIG. 6A shows a nonlimiting example of the single-optotype psychometric function 604 determined by an optotype set with ten guessing alternatives, and FIG. 6B shows a nonlimiting example of a family of 6 multiple-optotype psychometric functions 605 determined by chart designs presenting five optotypes per line.

Referring to FIGS. 7A-7B, in a particular embodiment, scoring acuity chart data using algorithm S may require an acuity model that predicts the composite responses to multiple optotypes, as a function of optotype size. The probability of different composite responses to multiple optotypes can be predicted by a pair of acuity model parameters (e.g., threshold and range/slope) that determines a single-optotype psychometric function 704, which in turn can determine a family of optotype psychometric functions 705 for multiple optotypes through the serial multiplication of the single optotype psychometric, P(s), and its complement, 1−P(s). For example, the multiple-optotype psychometric function for 5 optotypes, Pr('m=5') is calculated as (Pr ('m=1')^5(1−Pr ('m=1')). In this case, for example, 'm=5' represents correctly identifying exactly 5 out of 5 optotypes. In this embodiment, the single-optotype psychometric function is obtained by presenting single optotypes in each test run to a subject (FIG. 7A), the multiple-optotype psychometric functions is generated by presenting multiple optotypes to a subject in each test run (FIG. 7B). In this case, an acuity chart is designed to present five optotypes per line, each of the multiple-optotype psychometric functions defines, as a function of optotype size, the probability of correctly recognizing some number of the multiple optotypes presented on a line of an acuity chart. In this particular case, only two of these multiple-optotype psychometric functions are monotonic. The probability of correctly recognizing no optotypes, P(m=0), decreases with increasing optotype size and the probability of correctly recognizing five optotypes increases with increasing optotype size. The performance patterns for intermediate composite responses are marked by staggered peaks, which signify the different regimes of optotype size that are mostly likely to demonstrate increasing numbers of correctly recognized optotypes. In some embodiments, the chart-specific psychometric function, which describes the expected number of correctly recognized optotypes, is generated by the weighted sum of these multiple optotype psychometric functions. (FIGS. 6A-6B)

In some embodiments, a computer model is used to predict a performance of a subject in a visual acuity test based on implicit sensitivity parameters. Referring to FIGS. 6A-6B, in this particular embodiment, to more clearly illustrate the concept of the multiple-optotype psychometric functions, the single-optotype psychometric function 604 as shown in FIG. 6A, and the multiple-optotype psychometric functions, e.g., 605, are presented (FIGS. 6A-6B) as cumulative probability distribution functions. In this case, 'm=5' represents correctly identifying exactly 5 out of 5 optotypes. In this case, the cumulative multiple-optotype psychometric functions describe the probability of correctly recognizing at minimum a given number of optotypes, as a function of optotype size. In some embodiments, the relative layering of these functions suggests systematic patterns of performance that demonstrate the increasing probability of correctly recognizing an increasing number of optotypes with increasing size of optotype.

In certain embodiments, scoring acuity chart data of a subject using algorithm S requires an acuity model that predicts the composite responses to multiple optotypes, as a function of optotype size. The probability of different composite responses to multiple optotypes may be predicted by a pair of acuity model parameters (for example, threshold and range) that delineate a single-optotype psychometric function, which in turn may generate a family of multiple-optotype psychometric functions through the serial multiplication of the single-optotype psychometric, P(s), and its complement, 1−P(s). The system and method advantageously uses the multiple-optotype psychometric functions, whose application to visual acuity testing is new.

For the example of an acuity chart design that comprises five optotypes per line, each of the multiple-optotype psychometric functions may determine, as a function of optotype size, the probability of correctly recognizing a number (the number being less than or equal to five) of the multiple optotypes presented on each line. As can be seen in FIG. 6B, among these psychometric functions for composite responses, only two of the multiple-optotype psychometric functions are monotonic. The probability of correctly recognizing no optotypes, P(m=0), maybe monotonically decreasing with increasing optotype size, and the probability of correctly recognizing all of the optotypes, P(m=5) may increase with increasing optotype size. The performance patterns for other intermediate composite responses are marked by non-monotonicity: the progression of staggered peaks may provide a quantitative approach to the intuition that increasing optotype size increases the probability of recognizing increasingly more number of correct optotypes. The staggered peaks of the multiple-optotype functions support the idea that different and successive regimes of optotype sizes represent the increasing probability for correctly recognizing an increasing number of optotypes, given an increase in the size of optotypes. The model provided herein with the multiple-optotype psychometric function may be a rich and complex characterization of acuity chart performance. Existing methods are unable to estimate this family of psychometric functions in a process feasible for acuity chart testing. The chart-specific psychometric function, which describes the expected number of correctly recognized optotypes, may be generated by the weighted sum of these multiple optotype psychometric functions.

Figure 8A:
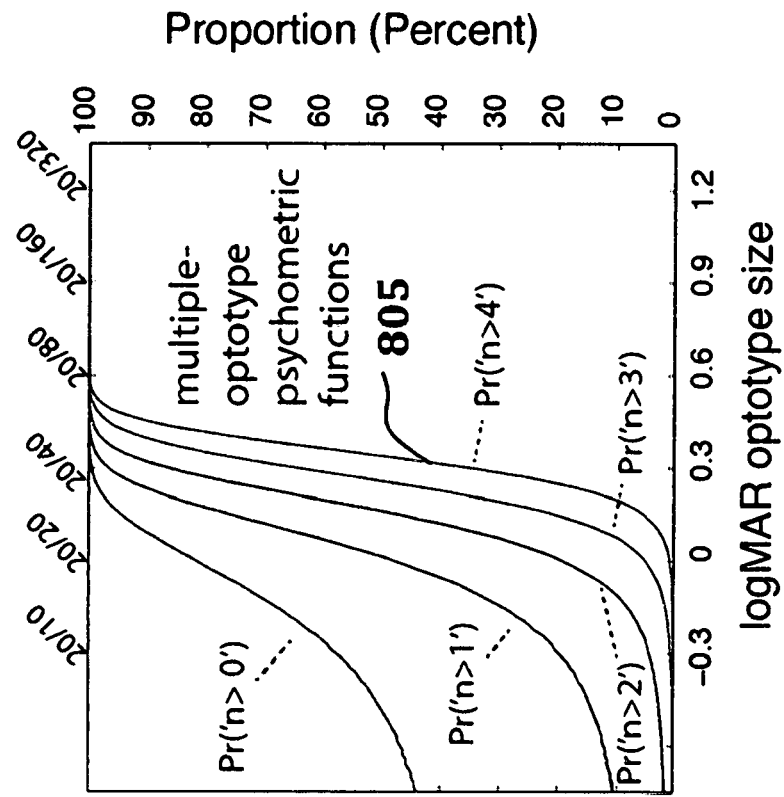
FIGS. 8A-8B show a non-limiting example of a single-optotype psychometric function (FIG. 8A) and different aggregate multiple-optotype psychometric functions (FIG. 8B) presented as cumulative probability density functions.
Figure 8B:
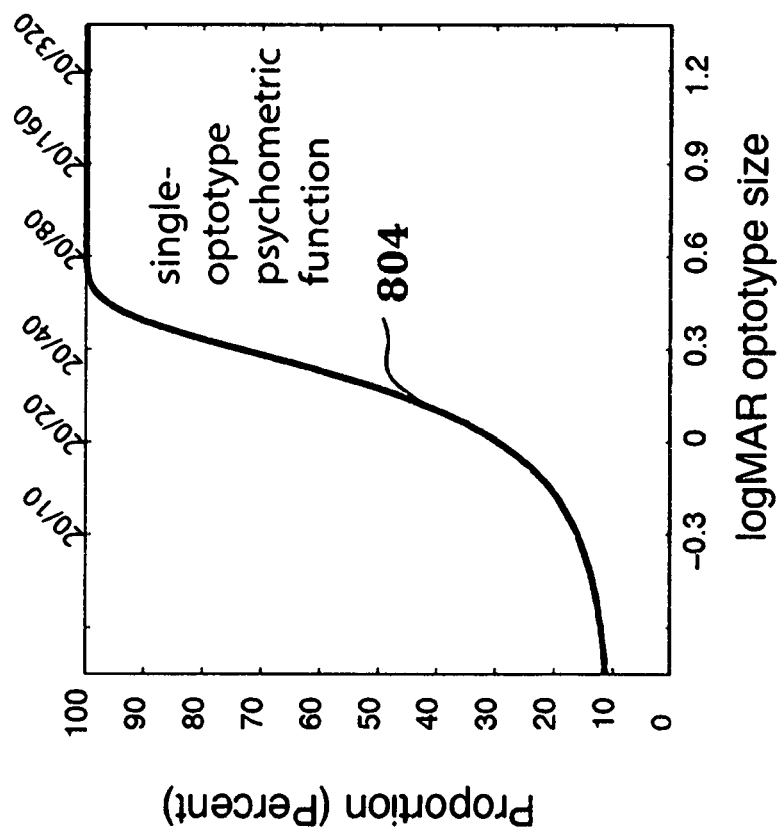

Referring to FIGS. 8A-8B, an exemplary embodiment of single-optotype psychometric function (801 in FIG. 8A), and the multiple-optotype psychometric functions (e.g., 802 in FIG. 8B) as cumulative probability functions are shown. In this particular embodiment, the cumulative multiple-optotype psychometric functions describe the probability of correctly recognizing at minimum a given number of optotypes, as a function of optotype size. The relative layering of these functions suggests systematic patterns of performance that demonstrate the increasing probability of correctly recognizing an increasing number of optotypes with increasing size of optotype.

In some embodiments, the family of multiple-optotype psychometric functions depends on the simplifying assumption of the statistical independence of responses to multiple optotypes. This assumption, which critically depends on sampling optotypes with replacement, can be valid for various acuity charts. Nonlimiting examples of these acuity charts includes those using the Landolt C, Tumbling E, HOTV, and Lea optotypes, at least.

In some embodiments, for acuity chart designs that sample optotypes without replacement, like ETDRS, an additional factor is required for the calculation of the family of multiple-optotype psychometric functions. This additional factor may correct for the gradual reduction in available optotypes that occurs when optotypes are sampled without replacement, particularly as the response sequence progresses to the end of the line on the chart.

In some embodiments, the family of multiple-optotype psychometric functions is used to generate the chart-specific psychometric function, which determines the expected number of optotypes correctly recognized per line on the acuity chart, as a function of optotype size. The chart-specific psychometric function, in some cases, represents the weighted sum of the family of multiple-optotype psychometric functions. As show in FIG. 6C, the chart-specific psychometric function 606, E(s), may be specifically calculated as a weighted sum, weighing each multiple-optotype psychometric function 605 by the number of optotypes correctly recognized:

$$E(s) = E_{m=0}^{n}(m \times P_m(s))$$

In some embodiments, weighting of each psychometric function of the family of multiple-optotype psychometric functions 605, 805 may be determined manually by a user or automatically by a computer program. In some embodiments, weighting may be based on information of the subject tested, such as demographic information, previous acuity test results, and/or medical history.

Similar as the single-optotype psychometric functions 604, 804 and/or multi-optotype psychometric functions 605, 805, such chart-specific psychometric function 606, 706 can be determined by two chart-specific acuity model parameters 701, 703, that can provide the critical acuity metrics for characterizing vision:
   a. chart-specific threshold, which defines the optotype size at which the expected number of correctly recognized optotypes meets a pre-defined criterion of visual performance; and
   b. chart-specific range, which defines the difference (in log MAR) between the optotype sizes that respectively define acuity performance at two levels: one above and one below the threshold performance level.

As a non-limiting example, in the case of the standard ETDRS chart, the chart-specific psychometric function 606, 706 is defined by two acuity chart-specific parameters:
   a. acuity threshold, which defines the optotype size providing an expected value of 3 correctly recognized optotypes out of 5; and
   b. acuity range, which defines the number of optotype lines (0.10 log MAR per line) that separate the sizes providing expected values of 1.5 and 4.5 correctly recognized optotypes out of 5.

In the case of the Snellen Chart, the chart-specific psychometric function can be defined by the same parameters as the ETDRS chart, (acuity threshold and range defined in sensitivity units) two issues require consideration—the Snellen chart does not have the same number of optotypes on each line; and only one line on the Snellen chart has the same five optotypes as the ETDRS chart. Therefore, the translation between chart-invariant sensitivity-based functions and chart-specific psychometric functions must be done independently for each line of the Snellen chart that has more or less than the 5 optotypes used by the ETDRS chart.

In the acuity model, the acuity metrics—acuity threshold and range—may be derived from the acuity model parameters at the level of the single-optotype chart-specific psychometric function as shown in FIGS. 6A-6B, the single-optotype chart-invariant psychometric function as shown in FIGS. 4A-4B, and/or FIG. 5A, or the chart-specific psychometric function, E(s) as in FIG. 6C and/or FIG. 7A-7B. These functions can provide the visual acuity metric, as a function of optotype size, commonly associated with visual acuity testing. Summary metrics can also be defined at the level of the multiple optotype functions, but they are naturally harder to interpret.

In some embodiments, another important formulation of the acuity model is defined by chart-invariant model parameters, which define an alternative formulation of the single-optotype psychometric function, which may:
   a. complement the initial formulation of the acuity model which yields chart-specific metrics of vision;
   b. follow the same calculation steps as chart-specific metrics: from single-optotype to multi-optotype to chart-specific psychometric function, but includes an additional preparation step that precedes the single-optotype psychometric function.

In some embodiments, the additional preparation step involves an application of signal detection theory to determine acuity threshold and range parameters on the sensitivity scale (d'), and a corresponding translation of a single-optotype sensitivity psychometric function to a single-optotype psychometric function, which is based on task-based chart features that include the number of guessing alternatives.

The transformation from the sensitivity(d')-based psychometric functions to chart-specific single-optotype psychometric functions can be based on Signal Detection Theory that incorporates the design features of acuity chart design. Given the same level of sensitivity threshold (the optotype corresponding to d'=1), the correct recognition performance level for single optotypes can vary from between 30-40% correct for an identification task with ten alternatives to 70-80% for an identification task with two alternatives.

In some embodiments, the chart-invariant model proposes and helps address that certain reductions in visual performance can be caused by the design features of an acuity test that are not strictly related to visual factors.

In some embodiments, the chart-invariant model provides an account of probabilistic behavior, in which the acuity performance observed in an acuity test reflects dual, independent contributions of sensory and decision processes. In some embodiments, the chart-invariant model proposes that chart-specific or empirical thresholds on psychometric functions are dependent on the number of guessing alternatives. For example, observing a performance of 60% correct recognition when subjects are presented with an acuity chart that samples an optotype set with ten alternatives is not equivalent to 60% correct recognition when sampling a set of four alternatives.

In certain embodiments, the chart-invariant model proposes that a threshold definition for correctly recognizing 3 of 5 optotypes depends on the number of total optotypes being sampled. For statistical reasons, independent of the power of sensitivity of the detecting system, it may be easier to correctly recognize 3 of 5 letters when there are four alternatives for each optotype, rather than ten alternatives.

In certain embodiments, the chart-invariant model makes an important distinction for factors that depend on the acuity test, and factors that depend on the observer/subject, the performance of the observer/subject in the acuity test. Sensitivity regards to visual performance, and other detection level factors are related to acuity test factors and guessing behavior.

In some embodiments, more alternatives for optotype recognition provide more opportunities for incorrect guessing of optotypes and reduce recognition performance.

In some embodiments, chart-specific acuity thresholds or traditional acuity threshold are confounded/contaminated by guessing behavior. In some embodiments, changes in recognition performance reflect factors of acuity chart design. For example, with acuity chart designs with fewer alternatives, correct guessing is more probable. Increasing the number of alternatives may reduce recognition performance based on factors that are unrelated to vision. To account for guessing behavior confounds on recognition performance, Signal Detection Theory proposes equations that translates between the chart-specific behavior (defined by % correct) to chart-invariant behavior (defined in units of sensitivity: d').

In some embodiments, the chart-invariant model defines acuity metrics using the chart-invariant psychometric function, which describes sensitivity (d') as a function of optotype size. This function, which does not depend on the specific acuity chart design used to collect data from the test subject, and such model can be defined by: chart-invariant sensitivity threshold—the optotype size (in log MAR) which corresponds to d'=2.0; and chart-invariant sensitivity range—the differences between the optotype sizes (in log MAR) corresponding to d' values of 1.0 and 3.0.

The utility of a sensitivity-based approach can be supported by the observation that visual acuity measured with the HOTV (with only four alternatives) is better than acuity measured with the Sloan Set.

Algorithm S may concurrently estimate chart-specific and chart-invariant acuity metrics. An advantage of visual acuity metrics, either the chart-specific or chart-invariant metrics is that both sets of acuity parameters are interchangeable and inter-translatable.

The acuity model herein can provide novel predictions of acuity chart performance and represents a data-generating mechanism for the model inference of acuity metrics. The model can use only acuity threshold and acuity range parameters to predict a rich set of relationships between optotype size and the performance observed during testing with acuity charts.

The acuity model may analyze acuity chart performance by evaluating how probabilities for correctly recognizing multiple numbers of optotypes change as a function of optotype size.

In some embodiments, the acuity model provides a fine-scale analysis of acuity chart performance that provides a superior account for the probabilistic behavior observed near acuity thresholds. The acuity model may be more robust to the random factors that can affect the termination criteria that are currently in practice in acuity testing. The acuity model may be more robust to the probabilistic behavior that occurs near threshold: e.g., due to random effects, when a subject is presented with optotypes at the sizes near the acuity threshold 501, e.g., chart-specific acuity threshold, it is nearly equally likely to observe 2, 3, or 4 correctly recognized optotypes (e.g., FIG. 5). The acuity model can be versatile and flexible: for acuity chart designs that changes the number of optotypes per line, as the Snellen chart does, the predictive model generates different multiple-optotype psychometric functions for different lines. The acuity model may ultimately be applied to the acuity chart data, to infer the acuity model parameters that describe the test subject's vision. The acuity model can be defined to remove bias from the Snellen Acuity Chart. Despite its use in many clinical settings, the Snellen has been replaced in ophthalmic trials because it cannot be scored in the same way as the gold standard. The acuity model may accounts for confounds between Snellen, ETDRS, HOTV, and any acuity chart design.

Although the acuity model can be defined concisely with only two acuity parameters, the model is also flexible enough to generate acuity metrics that are chart-specific, which describe performance based on specific acuity charts an acuity metrics that are chart-invariant, which describe performance independently of the acuity charts used to collect data.

In some embodiments, for algorithm S to score acuity chart data, each line entry of an acuity chart data table signifies the reading of a single optotype or single line of optotypes from a visual acuity chart or sub-chart. Each line of optotypes can be considered as a composite stimulus, is determined by at least one of the following changing conditions: a number of optotypes sampled per line, a number of potential optotypes being sampled from (i.e., the number of optotype in a library), and whether sampling from the optotype set is with or without replacement. The response entry in the summary table is the number of correctly recognized optotypes, whether for a single optotype or a single line of optotypes. In this case, the response is a ratio calculated by the number of correctly recognized optotypes divided by the total number of optotypes of the same line/row.

In some embodiments, at least one acuity model is used to calculate visual acuity parameters. In some embodiments, Bayesian adaptive estimation is used to calculate visual acuity parameters. In certain cases, two-dimensional Bayesian probability density function over two sensitivity parameters is used to calculate the visual acuity parameters. In some embodiments, Bayes' rule is used to calculate visual acuity parameters. In some embodiments, at least one probability function is used to calculate visual acuity parameters. In further embodiments, the prior probability of getting response r given acuity parameters $d_{1,x}$ and $d_{2,y}$, $P(r_z|d_{1,x}, d_{2,y})$ is used to calculate visual acuity parameters, wherein x and y are integers between 1 and the maximal number of parameter $d_1$, m, and parameter $d_2$, n, respectively, and wherein z is an integer between 1 and the maximal number of responses, i. In some embodiments, the probability of having different acuity parameters $p(d_{1,x}, d_{2,y})$ and/or the probability of getting different responses, $p(r_z)$. In some embodiments, the posterior probability function, $p(d_{1,x}, d_{2,y}| r_z)$, represent the visual acuity, wherein $p(d_{1,x}, d_{2,y}| r_z)=[p(d_{1,x}, d_{2,y})p(r_z|d_{1,x}, d_{2,y})]/\Sigma\ p(d_{1,x}, d_{2,y})p(r_z|d_{1,x}, d_{2,y})$. wherein $\Sigma\ p(d_{1,x}, d_{2,y})p(r_z|d_{1,x}, d_{2,y})$ represents the sum wherein x takes any integer value between 1 to m, y takes any integer value between 1 to n, and z takes any integer value between 1 to i.

To update or generate a test slide in a next test run, in some embodiments, the entropy of the pdf, $p(d_{1,x}, d_{2,y}| r_z)$, is calculated over the space of sensitivity parameters. In some embodiments, the entropy $H(r_z)=\Sigma\ p(d_{1,x}, d_{2,y}| r_z)\log(p(d_{1,x}, d_{2,y}| r_z))$, wherein $\Sigma$ represents the sum wherein x takes any integer value between 1 to m, y takes any integer value between 1 and n, and z takes any integer value between 1 to i.

In some embodiments, at least one principle related to visual chart design is used as input to the statistical model. In some embodiments, at least one principle is selected from: a number of lines presented on each test chart or subchart, a number optotypes presented on each line of the test chart or subchart, the total number of optotypes within the library of optotypes; and whether sampling from the optotype library is done with or without replacement.

The acuity model herein may incorporate at least part of the full defining details of acuity chart design, for example, the five optotypes presented per line. In some embodiments, the primary acuity metrics provided by the acuity model herein is the chart-specific acuity threshold, e.g., 701, which may represent the optotype size (or equivalently, a line on the chart) at which subjects correctly recognize three of five optotypes per line (or some other specified performance criterion that defines the threshold).

Predict Acuity Chart Data, Given Candidate Parameters

In some embodiments, the acuity model is applied to generate a series of tables that contain predictions of the probabilities of observing the collected acuity chart data, given candidate acuity model parameters, as shown in operation 500 in FIG. 1.

For each acuity chart condition or row in Table 1, a table of candidate parameter combinations, in which the first entry is the candidate parameters, and subsequent entries are the predictive probabilities of the observed composite response are shown in Table 4. For each acuity chart condition delineated in the table shown in Table 1, the probability of observing that response is calculated for the complete set of candidate parameters. In some embodiments, for each row in Table 2, a table for the full set of candidate parameters as Table 4 can be generated.

Table 3 presents the set of candidate acuity parameters and their prediction of the acuity chart data collected from the test subject, for a single test condition (i.e., "Data Entry" of 1 of response r1 in Table 2).

TABLE 3

| Data Entry | Model Entry | Acuity Threshold | Acuity Range | Predicted Probability of Observed Response $P(r; \alpha, \beta, s)$ |
|---|---|---|---|---|
| 1 | 1 | $\alpha_1$ | $\beta_1$ | $P_1(r_1)$ |
| 1 | 2 | $\alpha_2$ | $\beta_2$ | $P_2(r_1)$ |
| 1 | 3 | $\alpha_3$ | $\beta_3$ | $P_3(r_1)$ |
| . | . | . | . | . |
| . | . | . | . | . |
| . | . | . | . | . |
| 1 | $q_0$ | $\alpha_{q1}$ | $\beta_{q2}$ | $P_q(r_1)$ |

(Candidate Acuity Model Parameters spans Acuity Threshold and Acuity Range columns)

Each table represents the candidate set of acuity parameters, and their probability estimates of the observed response for that chart or subchart condition. In this case, q0 equals q1 times q2. For a single data entry, optionally there are multiple candidate acuity model entries. In some embodiments, each full acuity chart dataset includes a plurality of data tables. In some embodiments, analysis of a full acuity chart dataset involves generating a plurality of data tables, and in each table, one for each chart condition is described by a line of the data table, which correspond to operations in flow chart in FIG. 17. In this case, the probability of observed response is calculated. In other words, the probability of generating a single response, r1, given the acuity parameters, i.e., $\alpha 1$ and $\beta 1$, and the stimulus parameters delineated in S1.

Evaluate and Rank Candidate Parameters for Acuity Model

In some embodiments, following the generation of the full series of tables, e.g., Table 3, a new summary table can be calculate, as shown in operation 600 of FIG. 1.

In the series of tables of candidate parameters and predicted probabilities of observed responses, each row may summarize the presentation and response of a single optotype or a single line of optotypes. The entry position in each table across the whole series of tables may correspond to a single pair of candidate acuity model parameters. The same entry position in each table may correspond to the same combination of candidate parameters across the series. Each table in the series corresponds to the predicted probability of observing the single or composite response to the optotype size condition described on that row of the table, for the full set of candidate parameters.

In some embodiments, the acuity chart data represented in the full series of tables is summarized by consolidating the series of tables into a summary table. In some embodiments, the serial multiplication across the full series of tables, of the predictive probability values in corresponding entry positions, provides a summary probability of observing the full set acuity chart data, for those specific candidate parameters. The new summary table is calculated by the serial multiplication of multiplying all the corresponding for all the rows summarized in the summary table, the corresponding entries are multiplied, and a new table is generated, as shown in Table 4. The series of tables may be consolidated into a summary metric. In some embodiments, the serial multiplication provides a likelihood estimate for the candidate acuity model parameters, given the observation of the full set of the acuity chart data. In some embodiments, the resulting summary table represents an evaluation of the candidate parameter estimates, based on the observed chart data. In some cases, the resulting summary table represents a likelihood calculation of candidate parameters, as a function of the data. In some cases, the resulting summary table represents a calculation of likelihood over candidate acuity parameters as a function of the acuity data, which can be combined with a calculation of a prior probability function over candidate acuity parameters, as in Bayes rule. In some embodiments, the prior probability function can be determined by information of the subject such as the subject's age, status of eye disease, status of neuropathology that affects vision, or previous visual assessments.

Table 4 shows aggregate probability of multiple responses from a test object based on different candidate acuity model parameters and acuity models. This table can be used to score data retrospectively by first predicting acuity chart data, and then ranking the acuity model parameters given the composite response for their predictive quality and/or goodness-of-fit. This table can also be applied prospectively to actively improve the collection of acuity chart data.

As shown in Table 4, the set of candidate acuity parameters and their prediction of the acuity chart data collected from the test subject are presented, for a single test condition (Data Entry 1). Analysis of a full acuity chart dataset may involve generating a series of these tables, one table for each chart conditions described by a row of the data summarized in Table 1. Each table may represent the candidate set of acuity parameters, and their probability estimates of the observed response for that chart or subchart condition.

Optionally, the probability of responding to a test with responses of r1 to rk, given the acuity threshold and acuity range/slope, is calculated and presented in the ranking table. In this case, the ranking table optionally ranks the aggregate probability of responses, for example, p((r1, r2, . . . , rk); $\beta 1$, $\beta 1$), given a set of acuity parameters. In this embodiment, the acuity parameter set with the highest ranking is the estimated acuity based on given responses in a test.

TABLE 4

| Acuity Model Entry | Candidate Acuity Model Parameters | | Probability of Response Aggregate $\prod_{i=1}^{k} P(r_i; \alpha, \beta, s_i)$ |
|---|---|---|---|
| | Acuity Threshold | Acuity Range | |
| 1 | $\alpha_1$ | $\beta_1$ | $P((r_1, r_2, \ldots r_k); \alpha_1, \beta_1)$ |
| 2 | $\alpha_2$ | $\beta_2$ | $P((r_1, r_2, \ldots r_k); \alpha_2, \beta_1)$ |
| 3 | $\alpha_3$ | $\beta_3$ | $P((r_1, r_2, \ldots r_k); \alpha_3, \beta_1)$ |
| . | . | . | . |
| . | . | . | . |
| . | . | . | . |
| q | $\alpha_{q1}$ | $\beta_{q2}$ | $P((r_1, r_2, \ldots r_k); \alpha_{q1}, \beta_{q2})$ |

Estimate the Acuity Model Parameters that Describe the Test Subject

Table 4 shows all the candidate sets of acuity parameters of Table 3, and the probability of observing a composite response as the acuity chart data collected in Table 2, calculated over those candidate acuity parameters.

Given the table of likelihood values, i.e., probability of response aggregate, as shown in Table 4, the serial ranking of likelihood values (e.g., from highest to lowest) may provide the equivalent of a maximum likelihood analysis. As shown in operation 700 in FIG. 1, choosing the highest-ranking values and the corresponding candidate acuity model parameters in the sorted table can yield maximum-likelihood estimates of acuity model parameters. Alternatively, if prior information, such as demographic information, or results from a previous vision test are used to weigh the serial multiplication, the sorted ranking may correspond to a weighted likelihood or Bayesian parameter estimation.

In some embodiments, prior information can include but is not limited to age, risk of genetics, results of previous vision testing, the results of previous disease diagnosis, or any other physiological or medical information of the subject. If the table is normalized to sum to 1, then the prior information table reflects a Bayesian inference. With normalization, the table represents a Bayesian probability distribution which can be defined by its mean, median, or mode. In addition to these statistics and metrics of central tendency (e.g., mean, median, mode), there are statistical measures of the spread or dispersion or variability of the Bayesian posterior probability (Is this correct?) function defined over the candidate parameters of the acuity chart model. In some embodiments, evaluation and ranking of acuity model parameters includes the standard deviations, or percentiles of the acuity model parameters. In some embodiments, evaluation and ranking of acuity model parameters includes statistical inference (maximum-likelihood, Bayesian, or any other applicable methods), which yields acuity metrics via acuity parameter estimates, given the observed acuity data and the model-generated predictive probabilities for acuity performance. In some embodiments, evaluation and ranking of acuity model parameters involves statistical inference of acuity threshold and range parameters that best describe the acuity chart data collected from the test subject.

To yield visual acuity parameters that are either chart-specific or chart-invariant, the systems and methods herein may include one or more sub-steps for analysis and inference:
1. Generate a table that describes the candidates for the acuity threshold and/or range parameters, e.g., Table 2.
2. For these candidate parameter combinations, and given defining features of the acuity chart design, a predictive model for scoring acuity chart behavior can be constructed
3. Given responses to single-optotypes or multiple-optotypes determined by acuity chart design (e.g., acuity test data or acuity chart data), statistical inference can be accomplished by a maximum-likelihood or Bayesian analysis that provides estimates of acuity parameters
4. Considering the number of lines of optotypes that were presented during the acuity chart test, and considering the optotype size and response observed on that trial
5. Is started by considering a parameter space, which includes the acuity chart design parameters for the range of single-optotype sizes
6. Defining parameters in sensitivity(d')-based functions, based on Signal Detection Theory
7. The scoring model in Step 2 is used to generate predictive probabilities for parameter estimation which is done either by maximum likelihood or Bayesian estimation
8. Given a model that predicts the probabilities of observing patterns of acuity chart data
9. The generic model for analytics comprises three sets of values that can be organized in tables:
10. To build the analytics framework, three tables are important:
    a) Data Collected from Subject, e.g., Table 1
    b) Candidate Acuity Model Parameters, e.g., Table 2
    c) the corresponding table of probabilities defined by candidate acuity parameters: For the table of probabilities, for each stimulus-response combination collected during acuity testing—the size of the optotypes presented on the line of the chart and the number of optotypes correctly recognized, e.g., Table 4.
11. Generate candidate psychometric functions, with predictive probabilities of response outcomes, as a function of optotype size
12. For each optotype size presented during the test, the predictive probability for observing that response is calculated for at least a part of the candidate acuity parameters.
13. For each optotype size presented on each line of the chart, a different table presents the predicted response probability.
14. The methods and systems for scoring may yield two acuity metrics: the threshold and range of the chart-invariant psychometric function.
15. Through Bayesian inference, the estimates of the acuity metrics, in addition to confidence in their estimates, can be provided, or through maximum likelihood, the estimates of the acuity metrics can be provided.

Determine a Set of Candidate Charts for Potential Collection of Acuity Chart Data from Test Subject In some embodiments, a set of candidate acuity charts may be evaluated based on their capability of providing the potential conditions for collecting acuity chart data, as shown in FIG. 10. In some embodiments, this analysis estimate the probabilities of observing prospective acuity chart data, evaluate how those outcomes analyses determine the test conditions under which acuity chart data should be collected. In some embodiments, due to the generality of the acuity model, the set of candidate acuity charts can include any acuity chart design. In other cases, to adhere to the recommendations of standards committees, the most common approach to define the set of candidate charts may be defining acuity charts that follow the same design principles as existing charts, for example, log MAR charts (ETDRS, Bailey-Lovie), Snellen charts, Sloan low-contrast charts, and/or sub-charts of log MAR or Snellen (Single-line or single-optotype)

In some embodiments, the principles of acuity chart design include properties of the optotypes presented on the acuity chart:
  i. Size of optotype set to be sampled;
  ii. Number of optotypes presented per line;
  iii. Number of optotype lines presented per chart;
  iv. Optotype sampling method; or their combinations.

Although the set of candidate charts follow the same general design principles as the prior art for standard acuity charts, the candidate charts may be constructed with a finer resolution and wider range for sampling optotype size. (FIGS. 11A-11F, and/or FIG. 12) Each individual chart may demonstrate the same precision for sampling optotype size as the prior/current art, but taken together, the set of candidate charts may exhibit a much higher precision for sampling optotype sizes than any existing art in the field. This expanded library of acuity charts may improve the precision and expand the flexibility for sampling optotype size.

Figures 11A, 11B, 11C, 11D, 11E, 11F:
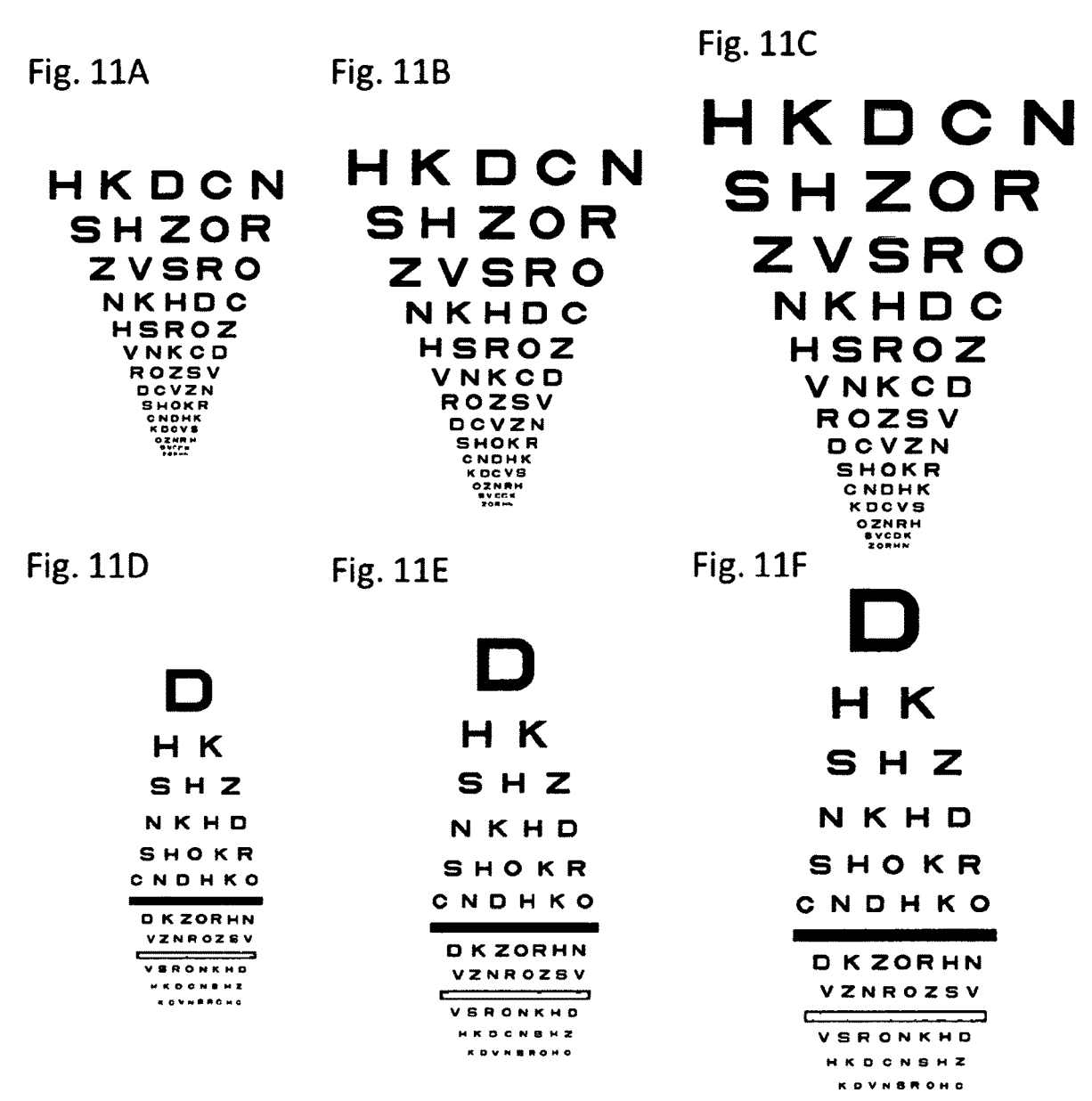

To improve the sampling resolution for optotype size in visual acuity tests, while strictly conforming to visual acuity design standards and principles, disclosed herein is a method for producing an expansive library of visual acuity charts, as shown in FIGS. 11A-11F. FIGS. 11A-11C show the exemplary sampling scheme represented by ETDRS standard chart, which presents fourteen standard sizes of optotypes from −0.3 to 1.0 log MAR, with 0.10 log unit sampling resolution between successive sizes. In these embodiments, the anchor point of 0.35 log MAR represents the mean optotype size of the ETDRS standard chart. By changing the anchor points of a standard-constrained chart to produce a larger, complementary set of acuity charts, the resolution for sampling optotype size may be greatly improved across the collection of charts, while preserving the adherence of individual charts to acuity chart standards.

In some embodiments, a set of ten acuity charts, produced by changing the anchor point of a standard chart within the range of 0.3-0.4 log MAR, with an anchor point resolution of 0.01 log MAR. Each chart uses the same sampling resolution as the standard. However, when the entire set of design-constrained charts is considered, these charts provide the fine resolution of optotype size. Considered collectively, this set of 10 charts exhibits higher sampling resolution for optotype size (0.01 log unit) and over a wide range of 141 different optotype sizes.

As an example, the ETDRS chart design comprises fourteen lines of optotypes, five optotypes per line, with a logarithmic reduction in size with each descending row. The 0.10 decimal log unit progression provides an approximately 25% reduction in size with each successive row of optotypes. These design elements may be maintained in a library of charts with different optotype sizes (FIGS. 11A-11C), which follow the constraints of these design elements. An example subset of a library of design-constrained visual acuity charts, which was produced using ETDRS design principles (FIGS. 11A-11C) with three different anchor points 0.30, 0.35, and 0.40 log MAR, and Snellen design principles (FIGS. 11D-11F) with three different anchor points.

Shortcomings of these chart designs may relate to the static range and resolution for sampling optotype size. Due to a non-adaptive, deterministic testing routine, all patients are presented with the same range of optotypes. Furthermore, the invariant sampling resolution of the test results in insensitivity to measuring acuity values that correspond to optotype sizes that are intermediate, relative to those presented on the fourteen established optotype sizes.

As shown in FIGS. 12A-12C, visual acuity testing can be optionally performed with sub-charts, which represent focused testing of specific regions of a chart. A sub-chart can be sub-sampled from a full design-constrained acuity chart, by presenting only a restricted set of optotypes from a full acuity chart, which is in turn a subsample of the greater library of design-constrained charts. Rather than present the full 14 rows of the ETDRS chart, presenting a set of subcharts can focus vision testing to a spatial subsample of the full chart (e.g., 3 rows of optotypes). The target letters of the focused visual acuity test can be distinguished by (FIG. 12A) presenting only the sub-sampled region of the full chart (FIG. 12B) presenting the sub-sampled region at a high contrast, relative to the low contrast of the rest of the chart, or (FIG. 12C) presenting only the sub-sampled region without blur, and blurring the rest of the chart.

Evaluate and Rank Candidate Acuity Charts, Given Ranking of Candidate Parameters for Acuity Model In some embodiments, given those candidate parameters, a table of predictive probabilities for the potential outcomes for each line of the acuity chart may be constructed. The ranking of acuity model parameters is inherent in the probability distribution defined over model parameters.

For the adaptive algorithm to personalize and focus testing to an individual patient, it may be necessary to calculate a ranking over the set of candidate acuity charts. It may also be necessary to derive and calculate a utility function that is used for ranking. Acuity charts can be evaluated and ranked according to different criteria. In some embodiments, acuity chart designs are evaluated for their utility in testing a given subject. The utility function may include one or more of the following: active learning, variance minimization, entropy minimization, maximum information gain, information gain of chart-specific parameters, information gain of the chart-invariant parameters, or a combination thereof.

The existing art (which includes the QUEST method) only calculates design optimization for a single optotype. One advantage of the systems and methods disclosed herein is a ranking of acuity chart design over single optotypes, single lines of multiple optotypes, or full charts of optotypes. The goal of this ranking process is personalization of the test to the specific subject, via the selection of optimal or near-optimal (e.g., high ranking charts or subcharts) acuity charts or sub-charts. In some embodiments, compound optimization refers to the optimization of more than one optotype, with the compound or ensemble optotype set presented over a chart or subchart. A compound utility function may be calculated over the entire acuity chart design. The compound stimulus optimization allows the optimal design selection of the acuity chart, rather than single letters. The optimization is calculated for each component of the compound stimulus. Optimal design may be selected based on a chart or subchart. In this case, the utility function is calculated for each component of the compound and then summed.

Algorithm A may provide a prospective, predictive analysis of the optimal acuity chart(s) that should be used to collect acuity chart data from a test subject. To compare, algorithm S may provide a retrospective analysis of acuity chart data collected from a subject. The principle that underlies algorithm A is optimal design selection: analyzing the set of candidate charts to find the best chart(s) to collect acuity chart data for the specific subject.

To rank acuity charts, a utility function can be calculated over the set of candidate charts. Algorithm A may select the acuity charts that focus on the specific test subject. It does so optionally by evaluating, ranking, and selecting the candidate acuity charts that are optimal for collecting acuity chart data. Optimal design selection can be calculated on chart-specific or chart-invariant parameters. In some embodiments, the adaptive acuity chart optionally includes a combination of algorithms S and A. Relative to the post-hoc testing of algorithm S, the advantage of algorithm A is to "close the loop" between scoring and testing stages. Algorithm A may improve precision through re-iterative testing, scoring, and re-testing of acuity metrics.

For acuity testing with adaptive acuity charts, the optimal design selection accomplished by algorithm A may be calculated by a computationally-intensive process that looks ahead to predict the outcomes of the next trial in the test, and evaluates the best acuity chart design for that trial of the test. The scoring algorithm may be applied after every trial of the test. In addition, the acuity model and scoring may be applied to evaluate the potential outcomes of the next trial. In this case, an acuity test may include multiple trials and in each trials, one or more response from the test subject is collected.

In some embodiments, the ranking of candidate charts can be used to select a personalized acuity sub-chart (e.g., with highest rank(s)). In this embodiment, the candidate charts may comprise three lines with standardized progression of 0.10 log units between lines. To simulate the detection of a change of acuity (0.10 log unit/five letter difference), e.g., between two medical conditions, the relative patterns of optimization can be presented for the two medical conditions. The relative shift in the utility function reveals the precision of the combination algorithm for personalizing acuity testing, and for detecting subtle changes in vision.

Figures 14A, 14B:
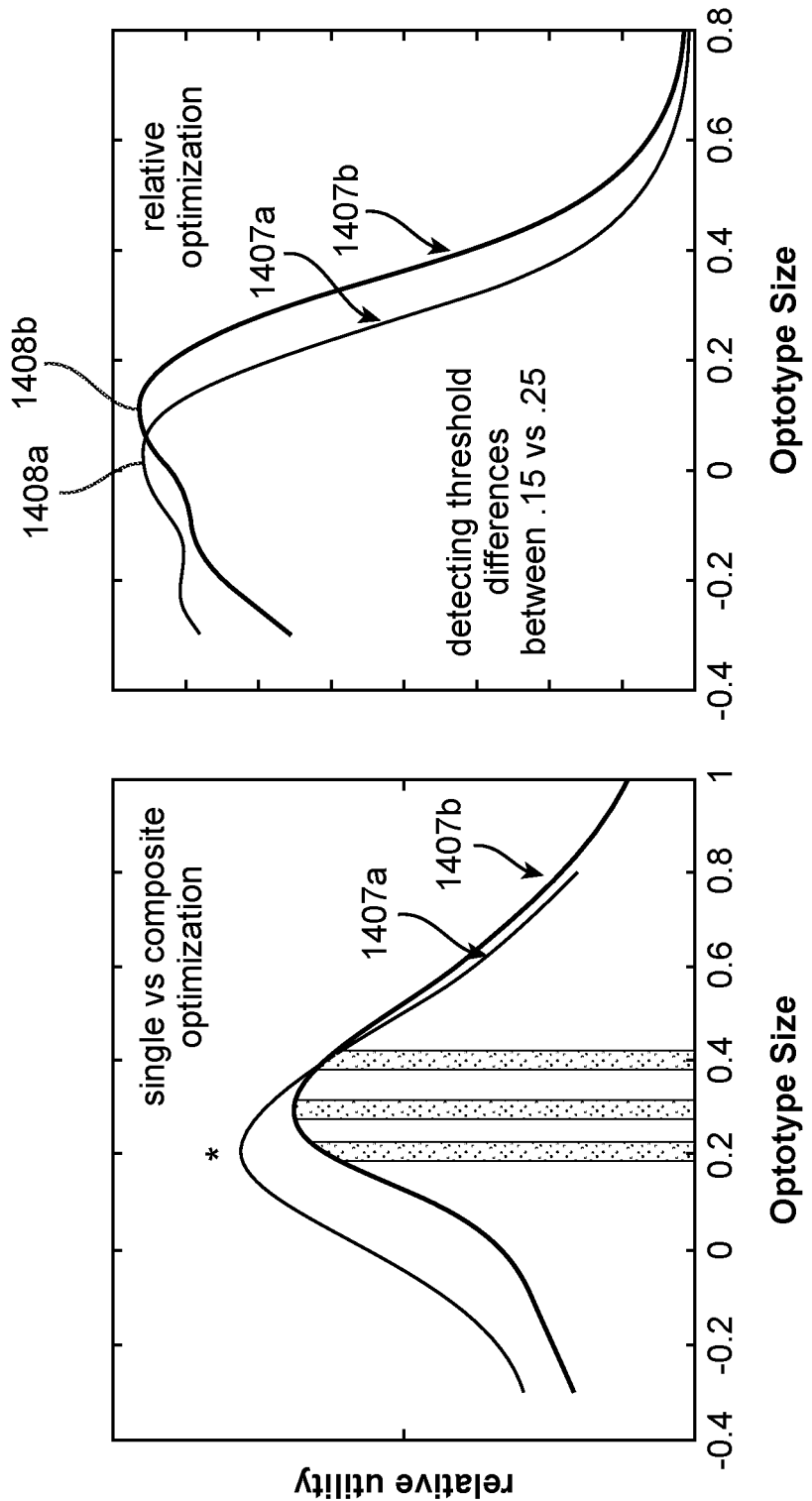
FIG. 14A-14B show a non-limiting example that compares the results for calculation of single-line optimization with composite multi-line subchart optimization.

In some embodiments, with a selected utility function, e.g., 1407a, 1407b, which varies with change of optotype size, the candidate chart(s) can be evaluated based on their corresponding utility value(s) and a ranking may be generated for each of candidate charts. A high-ranking acuity chart can provide high utility value (e.g., of arbitrary unit) and may be used for testing, and a low-ranking chart is less useful and may not be used for testing. The advantage of using a compound utility function 1407a to select high-ranking acuity sub-charts vs using a single utility function 1407b is demonstrated in FIG. 14A. As shown in FIGS. 14A-14B, a composite utility function 1407a may share a similar curve shape as the single utility function 1407b. However, for same optotype sizes for example in the range from 0.2 to 0.4, the utility values are higher. In addition, peak can be obtained with smaller optotype sizes compared with the single utility function. With the current art, including QUEST method, the utility function and its optimization is based on a single optotype size. When the optimization of a three-line subchart is considered, with a standard-constrained progression in optotype size between lines (represented by the space between the shaded areas), peaks 1408a, 1408b of the utility functions for single vs compound optimization may be apparent at different optotype sizes. As shown in FIG. 14B, in some embodiments, with a selected utility function which varies with the change of optotype size (the utility function is selected to determine whether two conditions exhibit a change in acuity threshold of 0.15 vs 0.25 units), the utility function shows different peaks 1408a, 1408b when the stimulus is a single optotype row or a sub-chart that comprises a compound stimulus of multiple optotype sizes.

Figure 15:
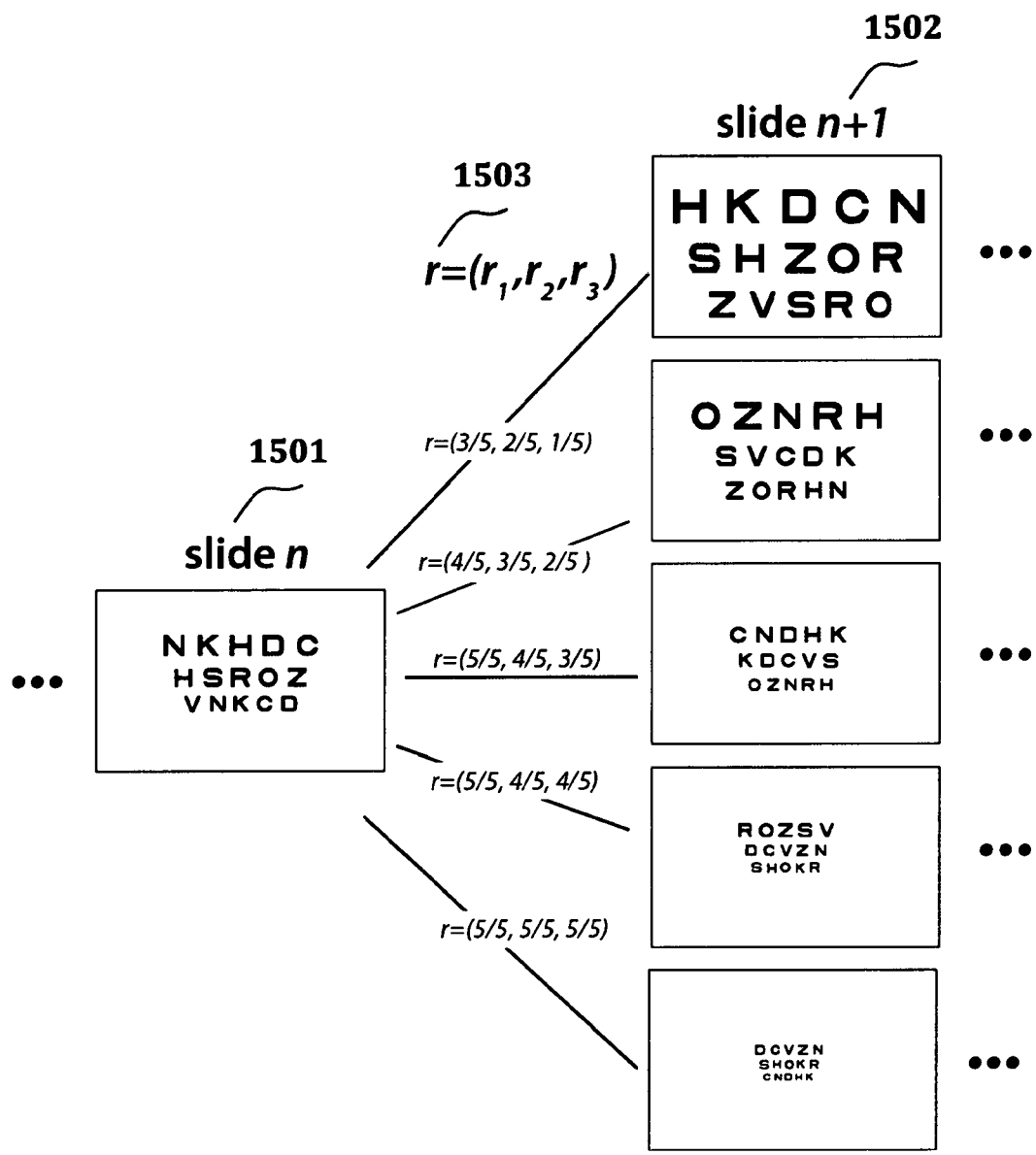
FIG. 15 shows a non-limiting example of the selection of a personalized acuity chart for a sequential test slide (n+1 in the series), based on the response of the subject to the $n^{th}$ test slide.

Referring to FIG. 15, in a particular embodiment, an example of a two-slide sequence from an adaptive standard-constrained visual acuity test is presented. The exemplary slides n and n+1 of a longer sequence are presented, with the branches representing different potential outcomes for the reading of slide n. The branches are not exhaustive, and serve to show a small subset of the potential outcomes for the presentation of slide n 1501. On slide n 1501, the test focuses on the most informative middle region of the ETDRS chart. Following presentation of slide n 1501, which comprises a 3-line ETDRS subchart, the subject responds and response r 1503 is collected. In this case, the compound three-row response describes how many optotypes (out of a maximum five) are correctly reported, for each of the three rows. If the maximum five letters per row are reported correctly on each row (bottom-most branch), then testing on the next slide 1502 may adapt to present a subchart with smaller optotypes. In this embodiments, when the subject's response optionally fall short of correctly reporting all three rows, the subsequent presentation of slides test different regions of the full acuity chart. In this embodiment, the optotype subcharts presented conform to acuity chart design principles: multiple letter lines with a size progression of 0.10 log units. With each subsequent slide, the adaptive testing algorithms focuses testing to the optotype sizes that are most useful for testing each individual's acuity. Precise and fine-grained sampling of optotype size is accomplished while maintaining the 0.10 log unit progression between each line. On each slide, the optotype subcharts, in some embodiments, conform to acuity chart design principles: multiple letter lines with a size progression of 0.10 log units. With each subsequent slide, the adaptive testing algorithms focuses testing to the optotype sizes that are most useful for testing each individual's acuity. Precise and fine-grained sampling of optotype size is accomplished while maintaining the 0.10 log unit progression between each line.

Figure 18:
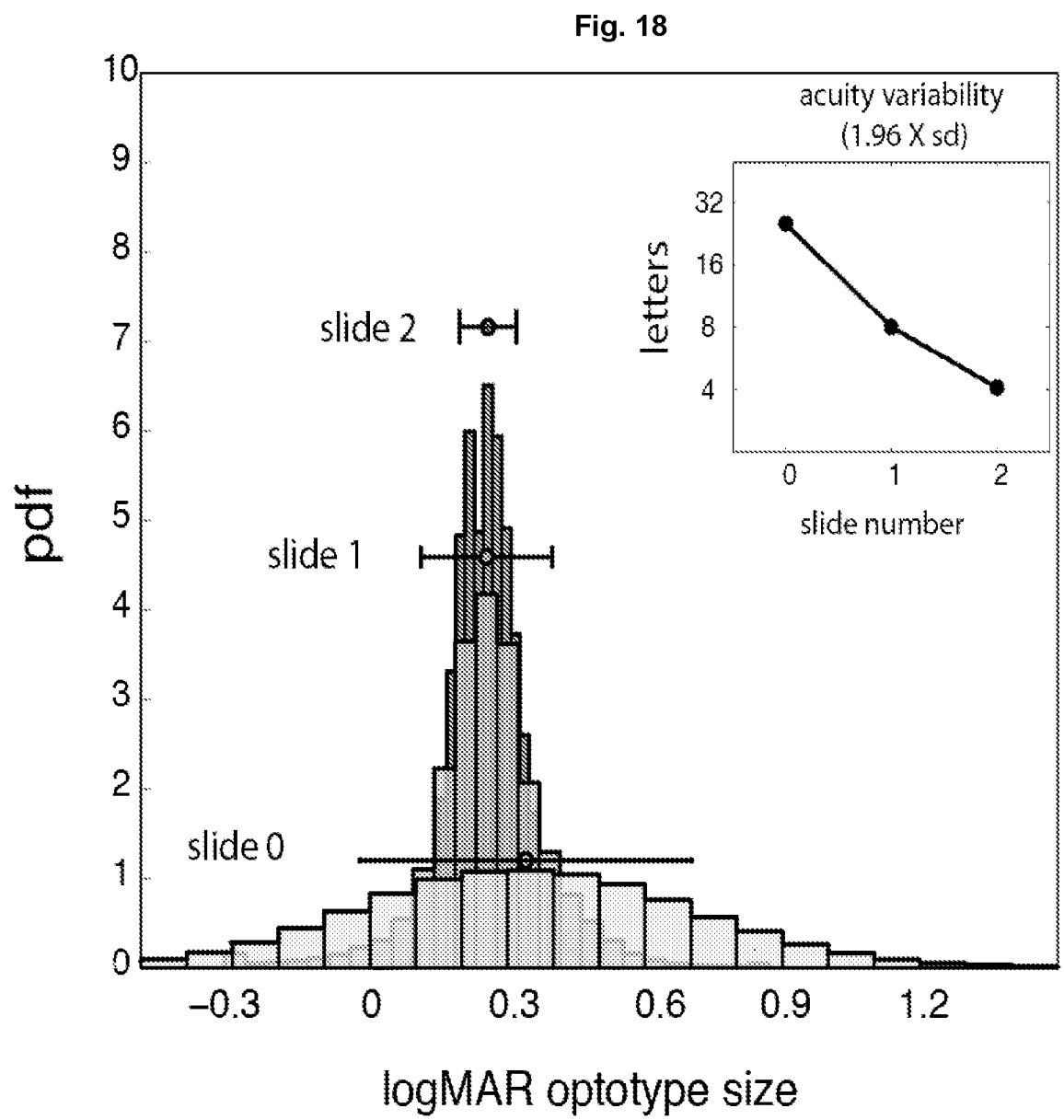
FIG. 18 shows a non-limiting example of estimating the acuity threshold of a subject using Bayesian posterior probability, in this case, using three slides. The insert shows the convergence of acuity estimates with the increase in the number of test slides.

Referring to FIG. 18, in a particular embodiment, the convergence of adaptive acuity testing is reflected in Bayesian posterior probability estimates obtained from a plurality of simulated testing runs using a three-slide test. In this embodiment, the broadest posterior reflects the earliest acuity threshold estimates obtained from the patient's reading of the first column of the full 14-line ETDRS chart shown in slide 0. On the next chart presented on slide 1, the patient is presented with a smaller five-line chart that adheres to ETDRS principles and specifically optimized to the patient. The Bayesian posterior functions that result after presentation of slide 1 reflect the Bayesian update of the parameters of the visual acuity model. Reduction in the dispersion of the Bayesian posterior function reflects the convergence of acuity sensitivity estimation. The inset presents the rapid reduction in test variability with increasing number of test slides.

Figure 19:
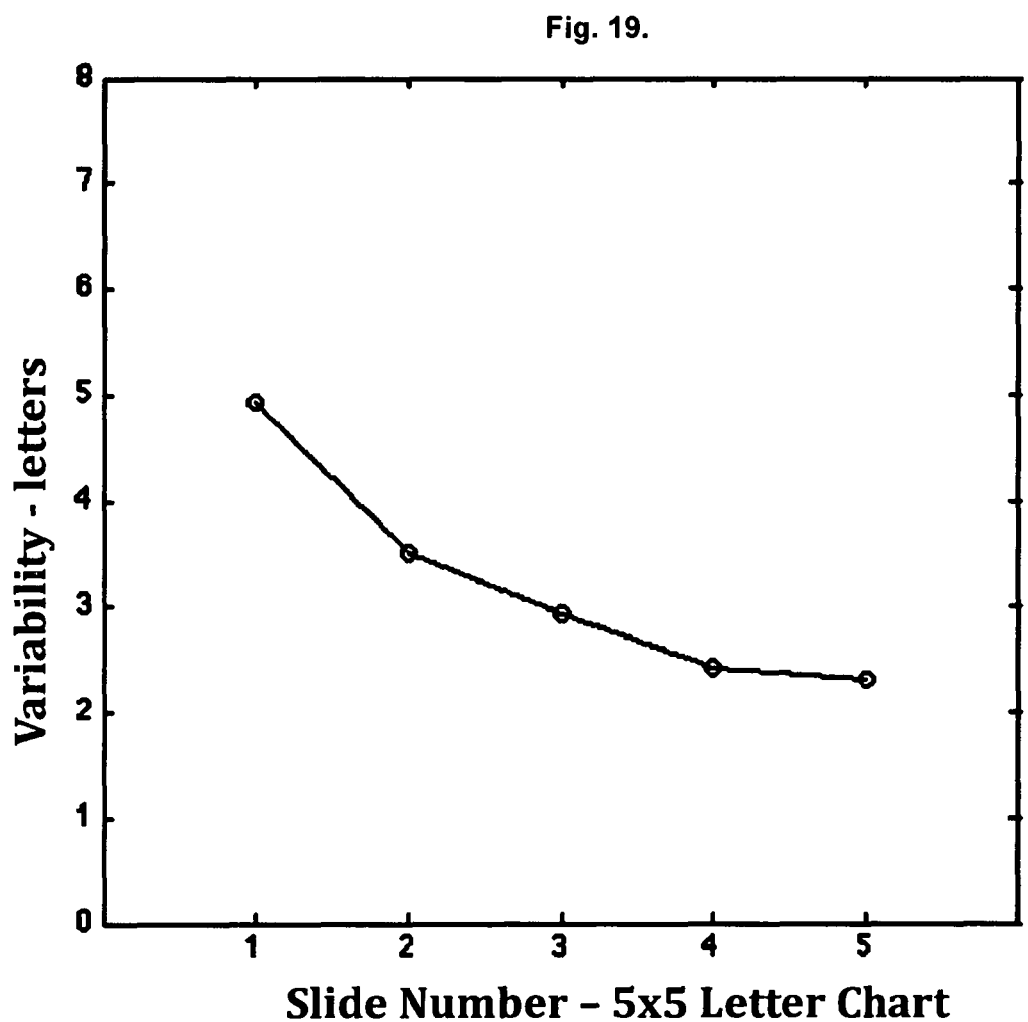
FIG. 19 shows a non-limiting example of variability changes with different number of test slides in a standard-constrained adaptive acuity test with 1 to 5 slides and four different runs for each test.

Referring to FIG. 19, in a particular embodiment, experimental results for adaptive chart-based acuity testing are shown. In this embodiment, a subject with normal vision is tested with standard-constrained adaptive testing that includes 5 test slides in sequence, with each test slide comprising 5 lines, with each line comprising 5 letters sampled from the Sloan set without replacement. In this embodiment, four test runs are completed, and the variability of test results is calculated over multiple runs. Convergence is reflected in the reduced variability of acuity threshold estimates with increasing number of test slides.

Figure 20:
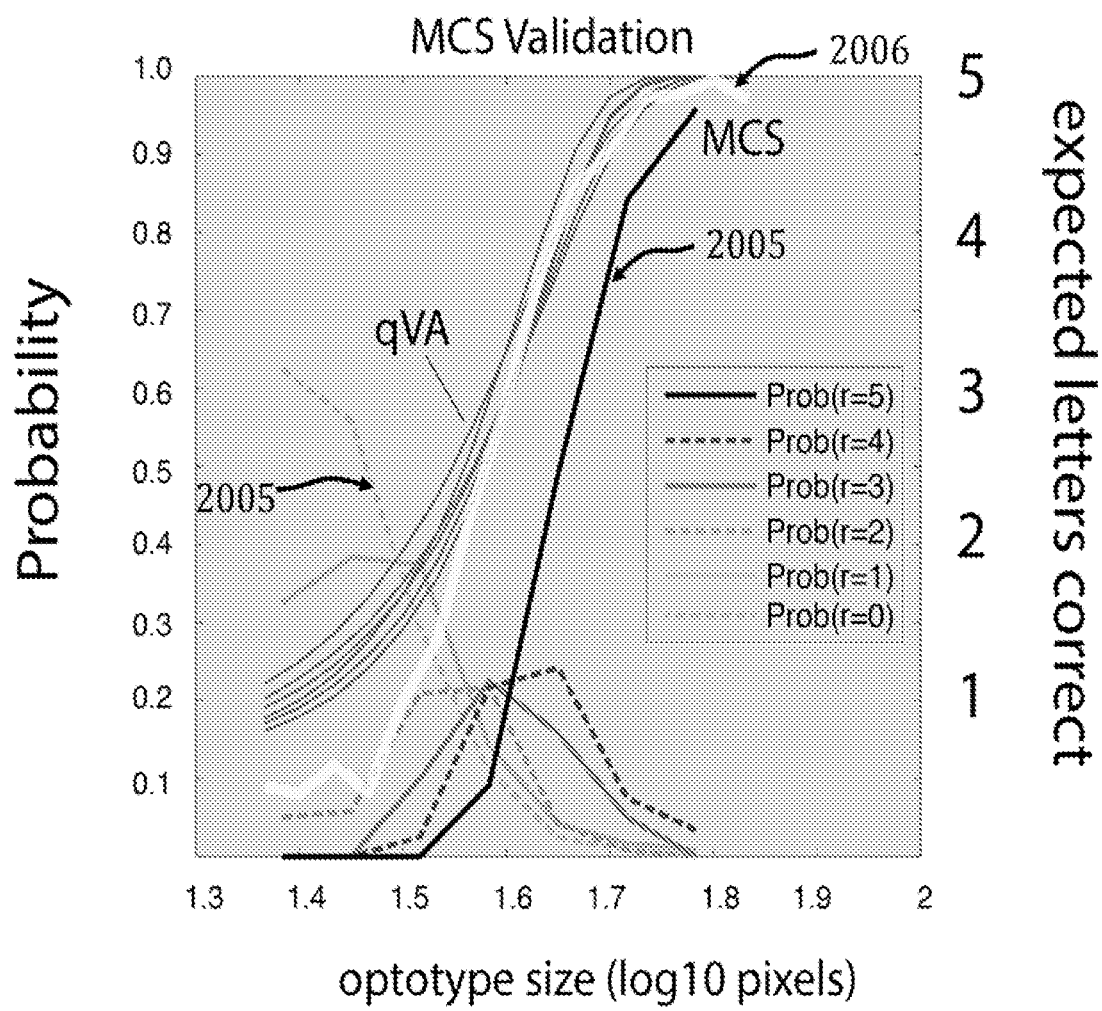
FIG. 20 shows a non-limiting example of validation of the combination algorithm.

Referring to FIG. 20, in a particular embodiment, a subject with normal vision is tested with standard-constrained adaptive testing that includes 5 test slides in sequence, with each test slide comprising 5 lines, with each line comprising 5 letters sampled from the Sloan set without replacement. To validate the functions estimated with adaptive testing, pre-determined stimulus sampling of optotype size (the method of constant stimuli) was used and the probability of correctly reporting different numbers of optotypes (from 0 to 5) was calculated and plotted. Only two psychometric functions exhibit monotonicity. The probability of correctly reporting 0 of 5 optotypes P(0/5), decreases monotonically with increasing optotype size. As optotypes grow large, the probability of reporting correctly none out of five converges to 0%. As a complement, the probability of correctly reporting five of five optotypes, starts at 0% when the optotype size is small, and increases to 100% as the optotype sizes grow larger and larger. It is the intermediate multi-optotype psychometric functions—P(1/5) ( ) P(2/5), P(3/5), and P(4/5)—that exhibit interesting non-monotonic behavior. As predicted by the acuity model, those functions can exhibit peaks that are ordered and staggered, relative to increasing number of correctly recognized optotypes. Such probability function of correctly reporting 0 to 5 out of 5 optotypes are multi-optotype psychometric functions 2005. The chart-specific function, in this embodiment, E(s), is shown as 2006.

Figure 21:
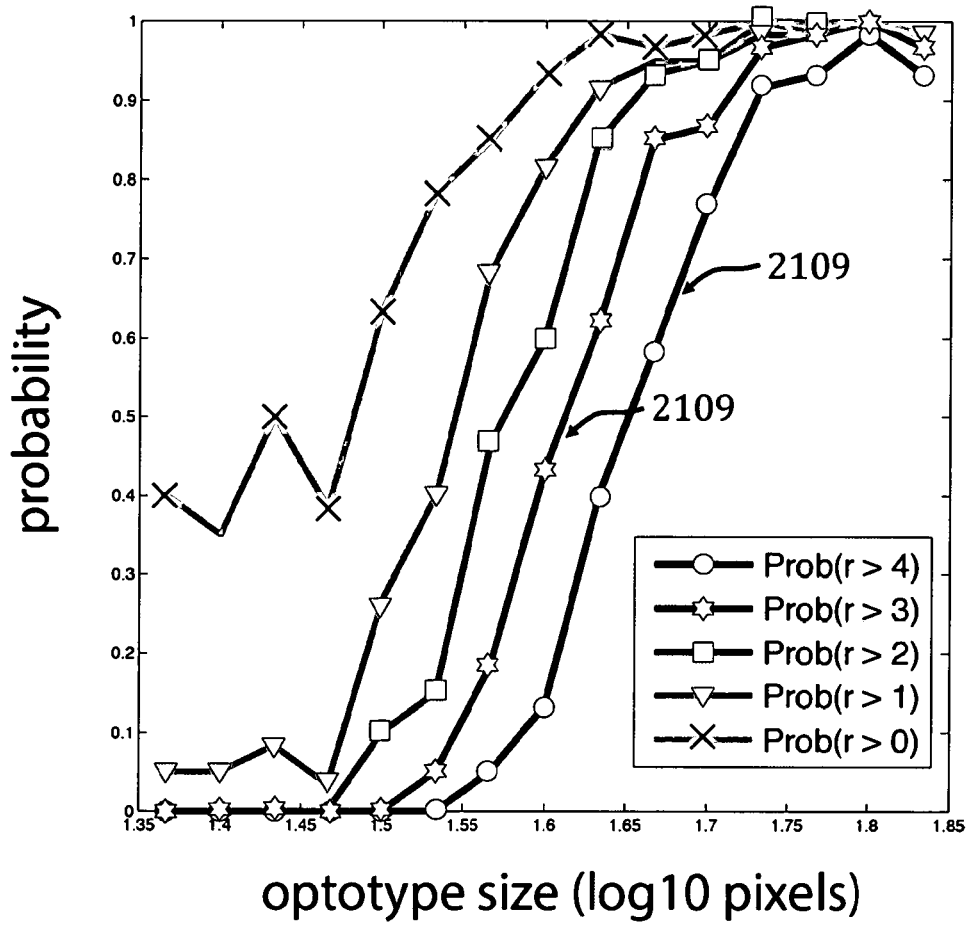
FIG. 21 shows a non-limiting example of validation of the combination algorithm.

To complement FIG. 20, and demonstrate the validity of the acuity model, FIG. 21 presents, cumulative probability functions that can be obtained from the multi-optotype psychometric functions 2005 in FIG. 20. The validity of the acuity model as a proper data-generating model can supported by the relative position and laminarity of these cumulative functions 2109. These data provide evidence that multiple-optotype psychometric functions 605, 805, 2005 may provide richer information about performance on visual acuity charts than single-optotype psychometric functions and/or acuity parameters.

In some embodiments, preliminary information about a patient's vision is used to calculate a personalized acuity chart design, which represents a high-rank dependent on the utility function. In some embodiments, the results of previous acuity testing, the results of other eye exams, diagnoses of co-morbid conditions, demographic information such as age or race, or information of the like may be collected as preliminary information of the test subject. Based on the preliminary information, the adaptive algorithm A may select the optimal chart design for that individual for the next trial or the entire test.

The advantage of such an adaptive acuity-testing method is that it is a comprehensive framework for evaluating and optimizing the information transmitted by visual acuity testing. Such method may calculate optimization (via the expectation of information gain) over m-ary responses, rather than solely binary responses.

In some embodiments, an initial ranking of the candidate acuity model parameters can be provided based on diagnoses of ocular disease.

In some embodiments, acuity testing begins with a broader, simpler acuity task. For example, the patient can be instructed to read only the first column of a full chart of optotypes, as shown in FIGS. 12A-12C. The last line for which the first optotype can be identified provides a reference point for starting the full testing procedure. Despite its usefulness (see below), this practice is conceptually different from taking an initial sample from a library of acuity charts.

For visual acuity testing, the presentation of a chart or sub-chart of optotypes is followed by a response that is collected by a technician or self-registered by the patient. In different response modes, a patient can (1) read down the first column; (2) read across the lines, until instructed to stop, or (3) read a single optotype presented to them. (During an actual test, the grayed optotypes appear identically to other optotypes; in this schematic figure, the different shade of gray signifies that they are not as prioritized for patient report as optotypes in solid black).

The acuity model herein can be adapted to analyze different acuity testing workflows: e.g., reading down the first column, reading the whole chart, or reading only single optotypes.

As disclosed herein, the initial sampling from the chart library can take several forms selected from but not limited to:
  a. non-random, full test—like the prior art, a single, standard ETDRS (or Snellen) chart is presented and the patient attempts to read all fourteen lines. In this case, the initial sample is simply the same chart that is typically presented to all patients;
  b. non-random, abbreviated test—as described above, a single, standard ETDRS chart is presented, but the patient reads only the first column; and
  c. random, full test—any chart from the library is sampled and presented. It need not use the fixed optotype sizes of the standard ETDRS or Snellen charts currently presented to all patients;

In some embodiments, the systems and methods disclosed herein may be used to analyze acuity metrics across these three different forms. To be more specific, such analysis may be applied to acuity data collected on current ETDRS and Snellen Charts and yield acuity metrics that are independent of chart design principles. Alternatively, a patient may read the first column of an initial chart, and then the test is continued with another chart or sub-chart based on adaptive acuity chart as disclosed herein. The analysis may be applied both to the initial chart and the subsequent test chart.

Response Scoring

In acuity testing, response scoring is a critical component that connects many other component processes—especially, those estimating acuity metrics deciding whether to continue or terminate the testing. Scoring of the response can be explicitly connected to the design features of the test. Decision to terminate the test can be related to the inability to see optotype. In the prior art, the primary distinction between chart-based method was line assignment vs letter-by-letter scoring. For single optotype computerized testing, the scoring is accuracy of identification: correct vs. incorrect. In some embodiments, a finer-grained scoring is used: the number of letters correctly reported on each line. This fine-grained row-based approach, the foundation of the current invention, differs from the current art of line assignment and letter counting.

The typical scoring of acuity testing may follow one or more heuristics. Nonlimiting examples of such heuristics include: assigning each line a pass/fail grade based on correctly reporting any letters on that line, assigning the last line to be read correctly with a criterion of 3 of 5 optotypes correct, or counting all the correctly reported letters, using letter-by-letter scoring.

In some embodiments, the algorithms disclosed herein focus on visual acuity metrics collected in a single test condition. It's often more important to measure and compare acuity metrics in two test conditions (left vs. right eye; low vs high luminance;). Therefore, it's also possible to consider extended algorithms that provide scoring and adaptive testing for acuity changes between multiple conditions.

In some embodiments, the scoring algorithm can be applied in a very simple "adaptive" way: for prospective analyses during testing with established charts, the scoring algorithm can drive the decision to continue testing until acuity estimates reach a certain precision level. To be specific, the same scoring algorithm can analyze the data collected when subjects are tested with the ETDRS with static, deterministic paper charts. These charts can be used for repeated testing until the Scoring Algorithm S returns parameter estimates of a given precision and/or reliability. Rather than consider this as an "adaptive" application, it may be more accurate to consider it a test termination application for quality control.

In some embodiments, the response format herein depends on the test design, e.g., whether the patient is presented with a full chart, a chart subsample with fewer lines, or a single-optotype. Patients may read:
  a full chart, row-by-row, until they can read no more than 2 letters;
  the first column;
  a single letter; or their combinations.
These three types of responses may give different results. The prior art gives all letters equal scoring. Technicians can register the response of patients via the: identity or identities of optotypes presented individually or in rows; correct or incorrect judgments of presented optotypes; or their combinations.

In the existing arts, these different responses are independently scored. Another method actually considers the full optotype confusion matrix, to evaluate the probability of reporting different optotypes based on their identity (e.g., 'O's are easier to read than 'K's). The systems and methods disclosed herein may handle the three types of responses within the same theoretical framework. Finer-grained line-by-line scoring may be generated, using relative response distributions. In some embodiments, the probabilistic behavior in an acuity task is considered. In some embodiments, the scoring may be based on the relative distribution of response outcomes as a function of optotype size. In some embodiments, the acuity model considers the: composite response; response combination; probabilistic description; consider and predict probability of composite responses; or a combination thereof.

In some embodiments, scoring may be done via a data table of candidate acuity functions; lookup table of predictive probabilities; empirical table of confusion matrices; or their combinations.

In the prior art, because the design principles that define optotype properties likewise constrain acuity metrics, many explicit testing strategies are design-dependent. This explains why these scoring methods result in different acuity estimates for ETDRS optotype sets with ten alternatives and HOTV/Lea optotype sets with four alternatives. As a result, acuity estimates obtained from different acuity tests are not directly comparable. Recent standards have appreciated an alternate approach to evaluating performance that attempts to correct for the guessing level of different optotypes. Those standards recognize the utility of using psychometric functions to describe optotype recognition performance. For example, the acuity threshold is defined as the 50% on the guessing-corrected psychometric function:

$Pc$=guessing rate+(1−guessingRate)*(sigmoidal function)

The use of the psychometric function recognizes that acuity performance is probabilistic, and defines the acuity threshold to be the 50% threshold on the guessing-corrected psychometric function. Because of different guessing rates for optotype sets of different sizes, the 50% threshold on the guessing-corrected psychometric function corresponds to different levels of objective performance. To summarize, the predominant methods in the existing art, for scoring acuity chart data to derive acuity metrics may include:
  a. Method of descending limits—line assignment
  b. Letter counting—each letter counts for 0.02 log MAR units, or
  c. 50% empirical or chart-specific thresholds estimated from the least-squares or maximum-likelihood fitting of guessing-corrected psychometric function The empirical, or equivalently herein, chart-specific thresholds on the chart-specific or empirical function can critically depend on design standards, such as the number of guessing alternatives for optotype identification. Therefore, the novel application of Signal Detection Theory to characterize psychometric functions in chart-invariant units of sensitivity may provide a potential solution to acuity metrics that do not depend on the explicit features of the acuity chart. The transformations between sensitivity psychometric functions and empirical chart-specific psychometric functions prescribed by signal detection theory can depend on the acuity chart features proposed in acuity chart standards.

Scoring Algorithm (Algorithm S)

In some embodiments, the systems and methods disclosed herein include a scoring algorithm, or algorithm S, a critical component of the framework for visual acuity testing. During an acuity test, subjects attempt to recognize optotypes of different sizes, presented on acuity charts or sub-charts. Applied in retrospective analysis, algorithm S may yield precise acuity metrics from previously collected acuity chart data. Although primarily scoring is based on the acuity data collected on full acuity charts, with multiple optotypes presented on multiple lines, the analysis can be simplified to score acuity testing with sub-charts: the presentation of a series of lines of optotypes, a single line of optotypes, or a single optotype.

In some embodiments, the algorithm S exhibits the flexibility to analyze acuity data as a function of the specific chart designs used for testing, or more generally, to analyze acuity data and generate acuity metrics independently of chart design. This analysis enables universal, chart-invariant acuity metrics or parameters that allow acuity results to be compared and coordinated across the many chart designs used in clinical practice.

FIG. 1 shows a flow chart of an exemplary embodiment of the scoring algorithm 40 disclosed herein. In this particular embodiment, algorithm S (scoring algorithm) 40 starts and at least one acuity chart design is determined 100. In this embodiment, the acuity chart design determination 100 is based on information provided by the user and/or information automatically generated by analysis of the visual acuity chart(s) or subchart(s) used for testing the subject. In the same embodiment, responses (i.e., acuity chart data) collected from test subject are summarized 400, for example, into acuity chart data tables. In parallel or in series with summarizing acuity chart responses 400, operation 300 can determine one or more sets of candidate acuity parameters (e.g., chart-specific or chart-invariant parameters) that may describe visual acuity of the test object. Operation 300 may occur in parallel, prior to, or subsequent to operation 200. In operation 200, an acuity model can be defined based on chart-specific or chart-invariant parameters (e.g., chart-specific acuity threshold, chart-specific acuity range, chart-invariant acuity threshold, etc). In some embodiments, sets of candidate acuity parameter values are selected as values for acuity parameters in the acuity model(s) determined in operation 200. Alternatively, or in combination, an acuity model as shown in FIGS. 6A-6C can be generated in operation 300 based on chart design parameters for predicting acuity chart data of the subject. In this case, defined acuity model(s) are applied to retrospectively predict acuity chart data using selected candidate parameters 500, the probability of aggregate response is calculated given an acuity model and its two acuity parameters as shown in Table 2. Afterwards, in the same embodiment, each acuity model with its candidate parameters are evaluated and ranked 600 based on a table summarizing the acuity chart data collected from test subject 400 as shown in Table 1. The estimation of acuity parameters can be based on the ranking of acuity model with its candidate parameters 700. In this case, the acuity model with highest rank is selected as the estimation of acuity parameters for the test object. The results of those statistical estimates are presented to the user and/or to the subject 800. Optionally, algorithm S finishes after the estimation is completed.

Referring to FIG. 3B, in a particular embodiment, determination of an acuity model for predicting acuity chart data or acuity test data 200 in FIG. 1 starts by determination of at least one single-optotype psychometric function 604, 804, using two chart-specific acuity parameters in operation 230, i.e., a set of candidate acuity parameters, such as an acuity threshold and an acuity range. In the same case, the family of multiple-optotype psychometric functions is calculated by serial multiplication of the single-optotype psychometric functions in operation 320. In the same embodiment, optionally, the chart-specific psychometric function is calculated using the weighted sum of the family of multiple-optotype psychometric functions in operation 420.

Referring to FIG. 3A, in a particular embodiment, determination of an acuity model for predicting acuity chart data or acuity test data 200 in FIG. 1 starts by determination of at least one single-optotype psychometric function that is chart-invariant 404 using two chart-invariant acuity parameters in operation 230, i.e., the sensitivity threshold, 401 and/or sensitivity range 403 in FIG. 4A, and cumulative Gaussian distribution function (cdf). In some embodiments, other chart-invariant acuity parameters such as sensitivity slope, sensitivity threshold change, etc can be used. In some embodiments, there can be two, three, four, five, six, seven, or even more single-optotype psychometric functions. In this embodiment, the single-optotype psychometric functions are converted from chart-invariant psychometric functions 404 to chart-specific psychometric functions 604, 804 in operation 330. In this embodiment, the single-optotype psychometric functions are converted from chart-invariant functions 404 to chart-specific psychometric functions in operation 330 by generating an intermediate chart-invariant function 504 as shown in FIG. 5. In the same embodiment, the family of multiple-optotype psychometric functions is calculated by serial multiplication of the single-optotype psychometric functions 320 that are chart-specific. In the same embodiments, optionally, the chart-specific psychometric function is calculated using the weighted sum of the family of multiple-optotype psychometric functions 420.

Referring to FIG. 5, in a particular embodiment, a chart-invariant single-optotype psychometric function, such as 404, may be presented using different coordinates from that of the chart-invariant single-optotype psychometric function in the conversion to the chart-specific single-optotype psychometric function 604. In this embodiment, FIG. 5 shows the probability of correctly reporting a single letter, as function of sensitivity, given the number of alternatives. There can be different functions 504 depending on the number of alternatives (e.g., 2AFC, 10AFC, etc). For example, a function corresponds to the probability of correctly responding "A" when the optotype set (the set of guessing alternatives) is "A" and "C" (2AFC). A lower probability of reporting "A" correctly out of the optotype set with 10 alternatives.

Adaptive Algorithm (Algorithm A)

In some instances, the systems and methods disclosed herein include an adaptive algorithm. The adaptive algorithm can be used to improve precision by focusing testing on the individual. To complement the application of algorithm S to retrospective analytics, adaptive algorithm A, for instances, can improve the prospective analytics of acuity chart data.

In some embodiments, algorithm A (adaptive algorithm) 20 improves the prospective analytics of acuity chart data by the selection of optimal acuity chart designs. In other words, algorithm A may select one or more acuity chart designs for future acuity test(s) of a specific subject based on collected acuity chart data of that specific subject.

Standard paper acuity charts can be deterministic. All subjects are tested with the same paper acuity chart are presented with the same optotypes, presented at the same sizes. Printing different forms of an acuity chart design, presenting the same optotype sizes but randomizing the optotypes, may prevent the simple learning or guessing of the chart by the subject. However, using the same restricted set of optotype sizes may reduce test flexibility and test precision.

Adaptive acuity testing using the adaptive algorithm herein is different: based on a subject's responses, in some embodiments, acuity testing is dynamically adjusted to focus on each subject. In recognition of the advantages of adaptive testing, relative to deterministic testing, the existing art has moved towards adaptive acuity testing with single optotypes. The adaptive testing approaches that dominate the existing art (up/down staircases; Dixon & Mood 1948; Zippy Estimation by Sequential Testing (ZEST); Parameter Estimation by Sequential Testing (PEST); and QUEST method are applicable only to single optotypes. As a prominent example, the full EDTRS acuity chart has been re-formulated as an electronic test, the e-ETDRS, which combines single optotype presentation, and an adaptive letter-by-letter scoring heuristic.

Figure 9:
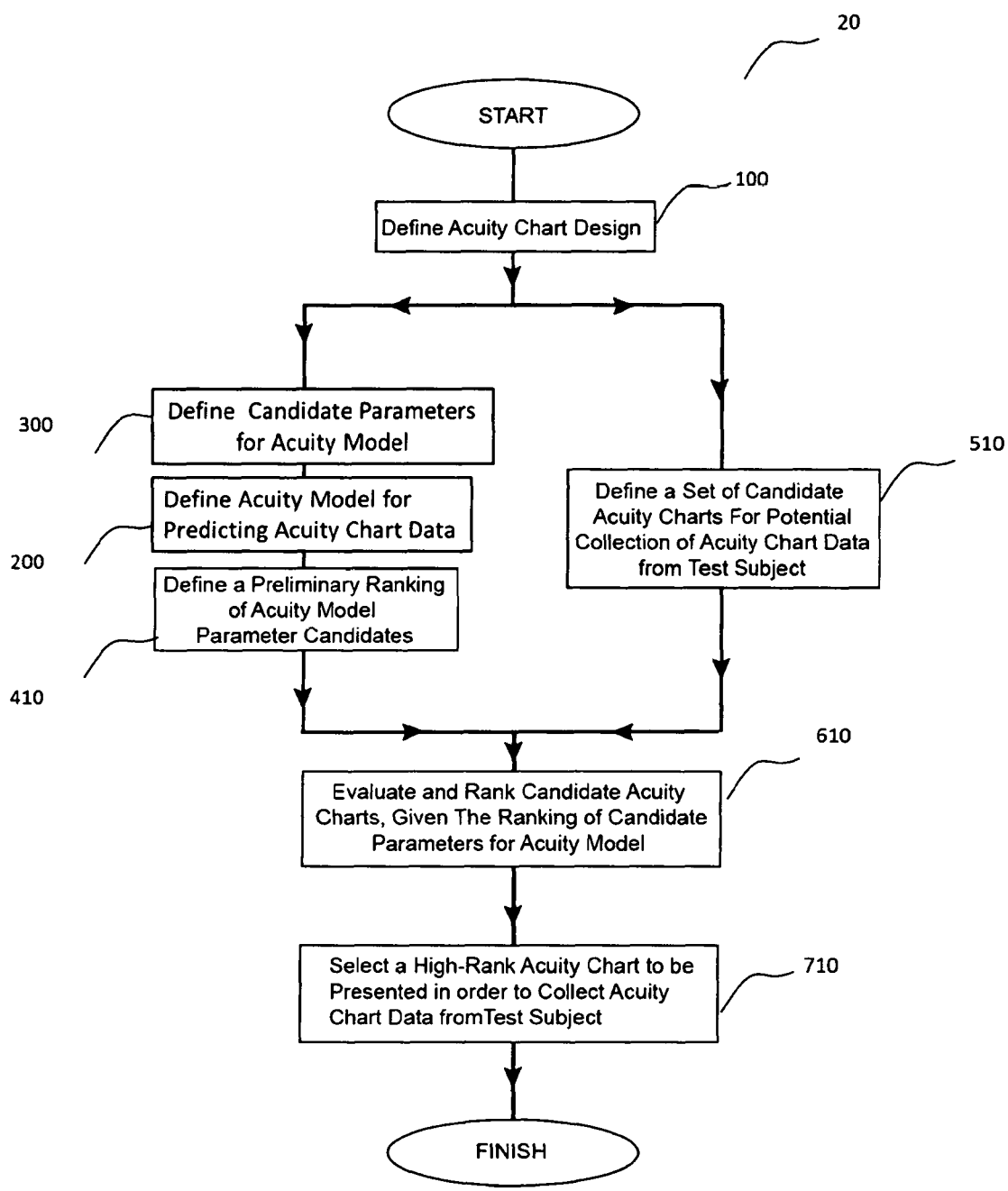
FIG. 9 shows a non-limiting example of a flow chart of the adaptive algorithm A disclosed herein.

In some embodiments, algorithm A provides a novel, more powerful, and more general approach to the adaptive testing of visual acuity. Algorithm A may optimize acuity testing with single optotype, a single line of optotypes, or multiple lines of optotypes. Algorithm A can powerful enough to optimize the full acuity chart that is to be presented to the subject. In some embodiments, the adaptive algorithm disclosed herein includes one or more of the following steps: 1) define an acuity chart design; 2) define an acuity model for predicting acuity chart data, 3) define a set of candidate acuity model parameters, and 4) a preliminary ranking of candidate acuity model parameters. The flow chart of an exemplary embodiment of algorithm A is shown in FIG. 9.

Unlike Algorithm S, which is applied to analyze previously collected acuity data, Algorithm A may be applied prospectively, to improve and personalize the collection of acuity data, based on previous information. To personalize an acuity chart to improve the quality of data collected from a specific subject, several steps are common with Algorithm S.

In some embodiments, in step 2), the acuity model used in algorithm S may be defined. Rather than applying the acuity model to predict previously collected data, algorithm A may include the acuity model to predict the optimal conditions to collect future acuity chart data. Algorithm A may provide a prospective analysis of which candidate acuity chart should be used to test the subject. In some embodiments, in step 3), the table of acuity model parameters as used in algorithm S may be defined. The table contains the candidate parameters with potential to describe the acuity chart data to be collected from the subject. The acuity model parameters can be chart-specific or chart-invariant. In algorithm S, the ranking of acuity model parameters can be done on the basis of likelihood values, which describe the prediction of acuity chart data as a function of acuity model parameters. In some embodiments, in step 4), the preliminary ranking of acuity model parameters can be uniform or defined on an arbitrary scale. In some embodiments, the ranked values should be normalized to 1. This effectively makes the list of ranked values a probability distribution. Before testing, all candidate parameters can have uniform probability. Given those candidate parameters, a probability distribution that described the probability of that parameter combination describing the subject may be constructed. To begin the Bayesian adaptive inference, the ranking of candidate parameters can be translated to probability distribution. The preliminary ranking of candidate acuity parameters can be uniform. Alternatively, preliminary prior information can be used to seed the knowledge concerning the subject's vision. The prior information can come from but not limited to:

a. demographics, such as age;
b. co-morbid disease such as cataract, AMD, or other conditions known to affect the visual system;
c. a different vision test;
d. a reduced, screening mode of the current test. For example, rather than read the whole chart, subjects can read down the first column; or their combinations.

Given translation of ranking of candidate parameters to prior probability, the test can begin. Before the first test trial, there is no acuity data to consider and score. Therefore, the first application may consider the history of the data collected. In this case, uniform ranking leads to flat prior.

In some embodiments, single optotype psychometric functions are generated using acuity chart data, then based on the acuity chart data predicted by the generated single optotype psychometric functions, and given the goodness of fit for that data, estimates of the acuity threshold and range can be obtained of the subject.

Referring to FIG. 9, in a particular embodiment, algorithm A (adaptive algorithm) 20 optionally starts with determining acuity chart design parameters 100. After the chart design has been determined, optionally, candidate parameters (e.g., one or more acuity thresholds, acuity slopes, and/or acuity ranges) are selected for defining acuity models 200, 300 as described similarly in FIG. 1 and FIG. 3A and/or FIG. 3B. An acuity model as shown in Table 2 can be defined based on preliminary information of test subject for predicting acuity chart data. In this case, an initial ranking of acuity models is generated 410 based on the acuity model in operation 200, parameters in operation 300, and/or the response collected in operation 400 in FIG. 1. A set of candidate acuity charts to be presented to the subject is determined 510 at least in part by the acuity chart design features. Alternatively or in combination, a set of candidate acuity charts to be presented to the subject is determined 510 by acuity chart data or acuity test data of the subject that has been collected from previous test. In some embodiments, a set of candidate acuity charts to be presented to the subject is determined by other information of the test object, such as demographic information, previous acuity parameter estimations, previous acuity test results, etc. Optionally, in this embodiment, each candidate acuity chart of 510 is evaluated and ranked 610 based on the preliminary ranking of acuity model and acuity parameters in 410. In the same case, an acuity chart of one of the highest rank (i.e., top 1, top 2, and/or or top 3) is selected to be presented to the test subject 710 and the adaptive algorithm finishes. Optionally, the acuity chart can be chosen randomly from the top decile or quartile of ranked acuity charts.

For example, in addition to defining an acuity chart design, and defining an acuity model based on that design, it is necessary to define a set of candidate acuity model parameters for describing the acuity chart data to be collected from the patient. As shown in FIG. 9, following several steps common to Algorithm S—the definition of an acuity chart design 100 and acuity model 200, the definition of candidate acuity model parameters 300, and steps that are different to those in algorithm S 410, 510, and 610—the analysis of candidate acuity charts yields the optimal acuity chart design that can be used to test the subject's vision 710. For example, the optimal acuity charts may focus on the optotype sizes that may be close to the subject's acuity threshold, or within the acuity range of the subject.

Combination Algorithm

Figure 16:
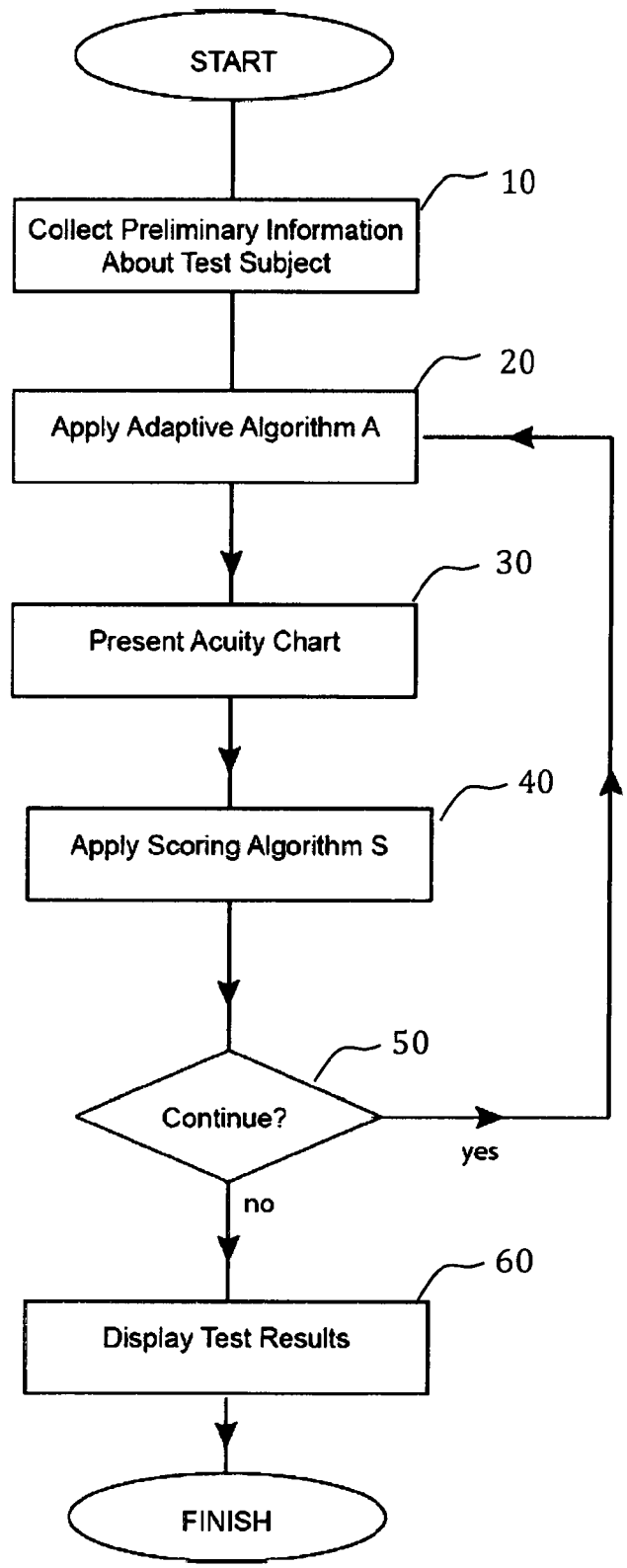
FIG. 16 shows a non-limiting example of a flow chart of the combination algorithm using algorithm A and S as disclosed herein.
Figure 17:
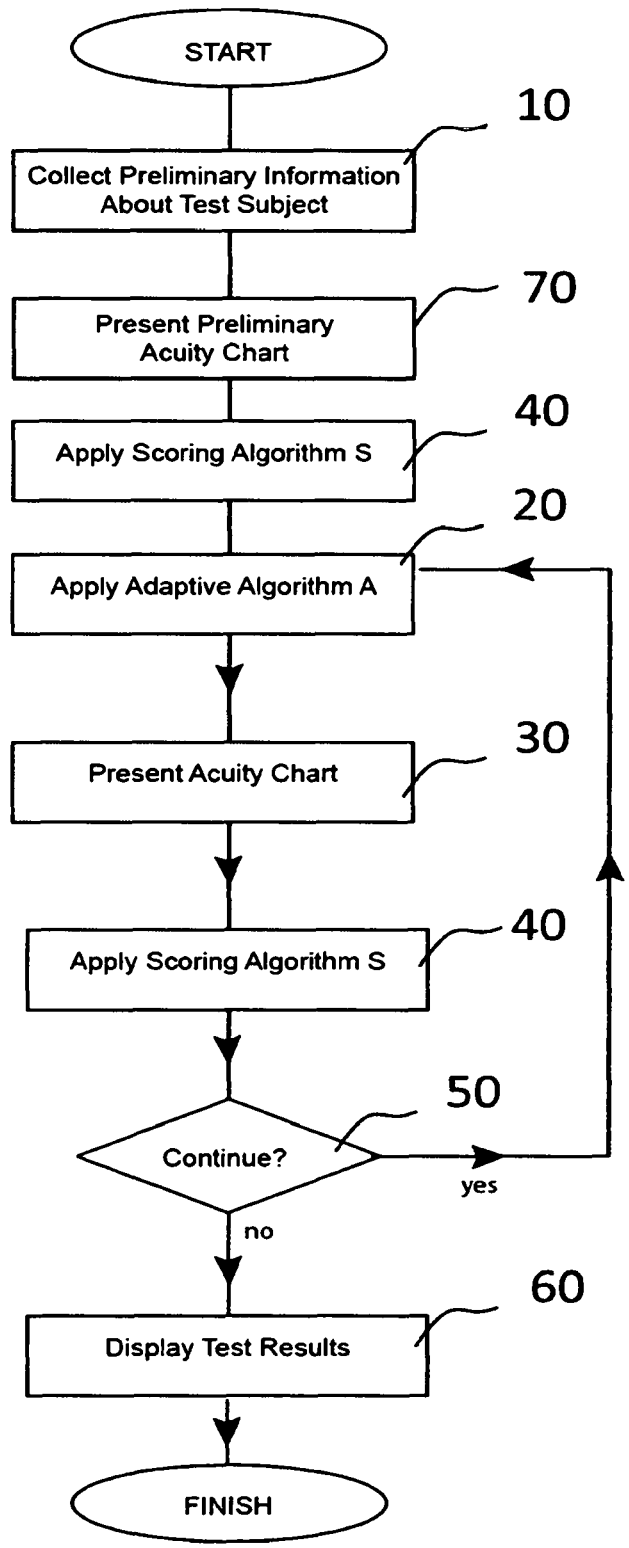
FIG. 17 shows another non-limiting example of a flow chart of the combination algorithm using algorithm A and S as disclosed herein.

The systems and methods disclosed herein may include a combination algorithm. The exemplary embodiments of the combination algorithm disclosed herein are shown in FIGS. 16-17. The systems and methods disclosed herein resolve the complication of visual acuity metrics by adding more psychometric functions by applying a combination of Signal Detection Theory and Probability Theory. In some embodiments, the analysis herein considers how implicit chart-invariant psychometric functions defined by two sensitivity parameters, for example, sensitivity threshold and sensitivity slope or sensitivity threshold and sensitivity range, may generate the full family of explicit psychometric functions that are observed in visual acuity testing.

Referring to FIG. 16, in a particular embodiment, an acuity test optionally starts with collecting preliminary information about the subject to be tested 10. In the same embodiment, algorithm A is applied 20, and an acuity chart is presented to the test subject 30, algorithm S is applied 40 to generate a score of acuity testing. If the result from algorithm S satisfies the termination condition, (e.g., if the model parameters are above a determined threshold probability or if the dispersion of the Bayesian posterior is below a determined level of variability), the acuity test does not continue 50 and the test results (e.g., values of estimated visual acuity parameters of the subject) are displayed 60. Optionally, if the result from algorithm S does not meet the termination criteria, the acuity test continues 50 by repeating one or more previously performed steps.

Referring to FIG. 17, in a particular embodiment, an acuity test optionally starts with collecting preliminary information about the subject to be tested 10. Afterwards, preliminary acuity chart selected based on the preliminary information may be presented to the subject 70 and scoring algorithm S can be applied 40 to generate a score for the subject's visional acuity. In the same embodiment, algorithm A is then applied 20 on the score and/or preliminary information of the user, and an acuity chart adaptively generated by the algorithm A is presented to the test subject 30. After responses have been collected from the subject, algorithm S is applied 40 to generate a score of acuity testing of the subject. If the results from algorithm S satisfy the termination condition, the acuity test does not continue 50 and the test results are displayed 60. Optionally, if the result from algorithm S does not meet the termination criteria, the acuity test continues 50 by repeating one or more previously performed steps.

Signal detection theory (SDT) was established to describe the wartime performance of radar operators, and distinguish between the perception-level factors that made operators sensitive for target detection and the decision-level factors that made them liberal or conservative in responding to targets (Green & Swets, 1961; McMillan & Creelman, 2004, which are incorporated herein entirely by reference). The SDT framework provides a richer quantification of detection behavior beyond "correct" and "incorrect". The SDT analysis considers how perceptual sensitivity (d') parameters and decision-level parameters contribute to predict the observed probabilities of "hits', 'misses", "false alarms", and "correct rejections". The distinction between sensitivity and decision factors, and their quantification, has been critical to the development of modern psychophysics. It provides a framework to identify the contributions of factors that are independent of the design of the psychophysical task, versus factors of response bias and decision criteria that are specific to the task design and the subject. Lesmes et al (2015, which is entirely incorporated herein by reference) combined Bayesian adaptive algorithms and signal detection theory analysis to develop adaptive methods that provide threshold estimates that are independent of psychophysical task, e.g., forced choice, simple detection, cued detection and rated detection. In the current invention, adaptive algorithms are elaborated to consider the complicated design of acuity charts, and provide measures of visual acuity that are design-invariant, independent of task factors and design-principles that are specific to each acuity chart.

When combined with adaptive testing algorithms that are design-dependent—tuned to optimize for the design of specific charts—the library of acuity charts can be optimally sampled to accelerate and improve testing and analysis of acuity and its changes.

Despite some of the complexity of the predictive model or acuity model disclosed herein, it can be simplified and presented to the patient and doctor as a display of the test results.

Validation of Combination Algorithm.

Some exemplary aggregate simulation results of the combination algorithm are shown in FIG. 18. The convergence of adaptive acuity testing is reflected in Bayesian posterior estimates obtained from a large number of simulated testing runs. The broadest posterior reflects the earliest acuity threshold estimates obtained from the patient's reading of the first column of the full 14-line ETDRS chart shown in slide 0. On the next chart presented on slide 1, the patient is presented with a smaller five-line subchart that adheres to ETDRS principles, but also represents a subchart specifically optimized to the patient. The Bayesian posteriors that result after testing with slide 1 reflect the Bayesian update of the parameters of the visual acuity model. Reduction in the dispersion of the Bayesian posterior reflects the success of the information-gain criterion used for adaptive testing. Convergence of acuity estimates continues with the information gained from the presentation of optimized slide 2. The inset presents the rapid reduction in test variability with increasing number of test slides.

FIG. 19 shows experimental results for adaptive chart-based acuity testing. One person with normal vision is optionally tested with standard-constrained adaptive testing algorithm that presented 5 chart slides in sequence, with each chart comprising 5 lines, with each line on the chart comprising 5 letters sampled from the Sloan set without replacement. Four test runs are completed, and the variability of test results are calculated over multiple runs. Successful convergence of this adaptive testing is reflected in the reduced variability of acuity threshold estimates with increasing number of test slides.

Tests and Responses

In some embodiments, a visual acuity test herein contains at least one test run or at least one test slide. In each test run or test slide, the subject is presented with a chart or a subchart of optotypes, proper response of the subject to testing question is required in order to properly record the response, evaluate the response, score the response, estimate acuity parameters, proceed or exit the current test.

In some embodiments, test responses are recorded individually for each test run within a single test.

In some embodiments, the optotypes are sampled repetitively from a library of optotypes. In some embodiments, the optotypes are sampled non-repetitively from a library of optotypes.

In some embodiments, the at least one optotype in a visual chart or subchart is generated using random sampling from an optotype library. In some embodiments, the at least one optotype in a visual chart or subchart is generated using adaptive sampling from an optotype library.

In some embodiments, the expectation of information gain is calculated for all the potential charts or subcharts to be presented on the next trial. In some embodiments, the expected entropy is calculated for all the potential charts or subcharts to be presented on the next trial. In some embodiments, the chart, subchart, or slide with minimum expected entropy is present to the subject.

Terminations

In some embodiments, the test is terminated after meeting at least one of the termination criteria. In some embodiments, the visual acuity test terminates after testing a predetermined number of test charts, subcharts, or slides. In some embodiments, the visual acuity test terminates after meeting a preset precision level.

In some embodiments, for the sake of a short testing time, testing can be terminated after only one chart. Alternatively, for the sake of precision, testing can continue with refined optimal selection, as more and more information is collected, testing can be more and more focused to the individual. Termination rules for reading the ETDRS charts are heuristic: patients are encouraged to advance until they can no longer read 3 of 5 optotypes per line.

In some embodiments, rather than terminate the test, the test can continue adapting its focus to the individual. An optimization algorithm can improve the test by focusing testing to the most informative regions of the acuity chart. If the test is not terminated after reading the first chart (in the first trial), then Algorithm A may be applied to present another acuity chart. If the test is to be terminated, then the system or method may display the test results to the subject.

Display of Test Results

With reference to FIG. 1, the results including model parameters can be displayed to the user and/or subject 800. In some embodiments, the results of chart-based acuity testing is visualized in a manner so that the tested subject, the doctor, and/or caregiver intuitively understand the results. Referring to FIGS. 22A-22D, in some embodiments, the Bayesian posterior probability function of acuity parameters, i.e., the acuity threshold and/or range, generated over different acuity model parameters is overlaid on the ETDRS acuity chart as a heat maps (FIGS. 22A-22B). In some embodiments, the heat map of acuity parameters signifies the mean estimates of acuity threshold parameters with darkest grey, and the shade of grey gradually decreases as the optotype size differs gradually from the mean optotype size. In some embodiments, the gradient of color changes in the heat map reflects the slop of acuity sensitivity. In some embodiments, the progression of disease or remediation by therapy, is represented by multiple heat maps presented on the same chart. In a particular embodiment as in FIG. 22A, the results reflect less confidence in acuity threshold parameters, relative to the results presented as in FIG. 22B. This may provide a useful presentation of acuity results that correspond to sizes between those presented on the ETDRS standard. In another particular embodiment, the Bayesian posterior probability is represented by a graphical box plot (FIG. 22C), which indicates the mean, interquartile range, and finally the 95% confidence interval of the acuity threshold estimate. In another embodiment as in FIG. 22D, the progression of vision loss is indicated by acuity metrics taken at different assessment times. "time 1" represents tested visual acuity threshold at the first time point, and "time 2" represents tested visual acuity threshold at the second time point.

Referring to FIG. 23, in a particular embodiment, the predictive performance is overlaid on the visual acuity chart for display. In this embodiment, the probability of correctly identifying less than 3 optotypes out of a total of five optotypes of each line is shown in solid black right above each line of the acuity chart. In this embodiment, the probability of correctly identifying 3 optotypes out of a total of five optotypes of each line is shown in dark gray. In this embodiment, the probability of correctly identifying more than 3 optotypes out of a total of five optotypes of each line is shown in light gray, and the probability of correctly identifying exactly 3 optotypes out of a total of five optotypes of each line is shown in medium gray. The probabilities are quantified using the length of each grey bar divided by the length of all three bars under each row of optotypes.

In some embodiments, visual acuity parameter estimates may be presented on the acuity chart. In addition, the results of several tests over time can be presented which may conveniently show progression of vision over time.

For patient engagement and education, visualization of test results is important. For progressive vision loss, for example, the extent and rate of vision loss are important factors. Particularly for diabetes-related vision loss, for which compliance and control of glycemic levels directly affect the vision, visualization of test results may include a wealth of visual acuity related statistics. These statistics may include one or more of: a posterior probability distribution, parameter boxplots, mean plus confidence, visual sensitivity parameters, visual threshold parameters/mean plus confidence, empirical or psychometric thresholds and sensitivity thresholds, means/confidence intervals, acuity thresholds and acuity ranges, acuity thresholds and acuity slopes, degrees of change, overlap presents the probability of changes, overlap of acuity probability distributions.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 24:
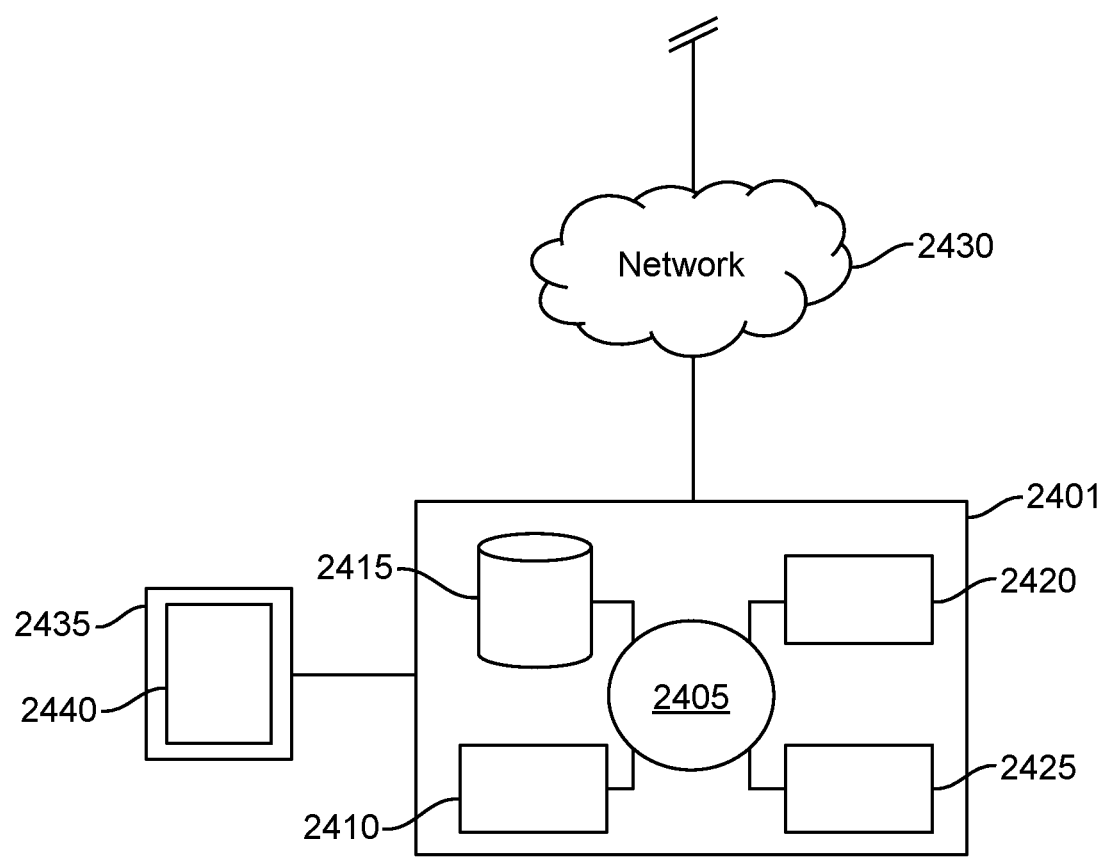
FIG. 24 shows a non-limiting example of the digital processing device as disclosed herein.

Referring to FIG. 24, in a particular embodiment, an exemplary digital processing device 2401 is programmed or otherwise configured to estimate visual acuity of a subject. The device 2401 can regulate various aspects of the algorithms and the method steps of the present disclosure. In this embodiment, the digital processing device 2401 includes a central processing unit (CPU, also "processor" and "computer processor" herein) 2405, which can be a single core or multi core processor, or a plurality of processors for parallel processing. The digital processing device 2401 also includes memory or memory location 2410 (e.g., random-access memory, read-only memory, flash memory), electronic storage unit 2415 (e.g., hard disk), communication interface 2420 (e.g., network adapter) for communicating with one or more other systems, and peripheral devices 2425, such as cache, other memory, data storage and/or electronic display adapters. The memory 2410, storage unit 2415, interface 2420 and peripheral devices 2425 are in communication with the CPU 2405 through a communication bus (solid lines), such as a motherboard. The storage unit 2415 can be a data storage unit (or data repository) for storing data. The digital processing device 2401 can be operatively coupled to a computer network ("network") 2430 with the aid of the communication interface 2420. The network 2430 can be the Internet, an internet and/or extranet, or an intranet and/or extranet that is in communication with the Internet. The network 2430 in some cases is a telecommunication and/or data network. The network 2430 can include one or more computer servers, which can enable distributed computing, such as cloud computing. The network 2430, in some cases with the aid of the device 2401, can implement a peer-to-peer network, which may enable devices coupled to the device 2401 to behave as a client or a server.

Continuing to refer to FIG. 24, the CPU 2405 can execute a sequence of machine-readable instructions, which can be embodied in a program or software. The instructions may be stored in a memory location, such as the memory 2410. The instructions can be directed to the CPU 2405, which can subsequently program or otherwise configure the CPU 2405 to implement methods of the present disclosure. Examples of operations performed by the CPU 2405 can include fetch, decode, execute, and write back. The CPU 2405 can be part of a circuit, such as an integrated circuit. One or more other components of the device 2401 can be included in the circuit. In some embodiments, the circuit is an application specific integrated circuit (ASIC) or a field programmable gate array (FPGA).

Continuing to refer to FIG. 24, the storage unit 2415 can store files, such as drivers, libraries and saved programs. The storage unit 2415 can store user data, e.g., user preferences and user programs. The digital processing device 101 in some cases can include one or more additional data storage units that are external, such as located on a remote server that is in communication through an intranet or the Internet.

Continuing to refer to FIG. 24, the digital processing device 2401 can communicate with one or more remote computer systems through the network 2430. For instance, the device 2401 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 2401, such as, for example, on the memory 2410 or electronic storage unit 2415. The machine executable or machine readable code can be provided in the form of software. During use, the code can be executed by the processor 2405. In some embodiments, the code can be retrieved from the storage unit 2415 and stored on the memory 2410 for ready access by the processor 105. In some situations, the electronic storage unit 2415 can be precluded, and machine-executable instructions are stored on memory 2410.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some embodiments, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java™, and Unity®.

Figure 25:
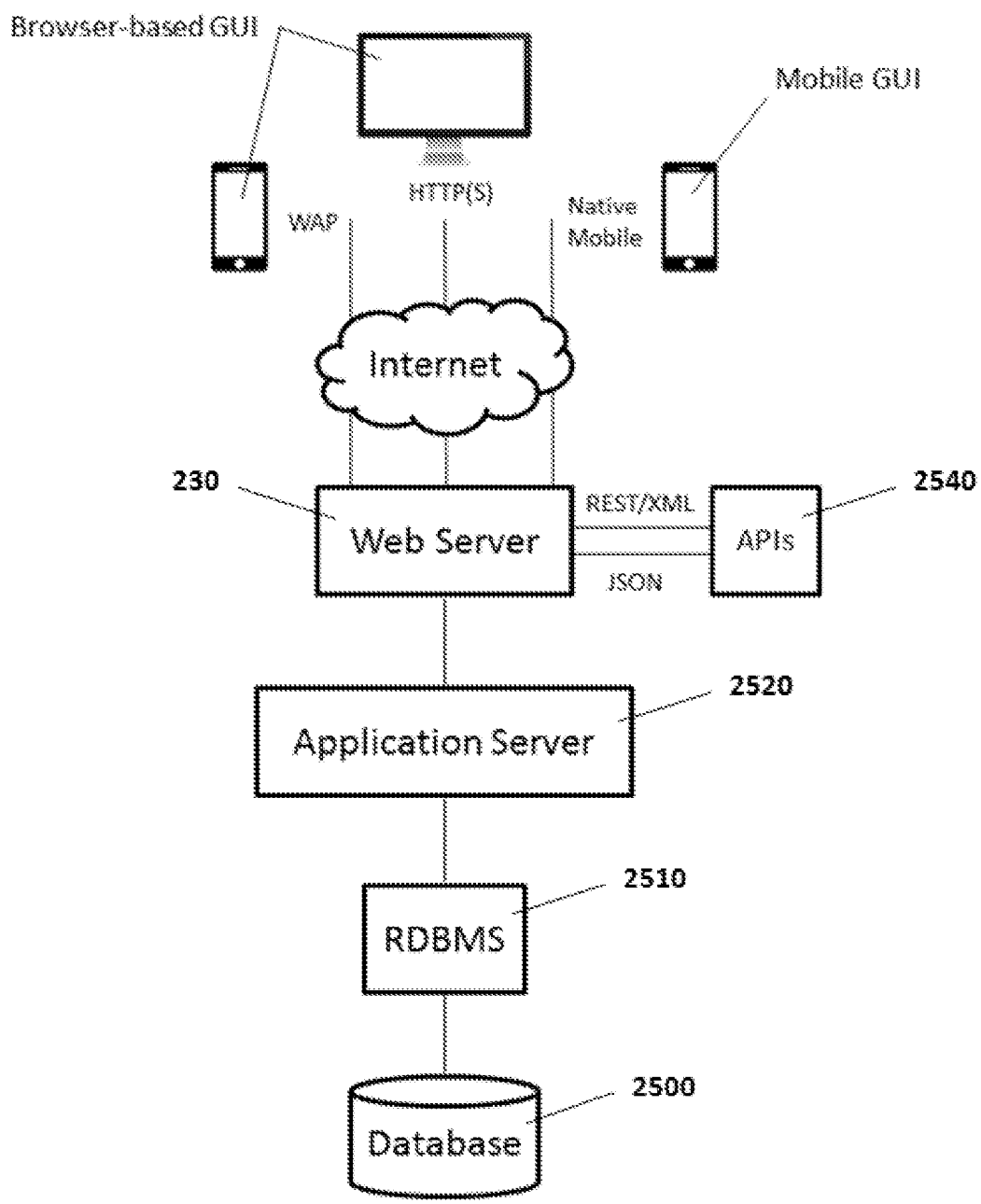
FIG. 25 shows a non-limiting schematic diagram of a web/mobile application provision system; in this case, a system providing browser-based and/or native mobile user interfaces.

Referring to FIG. 25, in a particular embodiment, an application provision system comprises one or more databases 2500 accessed by a relational database management system (RDBMS) 2510. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 2520 (such as Java servers, .NET servers, PHP servers, and the like) and one or more web servers 2530 (such as Apache, IIS, GWS and the like). The web server(s) optionally expose one or more web services via app application programming interfaces (APIs) 2540. Via a network, such as the Internet, the system provides browser-based and/or mobile native user interfaces.

Figure 26:
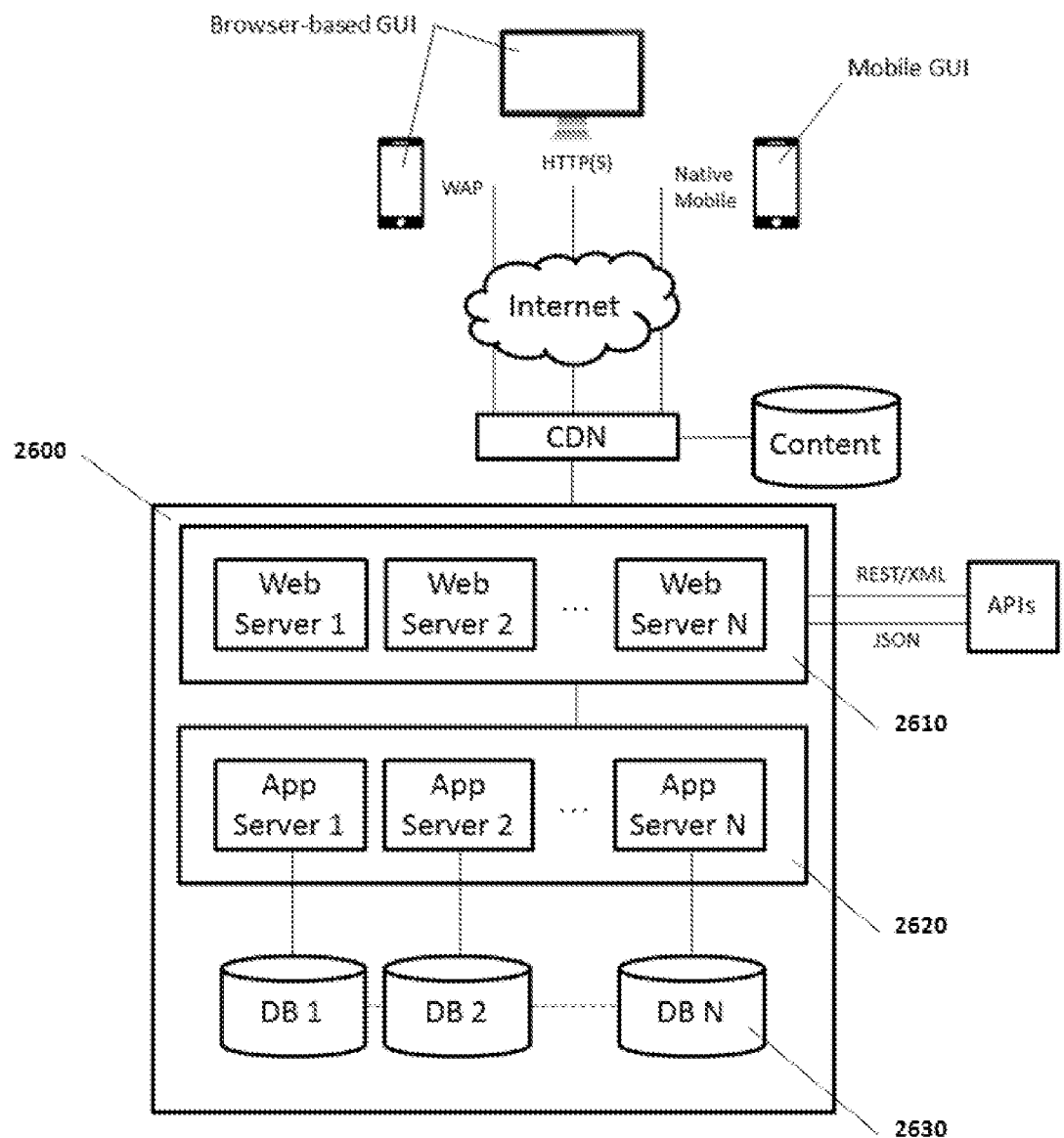
FIG. 26 shows a non-limiting schematic diagram of a cloud-based web/mobile application provision system; in this case, a system comprising an elastically load balanced, auto-scaling web server and application server resources as well synchronously replicated databases.

Referring to FIG. 26, in a particular embodiment, an application provision system alternatively has a distributed, cloud-based architecture 2600 and comprises elastically load balanced, auto-scaling web server resources 2610 and application server resources 2620 as well synchronously replicated databases 2630.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of acuity chart, acuity subchart, preliminary information of a subject, chart data of a subject, input and/or output of algorithms herein etc. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

EXAMPLES

The following illustrative examples are representative of embodiments of the software applications, systems, and methods described herein and are not meant to be limiting.

Example 1

A computer-based medical system as disclosed herein is used for tests and analyses of visual acuity of a diabetic subject by presenting to the subject with three out of the ten Sloan letters at a time on a digital screen. The prior information used to initiate the testing is a population-based study of visual acuity. With those population estimates, the device applies algorithm A to present the subject with high-rank single-line sub-charts on each test slide. After applying algorithm S to evaluate the acuity chart data collected on each slide, with respect to an acuity model that is predicting the respective probabilities of reporting 0, 1, 2, or 3 letters correctly on each slide, the next slide is selected based on a re-iterative application of algorithm A. When the patient returns for the next testing, the test starts with information from the population-based study of visual acuity, or instead considers the data from the previous testing session.

Example 2

A computer-based medical device that applies the combination Algorithm to test visual acuity with personalized versions of the full Snellen or ETDRS acuity charts. Current testing with paper acuity charts is based on one reading, or "run", through the full acuity chart, as the subject reads from the top of the chart to the bottom. In practice, when testing the visual acuity of two eyes, it is common to ask subjects to read through a single full acuity chart: first with one eye and then with the other. This confound, which prevents the independent testing of the two eyes, would be addressed and corrected by the personalization of different acuity charts to test each eye.

Like the application described above, general or specific clinical information can be used to initiate Algorithm A. Based on that information, Algorithm A is applied to select a personalized Snellen or ETDRS design. Following scoring with Algorithm S, the testing can terminate after the presentation of a single full chart, or testing can continue with the generation of a second full chart, based on the reiterative application of Algorithm A.

By presenting full visual acuity charts that follow the design principles of the ETDRS or Snellen charts, this adaptive acuity testing conforms to current standards and established practices, while allowing novel algorithms that can personalize acuity testing and allow high-resolution sampling of optotype size, and thereby improve its precision.

Example 3

A web-based software service that allows retrospective analysis of acuity chart data. Customers uses this web interface to apply algorithm S to analyze visual acuity data they have previously collected using established visual chart designs. Current analyses of these data provide qualitative results with limited precision. This application of the scoring algorithm provides the richer information needed for detecting changes in visual acuity.

This is accomplished by detecting changes in sensitivity parameters that are independent of the specifics of the chart design. In the case of testing changes in contrast sensitivity, (Hou et al 2016, which are incorporated herein entirely by reference) proposed a novel Bayesian signal detection analysis that computes an area under the ROC to characterize the change between two experimental conditions, using the Bayesian posterior distributions estimated in independent experimental conditions. They calculated Bayesian posterior distributions for the one-dimensional summary metric provided by the area under the log contrast sensitivity function (AULCSF).

A user evaluates changes in acuity using an area under the ROC analysis to calculate the probability that the acuity threshold in one test is greater than the acuity threshold in a second test. In some applications, the acuity model results to be evaluated were obtained in tests of the different eyes, in tests of pre-treatment vs post-treatment, or in tests of acuity at low luminance and high luminance. Optionally, the signal detection analysis can be extended to two dimensions to evaluate visual changes in the two parameters of the chart-invariant psychometric function. This two-dimensional signal detection will detect changes in acuity threshold, or acuity range, or both. In addition, the Scoring Algorithm can be applied to score data from other tasks that include letter identification as a function of other stimulus parameters, such as contrast sensitivity testing, and reading functions. Rather than defining the acuity chart design as a function of optotype size, these visual and cognitive tasks measure performance as a combination of other design parameters that can be quantified and estimated.

Example 4

In a mobile-based application, Algorithm S is applied to analyze visual acuity data, during its active collection in clinic with established chart designs. To coordinate the definition of the acuity chart design needed for scoring with the chart design in clinical use, the application presents the user with a library of acuity chart designs. When presented with the library, the user indicates which chart is being used to collect data. Given the limited number of acuity charts currently marketed, and the tendency for clinicians use the same paper charts for years, it is feasible to build a small- to medium-sized library of acuity chart designs in active circulation.

After the acuity chart design is defined for scoring, the app and mobile device serve as a response remote, to mark the optotypes that are reported correctly or incorrectly. In a different implementation, given the proper acuity chart design by the user, the subject can use an interface that allows for unsupervised testing.

A population database is built for recording acuity chart data. As the acuity chart data is collected and scored, the analyses can be uploaded to a server. The resulting database provide a foundation for machine learning and big data analytics that improves the acuity chart model and improve the preliminary information that is used to initiate the Combination Algorithm in Examples 3 and 4. In these two examples, the scoring and analyses of retrospective data, and the prospective collection of novel data, greatly improve the computational framework.

Example 5

A software service aggregates and analyzes the retrospective and prospective analyses of acuity chart data, which are generated by the hardware, software, and services defined in Examples 1-4. The analyses of these big data using Algorithm S provides a foundation to better inform the preliminary information that is used to initiate Algorithm A. For longitudinal acuity data collected over time, the software service calculates the change indices for acuity. For example, in addition to calculating the running indices that estimate the probability of acuity reduction between sessions, a global change index is calculated to estimate the probability of acuity change relative to the initial baseline.

Example 6

A computer-based medical device that implements algorithms S and A, in a combination with an acuity model that directly measures the inter-ocular difference in acuity. The eyes are stimulated independently, as in a phoropter, stereoscope, or virtual-reality headset. The acuity model is implemented optionally with a total of three or four acuity model parameters. For example, the acuity model comprises the acuity threshold and acuity range for the left eye. In addition, the model comprises two difference parameters, which respectively define the acuity threshold difference in between the left and right eye, and Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," and "approximately" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, or +/−20% depending on the embodiment. As a non-limiting example, about 100 meters represents a range of 95 meters to 105 meters, 90 meters to 110 meters, or 85 meters to 115 meters depending on the embodiments.

All publications, patents, and patent applications mentioned in this specification are herein incorporated by reference to the same extent as if each individual publication, patent, or patent application was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A computer-implemented system for generating an acuity model for scoring visual acuity of a subject, the system comprising:
   a digital processing device comprising an operating system configured to perform executable instructions and a memory; and
   a computer program including instructions executable by the digital processing device to create a scoring application comprising a software module:
   a) obtaining one or more acuity chart design parameters;
   b) collecting acuity test data of the subject;
   c) selecting a first set of chart-specific acuity parameter from one or more sets of candidate acuity parameters;
   d) generating an acuity model comprising:
      i. generating a single-optotype psychometric function, the single-optotype psychometric function comprising the first set of chart-specific acuity parameters;
      ii. calculating a family of multiple-optotype psychometric functions using the single-optotype psychometric function; and
      iii. generating a chart-specific psychometric function using the family of multiple-optotype psychometric functions, the chart-specific psychometric function comprising a second set of chart-specific acuity parameters,
   wherein the acuity model is configurable to estimate possibility of obtaining the acuity test data of the subject based on the one or more acuity chart design parameters.

2. The system of claim 1 comprising, subsequent to (c) and prior to (i), generating a sensitivity-based psychometric function comprising a first set of chart-invariant sensitivity parameters, and wherein the first set of chart-invariant sensitivity parameters comprises a sensitivity threshold and a sensitivity range, and wherein the first set of chart-invariant sensitivity parameters are generated based on the first set of chart-specific acuity parameters.

3. The system of claim 2, wherein the sensitivity-based psychometric function is independent of the one or more acuity chart design parameters, wherein the sensitivity-based psychometric function is generated based on signal detection theory or the one or more acuity chart design parameters and one or more additional parameters of the subject, the one or more additional parameters of the subject being chart-invariant, and wherein the sensitivity-based psychometric function is configured to describe visual acuity performance of the subject as a d' function of one or more optotype sizes and independent of the one or more chart design parameters.

4. The system of claim 2 comprising: translating the sensitivity-based psychometric function to the single-optotype psychometric function, prior to (i).

5. The system of claim 1, wherein the first set of chart-specific acuity parameters comprises an acuity threshold and an acuity range, wherein the single-optotype psychometric function is chart-specific, wherein the second set of chart-specific acuity parameters comprises an acuity threshold and an acuity range.

6. The system of claim 1, wherein the first set or the second set of chart-specific acuity parameters comprises an acuity threshold, an acuity range, an acuity slope, a change in the acuity threshold between two test conditions, the change in the acuity range between two test conditions, the change in the acuity slope between two test conditions, or a combination thereof, wherein the first set or the second set of chart-specific acuity parameters comprises at least one posterior probability density function for a parameter thereof, and wherein the first set or the second set of chart-specific acuity parameters comprises posterior probability density functions for an acuity threshold from at least two different test conditions.

7. The system of claim 1, wherein the one or more acuity chart design parameters comprises: a total number of optotypes, a number of optotypes per line, a method of optotype sampling, an optotype size, a number of lines, and a response of the subject, or a combination thereof.

8. The system of claim 1, wherein one or more functions in the family of multiple-optotype psychometric functions is based on a number of optotypes per line in an acuity chart or subchart.

9. A computer system for generating an acuity model for scoring visual acuity of a subject, the system comprising:
- a digital processing device comprising an operating system configured to perform executable instructions and a memory; and
- a computer program including instructions executable by the digital processing device to create a scoring application comprising a software module:
  - a) obtaining one or more acuity chart design parameters;
  - b) collecting acuity test data of the subject;
  - c) generating one or more sets of candidate acuity parameters based on the one or more acuity chart design parameters, the acuity test data of the subject, or both;
  - d) generating an acuity model comprising generating one or more chart-specific psychometric functions, each chart-specific psychometric function comprising a set of chart-specific acuity parameters of the one or more sets of chart-specific acuity parameters,
  - e) generating the probabilities of observing the acuity test data using the acuity model and the one or more sets of candidate acuity parameters;
  - f) ranking the one or more sets of candidate acuity parameters for the subject based on the probabilities; and
  - g) selecting one set from the one or more sets of candidate acuity parameters for the subject based on the rankings.

10. The system of claim 9, wherein each set of the candidate acuity parameters comprises: an acuity threshold, an acuity range, an acuity slope, a change in the acuity threshold between two test conditions, the change in the acuity range between two test conditions, the change in the acuity slope between two test conditions, or a combination thereof.

11. The system of claim 9, wherein each set of the candidate acuity parameters comprises a posterior probability density function for the one or more acuity parameters or for each of the one or more acuity parameters.

12. The system of claim 9, wherein the acuity test data of the subject comprises data from only a first test condition or a first and second test condition.

13. The system of claim 9, wherein the selected set of the candidate acuity parameters comprises a first posterior probability density function of an acuity threshold or an acuity range.

14. The system of claim 9 comprising:
- subsequent to g), select data with a second test condition from the acuity test data of the subject; and repeat c) to g); and
- obtaining a difference distribution using a first and second posterior probability density functions for an acuity threshold from at least two different test conditions.

15. The system of claim 9, wherein (d) comprises:
- generating a single-optotype psychometric function, the single-optotype psychometric function comprising a first set of chart-specific acuity parameters;
- calculating a family of multiple-optotype psychometric functions using the single-optotype psychometric function; and
- generating a chart-specific psychometric function using the family of multiple-optotype psychometric functions, the chart-specific psychometric function comprising a second set of chart-specific acuity parameters.

* * * * *